(12) United States Patent
van der Walt et al.

(10) Patent No.: US 11,911,119 B2
(45) Date of Patent: Feb. 27, 2024

(54) HIP REPLACEMENT NAVIGATION SYSTEM AND METHOD

(71) Applicant: OrthAlign, Inc., Aliso Viejo, CA (US)

(72) Inventors: Nicholas van der Walt, Laguna Hills, CA (US); Matthew Ryan, Aliso Viejo, CA (US); Jonathan Nielsen, Aliso Viejo, CA (US)

(73) Assignee: OrthAlign, Inc., Aliso Viejo, CA (US)

( * ) Notice: Subject to any disclaimer, the term of this patent is extended or adjusted under 35 U.S.C. 154(b) by 0 days.

(21) Appl. No.: 18/299,996

(22) Filed: Apr. 13, 2023

(65) Prior Publication Data

US 2023/0248447 A1    Aug. 10, 2023

Related U.S. Application Data

(63) Continuation of application No. 16/794,827, filed on Feb. 19, 2020, now Pat. No. 11,653,981, which is a
(Continued)

(51) Int. Cl.
*A61B 34/20* (2016.01)
*A61F 2/46* (2006.01)
(Continued)

(52) U.S. Cl.
CPC .......... *A61B 34/20* (2016.02); *A61B 17/1746* (2013.01); *A61B 90/10* (2016.02);
(Continued)

(58) Field of Classification Search
CPC .............. A61B 17/1742; A61B 17/175; A61B 2017/564
See application file for complete search history.

(56) References Cited

U.S. PATENT DOCUMENTS

| 3,174,080 | A | 3/1965 | Eldon |
| 3,670,324 | A | 6/1972 | Trevor, III |

(Continued)

FOREIGN PATENT DOCUMENTS

| CA | 2241359 | 12/1999 |
| CA | 2 594 874 | 7/2006 |

(Continued)

OTHER PUBLICATIONS 510 (k) Summary for Total Knee Surgetics Navigation System, in 5 pages.

(Continued)

*Primary Examiner* — Anu Ramana
(74) *Attorney, Agent, or Firm* — Knobbe, Martens, Olson & Bear, LLP

(57) ABSTRACT

In another embodiment, a hip joint navigation jig is provided that includes an anatomical interface comprising a bone engagement portion. A registration jig is also provided that is coupled, e.g., removeably, with the anatomical interface. A rotatable member is provided for rotation about an axis that is not vertical when the jig is mounted to the bone adjacent to a hip joint and the registration jig is coupled with the anatomical interface. An anatomy engaging probe is coupled with the rotatable member for rotation about the axis and is translatable to enable the probe to be brought into contact with a plurality of anatomical landmarks during a procedure. An inertial sensor is coupled with the probe to indicate orientation related to the landmarks, the sensor being disposed in a different orientation relative to horizontal when the probe is in contact with the landmarks.

17 Claims, 52 Drawing Sheets

Related U.S. Application Data continuation of application No. 15/474,037, filed on Mar. 30, 2017, now Pat. No. 10,603,115, which is a continuation of application No. 13/800,620, filed on Mar. 13, 2013, now Pat. No. 9,649,160.

(60) Provisional application No. 61/761,617, filed on Feb. 6, 2013, provisional application No. 61/683,167, filed on Aug. 14, 2012.

(51) Int. Cl.
*A61B 17/17* (2006.01)
*A61B 90/10* (2016.01)
*A61F 2/30* (2006.01)
*A61F 2/34* (2006.01)

(52) U.S. Cl.
CPC .......... *A61F 2/4609* (2013.01); *A61F 2/4657* (2013.01); *A61B 2034/2048* (2016.02); *A61B 2034/2068* (2016.02); *A61F 2/30942* (2013.01); *A61F 2/34* (2013.01); *A61F 2002/4687* (2013.01)

(56) References Cited

U.S. PATENT DOCUMENTS

| | | |
|---|---|---|
| 4,349,018 A | 9/1982 | Chambers |
| 4,421,112 A | 12/1983 | Mains et al. |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,067,821 A | 11/1991 | Young |
| 5,116,338 A | 5/1992 | Poggie et al. |
| 5,122,146 A | 6/1992 | Chapman et al. |
| 5,129,908 A | 7/1992 | Petersen |
| 5,141,512 A | 8/1992 | Farmer et al. |
| 5,171,244 A | 12/1992 | Caspari et al. |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Peterson |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliot et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allum |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,299,646 B1 | 10/2001 | Chambat et al. |
| 6,332,089 B1 | 12/2001 | Acker et al. |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,377,839 B1 | 4/2002 | Kalfas et al. |
| 6,381,485 B1 | 4/2002 | Hunter et al. |
| 6,383,149 B1 | 5/2002 | DeMayo |
| 6,395,005 B1 | 5/2002 | Lovell |
| 6,447,448 B1 | 9/2002 | Ishikawa et al. |
| 6,468,280 B1 | 10/2002 | Saenger et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |

(56) References Cited

U.S. PATENT DOCUMENTS

| | | |
|---|---|---|
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,648,896 B2 | 11/2003 | Overes et al. |
| 6,679,916 B1 | 1/2004 | Frankie et al. |
| 6,685,655 B2 | 2/2004 | DeMayo |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,802,864 B2 | 10/2004 | Tornier |
| 6,817,470 B1 | 11/2004 | Goldberg |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,311,441 B2 | 12/2007 | Weaver et al. |
| 7,331,932 B2 | 2/2008 | Leitner |
| 7,344,541 B2 | 3/2008 | Haines et al. |
| 7,392,076 B2 | 6/2008 | Moctezuma de la Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,594,933 B2 | 9/2009 | Kammerzell et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,815,644 B2 | 10/2010 | Masini |
| 7,831,292 B2 | 11/2010 | Quaid et al. |
| 7,834,847 B2 | 11/2010 | Boillot et al. |
| 7,840,256 B2 | 11/2010 | Lakin et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,104,960 B2 | 1/2012 | Gill et al. |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,867,198 B2 | 10/2014 | Steele |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,138,319 B2 * | 9/2015 | Fanson ................. A61B 34/20 |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,642,572 B2 | 5/2017 | Mahfouz et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,930,946 B2 | 4/2018 | Zondervan |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 10,597,178 B2 | 3/2020 | Ryterski et al. |
| 10,603,115 B2 | 3/2020 | van der Walt et al. |
| 10,716,580 B2 | 7/2020 | Berend et al. |
| 10,863,995 B2 | 12/2020 | Nielsen et al. |
| 10,864,019 B2 | 12/2020 | van der Walt et al. |
| 10,869,771 B2 | 12/2020 | van der Walt et al. |
| 10,918,499 B2 | 2/2021 | Nielsen et al. |
| 11,020,245 B2 | 6/2021 | van der Walt et al. |
| 11,179,062 B2 | 11/2021 | Borja et al. |
| 11,179,167 B2 | 11/2021 | Stone |
| 11,191,334 B2 | 12/2021 | Aghazadeh et al. |
| 11,273,232 B2 | 3/2022 | Placik |
| 11,540,746 B2 | 1/2023 | Borja et al. |
| 11,547,451 B2 | 1/2023 | van der Walt et al. |
| 11,547,580 B2 | 1/2023 | Nielsen et al. |
| 11,633,293 B2 | 4/2023 | van der Walt et al. |
| 11,653,981 B2 | 5/2023 | van der Walt et al. |
| 11,684,392 B2 | 6/2023 | van der Walt et al. |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0163142 A1 | 8/2003 | Paltieli et al. |
| 2003/0181919 A1 | 9/2003 | Gorek |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0073225 A1 | 4/2004 | Subba Rao |

(56) References Cited

U.S. PATENT DOCUMENTS

| | | |
|---|---|---|
| 2004/0087958 A1 | 5/2004 | Myers et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0122441 A1 | 6/2004 | Muratsu |
| 2004/0147926 A1 | 7/2004 | Iversen |
| 2004/0149036 A1 | 8/2004 | Foxlin et al. |
| 2004/0152955 A1 | 8/2004 | McGinley et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0070864 A1 | 3/2005 | Fellion |
| 2005/0107799 A1 | 5/2005 | Graf et al. |
| 2005/0113846 A1 | 5/2005 | Carson |
| 2005/0149040 A1 | 7/2005 | Haines et al. |
| 2005/0149054 A1 | 7/2005 | Gorek |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1 | 11/2005 | Stone |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0084977 A1 | 4/2006 | Lieberman |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0149276 A1 | 7/2006 | Grimm |
| 2006/0161051 A1 | 7/2006 | Terrill-Grisoni et al. |
| 2006/0184177 A1 | 8/2006 | Echeverri |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0244488 A1 | 10/2007 | Metzger et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0108912 A1 | 5/2008 | Node-Langlois |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0070038 A1* | 3/2009 | Geelen .................. G01S 19/49 701/472 |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0099665 A1 | 4/2009 | Taylor et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0087829 A1 | 4/2010 | Metzger et al. |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0241126 A1 | 9/2010 | Ghijselings |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |

(56) References Cited

U.S. PATENT DOCUMENTS

| | | |
|---|---|---|
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana et al. |
| 2011/0208093 A1 | 8/2011 | Gross et al. |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0157887 A1 | 6/2012 | Fanson et al. |
| 2012/0172712 A1 | 7/2012 | Bar-Tal |
| 2012/0172884 A1 | 7/2012 | Zheng et al. |
| 2012/0203140 A1 | 8/2012 | Malchau et al. |
| 2012/0316567 A1 | 12/2012 | Gross et al. |
| 2013/0053859 A1 | 2/2013 | Penenberg |
| 2013/0064478 A1 | 3/2013 | Sold et al. |
| 2013/0066323 A1 | 3/2013 | Nycz et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |
| 2014/0031672 A1 | 1/2014 | McCaulley et al. |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0182062 A1 | 7/2014 | Aghazadeh |
| 2014/0224685 A1 | 8/2014 | Carnevali |
| 2014/0270583 A1 | 9/2014 | Anderson |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0100058 A1 | 4/2015 | van der Walt et al. |
| 2015/0127009 A1 | 5/2015 | Berend et al. |
| 2015/0142372 A1 | 5/2015 | Singh |
| 2015/0143781 A1 | 5/2015 | Agnihotri |
| 2015/0150569 A1 | 6/2015 | van der Walt et al. |
| 2015/0164657 A1 | 6/2015 | Miles et al. |
| 2015/0238204 A1 | 8/2015 | Stone |
| 2015/0245914 A1 | 9/2015 | Langton |
| 2015/0272478 A1 | 10/2015 | Borja |
| 2015/0313723 A1 | 11/2015 | Jansen |
| 2015/0342516 A1 | 12/2015 | Nguyen et al. |
| 2016/0038242 A1 | 2/2016 | Lo Iacono et al. |
| 2016/0175055 A1 | 6/2016 | Hook et al. |
| 2016/0213383 A1 | 7/2016 | van der Walt et al. |
| 2016/0220315 A1 | 8/2016 | Falardeau |
| 2016/0220318 A1 | 8/2016 | Falardeau et al. |
| 2016/0220385 A1 | 8/2016 | Falardeau et al. |
| 2016/0242934 A1 | 8/2016 | van der Walt et al. |
| 2016/0278943 A1 | 9/2016 | van der Walt et al. |
| 2016/0346044 A1 | 12/2016 | Brown et al. |
| 2017/0196571 A1 | 7/2017 | Berend et al. |
| 2017/0238946 A1 | 8/2017 | van der Walt et al. |
| 2017/0296203 A1 | 10/2017 | Stone |
| 2018/0064496 A1 | 3/2018 | Hladio et al. |
| 2018/0153587 A1 | 6/2018 | van der Walt et al. |
| 2018/0168826 A1 | 6/2018 | van der Walt et al. |
| 2018/0177509 A1 | 6/2018 | Trabish et al. |
| 2018/0193171 A1 | 7/2018 | van der Walt et al. |
| 2018/0206860 A1 | 7/2018 | van der Walt et al. |
| 2018/0235762 A1 | 8/2018 | Radermacher et al. |
| 2018/0296232 A1 | 10/2018 | Nielsen et al. |
| 2018/0296365 A1 | 10/2018 | Nielsen et al. |
| 2019/0254715 A1 | 8/2019 | van der Walt et al. |
| 2019/0328549 A1 | 10/2019 | van der Walt et al. |
| 2019/0350728 A1 | 11/2019 | van der Walt et al. |
| 2019/0357809 A1 | 11/2019 | Borja et al. |
| 2020/0352654 A1 | 11/2020 | van der Walt et al. |
| 2020/0390501 A1 | 12/2020 | Brown et al. |
| 2021/0153880 A1 | 5/2021 | Nielsen et al. |
| 2021/0153908 A1 | 5/2021 | van der Walt et al. |
| 2021/0186711 A1 | 6/2021 | van der Walt et al. |
| 2021/0220152 A1 | 7/2021 | Nielsen et al. |
| 2021/0315716 A1 | 10/2021 | van der Walt et al. |
| 2022/0071509 A1 | 3/2022 | Borja et al. |
| 2022/0240953 A1 | 8/2022 | Stone |
| 2022/0313455 A1 | 10/2022 | van der Walt et al. |
| 2022/0378516 A1 | 12/2022 | Sierra et al. |
| 2023/0059247 A1 | 2/2023 | Gannoe |
| 2023/0135541 A1 | 5/2023 | Borja et al. |
| 2023/0149185 A1 | 5/2023 | Nielsen et al. |
| 2023/0157727 A1 | 5/2023 | van der Walt et al. |
| 2023/0277335 A1 | 9/2023 | van der Walt et al. |

FOREIGN PATENT DOCUMENTS

| | | |
|---|---|---|
| CA | 2 537 711 | 8/2007 |
| CN | 109846528 | 6/2019 |
| DE | 4 225 112 | 12/1993 |
| DE | 29704393 | 8/1997 |
| DE | 198 30 359 | 1/2000 |
| DE | 20116368 | 12/2001 |
| EP | 0 557 591 | 9/1993 |
| EP | 0 651 968 | 5/1995 |
| EP | 1 635 705 | 3/2006 |
| EP | 1 817 547 | 4/2012 |
| EP | 2 957 249 | 12/2015 |
| EP | 3 395 281 | 10/2018 |
| GB | 2 197 790 | 6/1988 |
| GB | 2 511 885 | 9/2014 |
| JP | 07-184929 | 7/1995 |
| JP | H08-240611 | 9/1996 |
| JP | 2006-314775 | 11/2006 |
| JP | 2006-528496 | 12/2006 |
| JP | 2007-503289 | 2/2007 |

(56) References Cited

FOREIGN PATENT DOCUMENTS

| | | |
|---|---|---|
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| JP | 2013-000230 | 1/2013 |
| JP | 2014-524815 | 9/2014 |
| JP | 2015-524733 | 8/2015 |
| JP | 2015-226613 | 12/2015 |
| JP | 6980248 | 11/2021 |
| JP | 7180159 | 11/2022 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/113054 | 8/2012 |
| WO | WO 2013/012561 | 1/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2014/063181 | 5/2014 |
| WO | WO 2014/197988 | 12/2014 |
| WO | WO 2015/054745 | 4/2015 |
| WO | WO 2016/070288 | 5/2016 |
| WO | WO 2016/134168 | 8/2016 |
| WO | WO 2016/147153 | 9/2016 |
| WO | WO 2016/154489 | 9/2016 |
| WO | WO 2017/093769 | 6/2017 |
| WO | WO 2018/085900 | 5/2018 |
| WO | WO 2018/169980 | 9/2018 |
| WO | WO 2018/169995 | 9/2018 |
| WO | WO 2019/036752 | 2/2019 |
| WO | WO 2021/119001 | 6/2021 |
| WO | WO 2021/188798 | 9/2021 |
| WO | WO 2022/165561 | 8/2022 |

OTHER PUBLICATIONS 510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Microsurgical Accuracy, Medical Image Computing and Computer-Assisted Intervention, 2000, vol. 1935, pp. 878-887.
Arnold-Moore, et al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bae et al., "Computer Assisted Navigation in Knee Arthroplasty", Clinics in Orthopedic Surgery, 2011, vol. 3, pp. 259-267.
Bargren, MD., et al,, Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, p. 13 pages.
Brainlab, "Position Determination and Calibration in optical tracking systems", FLORENUS the technology merchants, in 2 pages.
Brainlab, "Tracking and imaging in Navigation", FLORENUS, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, p. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
European Office Action for Application No. 04776379.2, dated May 4, 2010, in 5 pages.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
IASSIST Knee, Surgical Technique, Zimmer, Inc., 2012.
International Preliminary Report for Application No. PCT/US2004/018244, dated Dec. 13, 2005, in 11 pages.

(56) References Cited

OTHER PUBLICATIONS

International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, pp. in 88 pages.
MacKenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA Genesis II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Partial Supplemental European Search Report issued in European Patent Application No. 13829614.0, dated Jun. 13, 2016, in 6 pages.
Perseus Intelligent Cutting Guide, Orthokey, Product Guide, in 8 pages.
Perseus Intelligent Cutting Guide, Smart Instruments for Knee Arthroplasty, Orthokey, in 2 pages.

Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
Supplementary European Search Report issued in European Patent Application No. 13829614.0, dated Sep. 22, 2016, in 8 pages.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, dated Mar. 14, 2005, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.

(56) References Cited

OTHER PUBLICATIONS

Shah et al., "Is the pelvis stable during supine total hip arthroplasty?", Acta Orthop Belg., Mar. 1, 2017, vol. 83, No. 1, pp. 81-86.

* cited by examiner

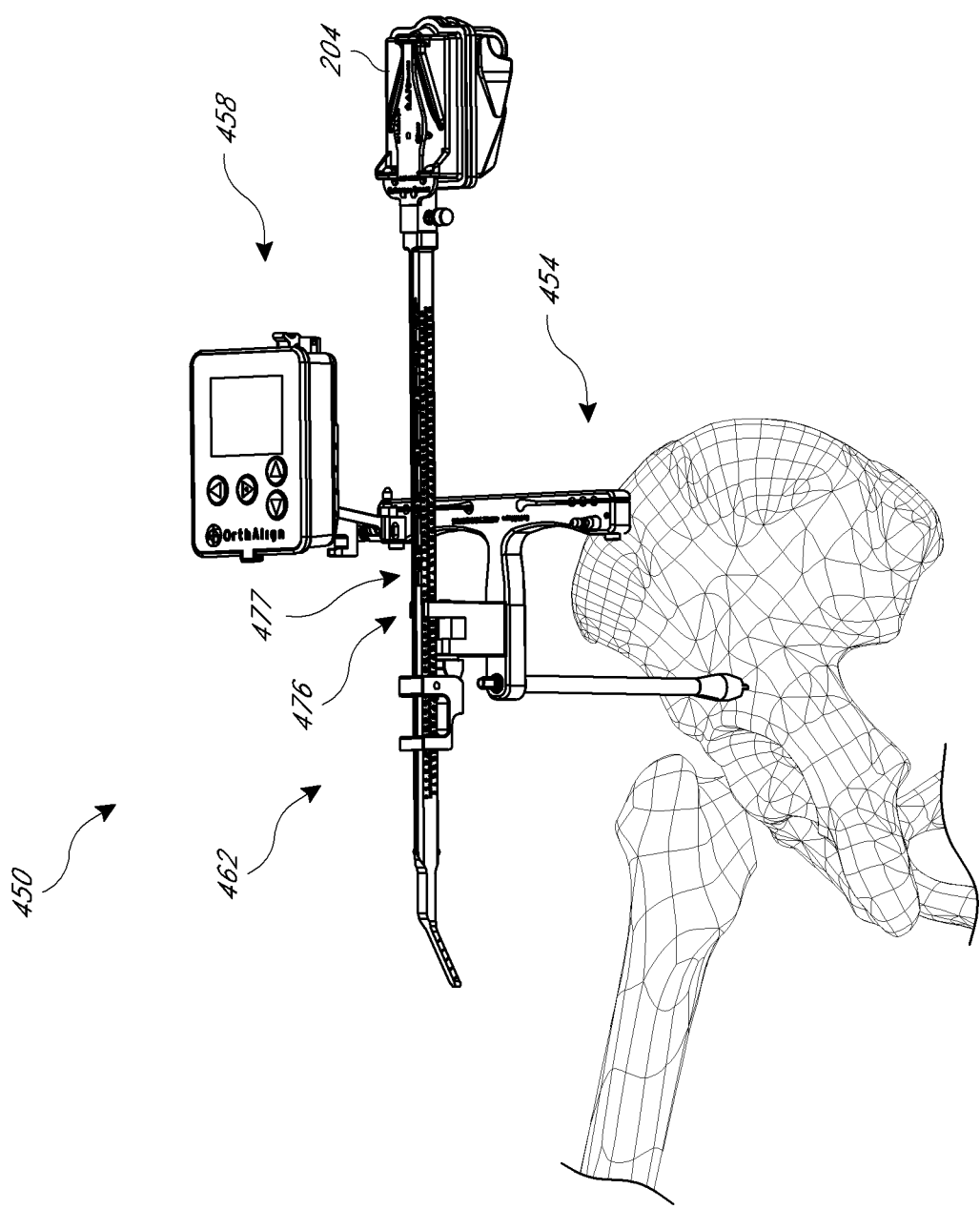

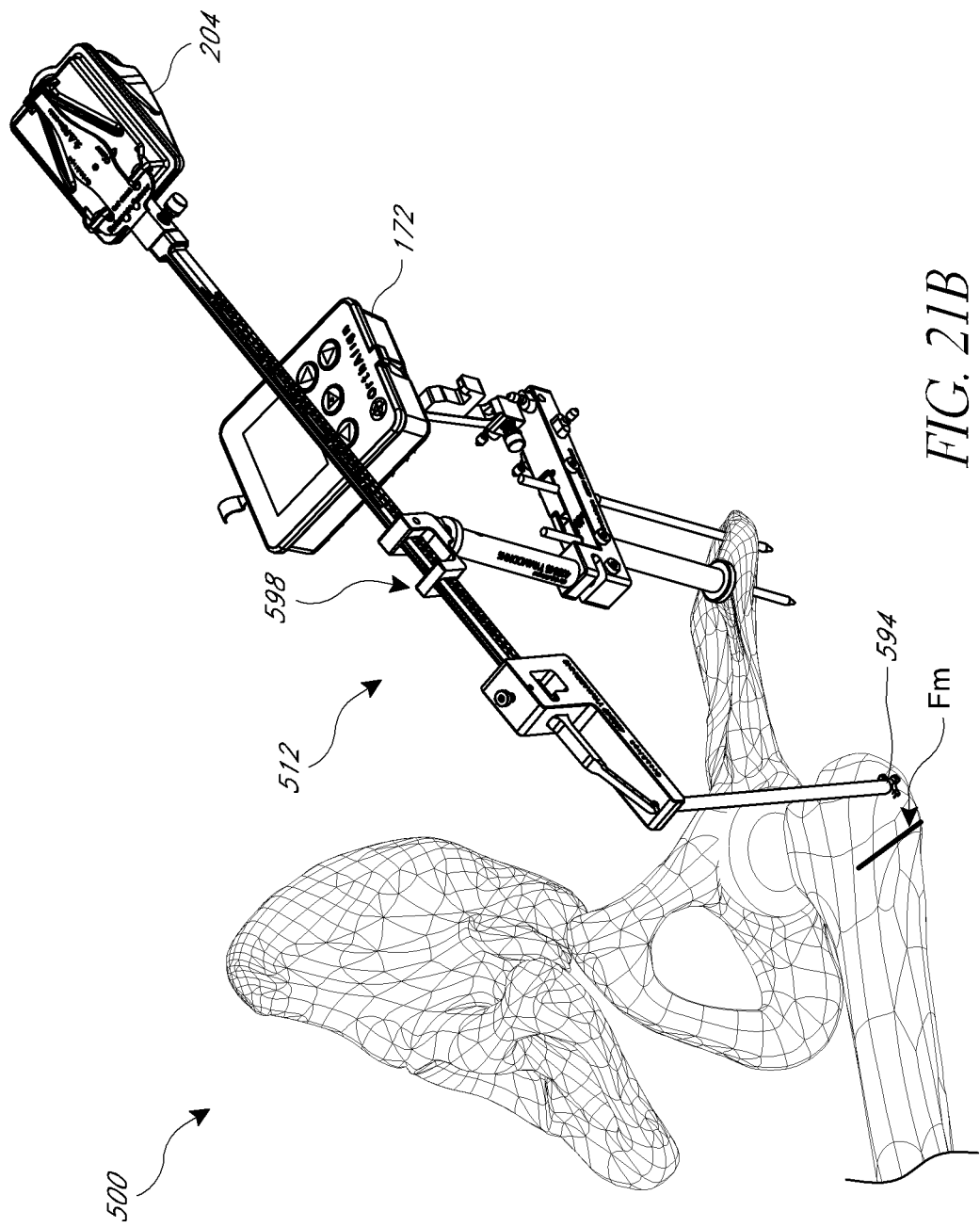

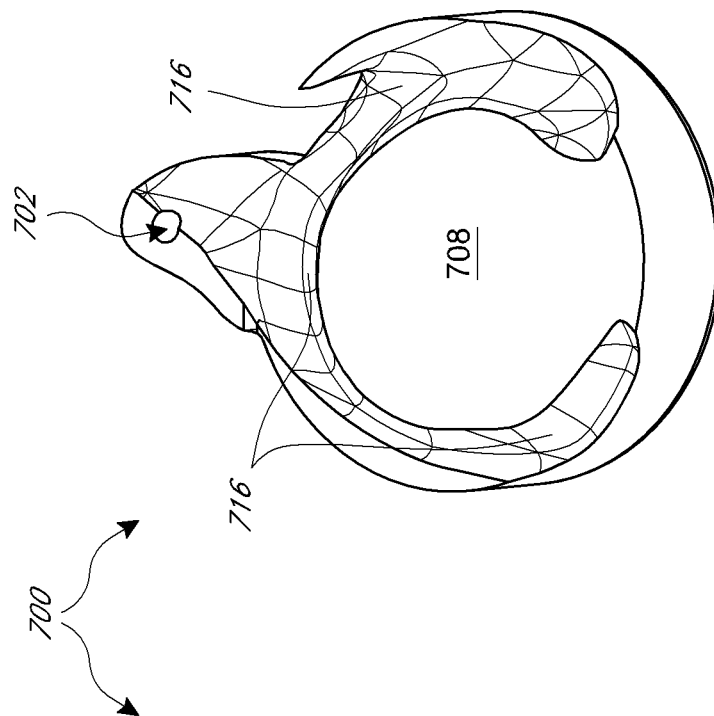
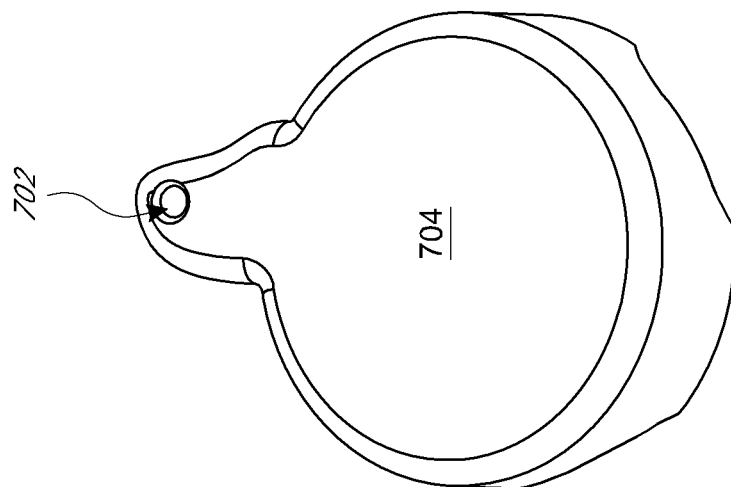
FIG. 23

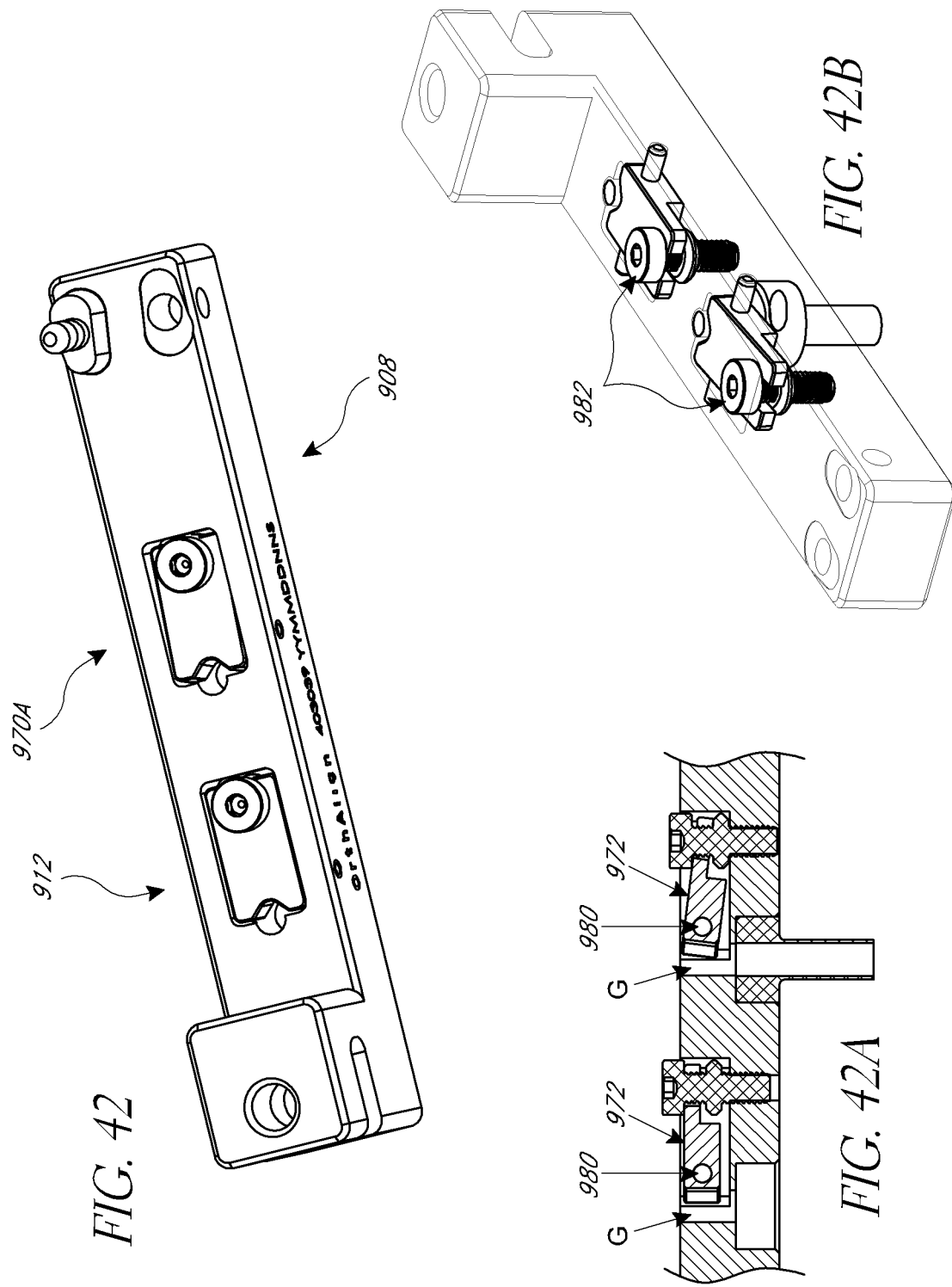

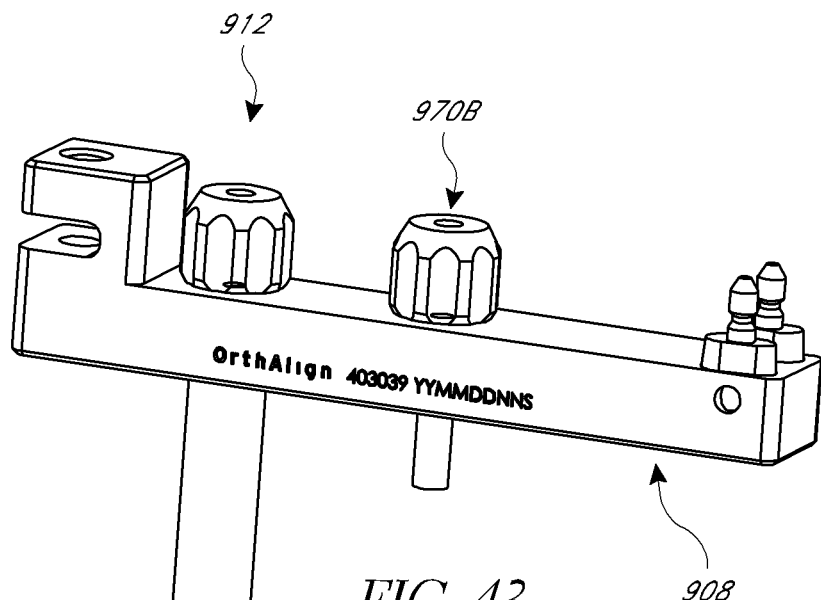
FIG. 43
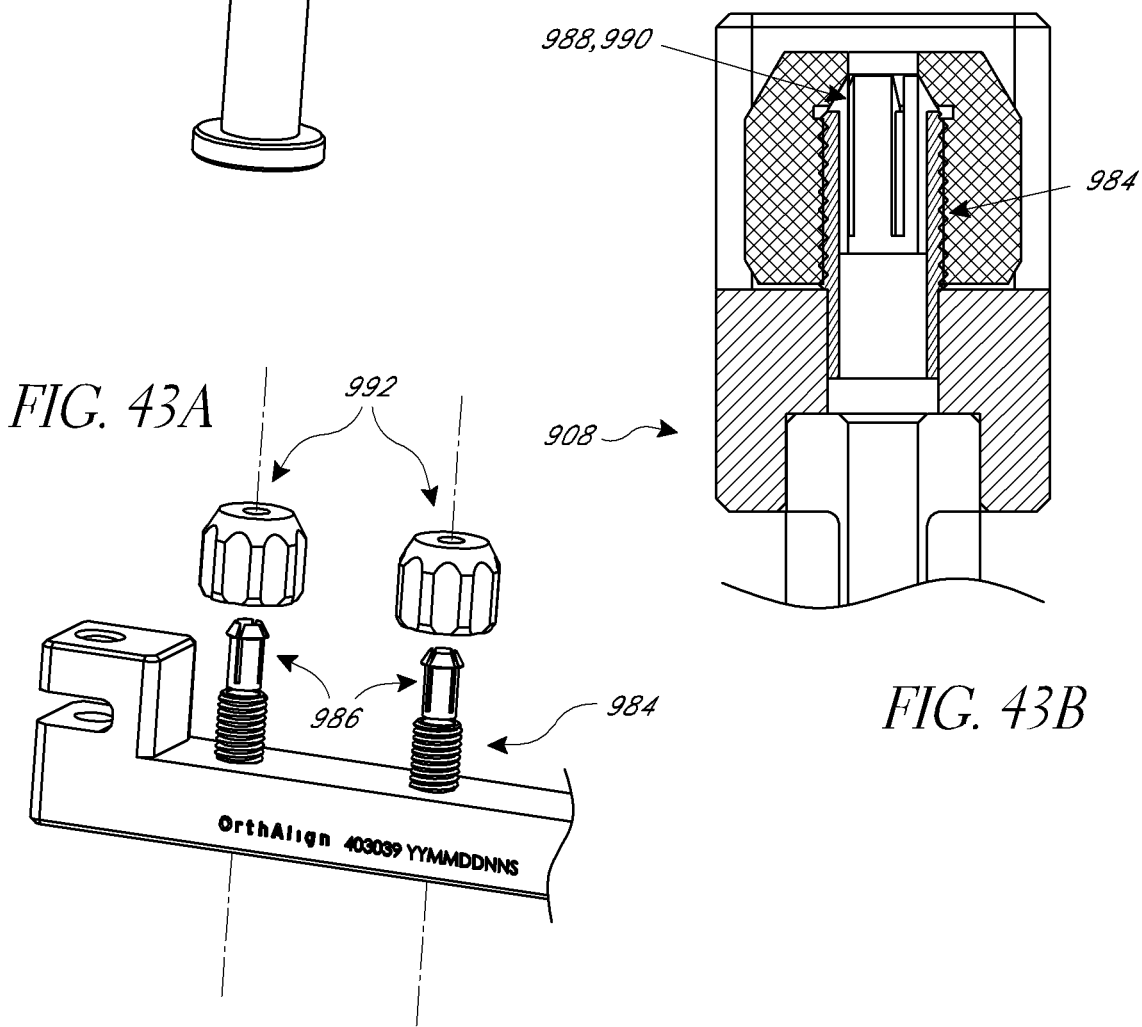
FIG. 43A
FIG. 43B

HIP REPLACEMENT NAVIGATION SYSTEM AND METHOD

INCORPORATION BY REFERENCE TO ANY PRIORITY APPLICATIONS

The present application is a continuation of U.S. patent application Ser. No. 16/794,827, filed Feb. 19, 2020, and issued as U.S. Pat. No. 11,653,981, which is a continuation of U.S. patent application Ser. No. 15/474,037, filed Mar. 30, 2017, and issued as U.S. Pat. No. 10,603,115, which is a continuation of U.S. patent application Ser. No. 13/800,620, filed Mar. 13, 2013, and issued as U.S. Pat. No. 9,649,160, which claims priority under 35 U.S.C. § 119(e) to U.S. Provisional Application No. 61/683,167 filed on Aug. 14, 2012 and U.S. Provisional Application No. 61/761,617 filed on Feb. 6, 2013. Any and all applications for which a foreign or domestic priority claim is identified in the Application Data Sheet as filed with the present application including U.S. patent application Ser. No. 13/800,620 filed Mar. 13, 2013, U.S. provisional application No. 61/683,167, filed Aug. 14, 2012, and U.S. provisional application No. 61/761, 617, filed Feb. 6, 2013, are hereby incorporated by reference under 37 CFR 1.57.

BACKGROUND OF THE INVENTION

Field of the Invention

This application is directed to the field of hip replacement, and particularly to surgical tools and methods for guiding the preparation of the bones in connection therewith.

Description of the Related Art

Hip replacement surgery is common and getting more common by the year. One persistent issue with hip replacement is the relatively high incidence of poor placement of the cup and ball components of the prosthetic hip joint. For example, the cup is optimally placed in a specific alignment with a plane including a rim of the acetabulum of the pelvis. For several reasons an unacceptably high percentage of patients have the cup of the artificial hip joint out of alignment with this plane.

Unfortunately, misalignment can lead to dislocation of the hip as soon as within one year of the implantation procedure. This is particularly problematic because recovery from a hip procedure can take many months. Patients undergoing a revision so soon after the initial implantation will certainly be dissatisfied with their care, being subject to addition redundant surgery. Of course, all surgery carries some degree of risk. These poor outcomes are unsatisfactory for patients and surgeons and are inefficient for the healthcare system as a whole.

Also, in cup placement in total hip arthroplasty, the inclination and anteversion angles are with respect to the Anterior Pelvic Plane (defined as a plane created by the two anterior superior iliac spines (ASIS) and the pubic symphysis). While these anatomical features are visible/palpable while the patient is in a supine position, the majority of total hip replacements are accomplished via a posterolateral approach with the patient in some variation of a lateral position, in which most of these landmarks are not accessible or visible. Historically, navigation for posterior approach hip replacement has been accomplished by registering the anatomical features of the Anterior Pelvic Plane with the patient first in a supine position and, once this plane is recorded by the navigation computer, moving the patient to a lateral position in order to perform hip surgery—with navigation performed with respect to the directly registered Anterior Pelvic Plane. This approach to hip navigation is sub-optimal for surgical workflow because the extra movement of the patient from supine to lateral position takes more surgeon and staff time and requires breaking sterility and re-draping. This is one of the key reasons why hip navigation has failed to be adopted by most of the market.

Additionally, altered leg length is a common patient complaint arising from hip replacement surgery and has been a common cause of medical malpractice lawsuits that arise from hip replacement. Because part of the hip replacement procedure requires precise measurements of patient leg length and joint off-set that are frequently difficult to visualize utilizing conventional instrumentation, there are opportunities to improve the surgeon's performance of these measurements using computer technology.

SUMMARY OF THE INVENTION

There is a need for improved systems and methods for providing for proper alignment of hip components with a patient's anatomy during a hip replacement procedure. This can involve techniques for locating one or more anatomical landmarks, e.g., discrete anatomy and/or planes including multiple points. This can involve techniques for confirming alignment of a prosthetic component with an anatomical landmark.

In one embodiment, a method is provided for navigating a hip joint replacement procedure. The method includes advancing a first portion of a jig into a portion of the pelvis. The portion of the pelvis is an anatomical landmark in some techniques. In others it is not. At least one inertial sensor is coupled to the jig. The second portion of the jig is moved relative to the first portion to touch, e.g., sequentially, a plurality of anatomical landmarks. This can include touching two or three landmarks, for example. A cup portion of a replacement joint is placed in the acetabulum by reference to a plane calculated based on data from the at least one of a plurality of inertial sensors.

In another embodiment, a hip joint navigation system is provided. The system includes a jig, a first inertial navigation device and a second inertial navigation device. The jig has an anchor portion adapted to be placed on the hip, e.g., at an anatomical landmark. The jig also has a landmark acquisition probe coupled with the anchor portion. The probe is moveable in at least three degrees of freedom. The first inertial navigation device is configured to be fixed to a pelvis of a patient to track movements of the pelvis. The first inertial navigation device can be immovably connected to the pelvis. The second inertial navigation device is coupled with the landmark acquisition probe. The landmark acquisition probe can be moved to touch a plurality of landmarks. The inertial navigation devices determine the orientation of a plane of the acetabulum based at least in part on the position of the anatomical landmarks.

In another embodiment, a method of navigating a hip replacement procedure is provided. A first hip of a patient is positioned on a surgical table and a second hip is positioned off of the table such that the anterior pelvic plane is disposed upright (e.g., vertically). A jig is coupled with a bone adjacent to a second hip joint. The jig has a moveable orientation guide. An inertial sensor is coupled with the orientation guide. The orientation guide can be an arm of a registration probe in some embodiments. The orientation guide is oriented in a plane substantially parallel to the plane of the table. The orientation of the inertial sensor is recorded as an indication of the orientation of the anterior pelvic plane. If the anterior pelvic plane is vertical the inertial sensor can indicate the plane of the table, which is perpendicular to the anterior pelvic plane. A cup of an artificial hip joint is placed in the acetabulum with reference to the orientation of the anterior pelvic plane based on the orientation of the inertial sensor.

In another embodiment, a system for determining orientation data in connection with a hip joint procedure is provided. The system includes a data capture module, a computational module, and a user interface module. The data capture module is configured to receive inertial data from an inertial sensor. The computational module is configured to provide, based on the inertial data, one or more angles of a proxy acetabular plane relative to an anterior pelvic plane. The user interface module is configured to output a user interface configured to communicate orientation data to a user. One or more of these modules is implemented by one or more processors.

In another embodiment, a method of navigating a hip replacement procedure is provided. A patient is positioned for posterior or posterolateral approach. A jig is coupled with a bone adjacent to a hip joint. The jig comprising a landmark acquisition probe having an inertial sensor coupled therewith. Patient condition can be assessed, and based on the patient condition, a selection can be made between a first plurality of landmarks and a second set of landmarks. The first set of landmarks can be disposed on an acetabular rim. The plurality of landmarks can be disposed off of an acetabular rim. The orientation of the inertial sensor can be recorded when the landmark acquisition probe is in contact with each of the points of the selected plurality. A cup of an artificial hip joint is positioned in the acetabulum with reference to the recorded orientation to the selected plurality of points.

In another approach, a method of navigating a procedure on a hip joint is provided. At least one aspect of the hip joint is characterized pre-operatively. A patient is positioned for posterior or posterolateral approach. A jig is coupled with a bone adjacent to the hip joint (e.g., part of the pelvis). The jig has a landmark acquisition probe having an inertial sensor coupled therewith. The orientation of the inertial sensor is recorded when the landmark acquisition probe is in contact with each of a plurality of landmarks. A cup of an artificial hip joint is positioned in the acetabulum with reference to recorded orientation and to estimations of at least one of anteversion and inclination angles. Estimations of these angles can be based upon the pre-operatively recorded characterization of the hip joint. The recorded orientation can be that of the inertial sensor when the probe is in contact with each of the landmarks.

In another embodiment, a method of navigating a hip replacement procedure is provided. The method includes positioning a patient for posterior or posterolateral approach. A jig is coupled with an acetabular socket of the patient, the jig having an engagement surface formed to closely mate to acetabular bone contours of the specific patient. The jig comprising a registration feature configured to be in a pre-determined orientation relative to the anterior pelvic plane of the patient when the jig is so-coupled. An inertial sensor is coupled with the registration feature such that the inertial sensor generates a signal indicating at least one angle relative to the anterior pelvic plane. A prosthetic cup is placed based on the signal.

In another embodiment, a patient specific jig system for hip replacement is provided. The jig system includes an engagement surface and a registration feature. The engagement surface is formed to closely mate to acetabular bone contours of a specific patient. The registration feature is configured to be in a pre-determined orientation relative to the anterior pelvic plane of the patient when the jig is coupled to closely mate to acetabular bone contours of the specific patient.

In another embodiment, a method of replacing a hip joint is provided. The method includes coupling a trackable member with a limb forming a part of a hip joint of the patient. The limb is moved to at least four points disposed away from a neutral position of the hip. The four points include at least one medial extent, at least one lateral extent, at least one anterior extent, and at least one posterior extent of a patient's range of motion. During the moving step, data is collected from the trackable member indicating the displacement from the neutral position to each of the extents. A socked component of the prosthetic hip joint is placed within the acetabulum. A stem of a femoral component of a prosthetic hip joint is placed into a proximal femur. A ball of the femoral component is placed in the socket component. In the method, when the prosthetic hip joint is in the neutral position, a stem axis connecting the center of rotation of the ball and a centroid of the stem at the mouth of the socket component is in a central zone between the at least four extents. At least one of the steps of placing is performed with the aid of a display of the position and/or orientation of the stem axis relative to the central zone.

In the system described above, the inertial navigation devices can be replaced with or supplemented by one or more cameras for monitoring distance, linear position, or angular position.

In the system described above, the inertial navigation devices can be replaced with or supplemented by one or more cameras for determining the spatial position of trackers coupled with instruments, such as a stylus. In such a system, the jig can be simplified without requiring moveable portions for example.

In some variations of the methods discussed herein, patient data can be used to enhance the accuracy of orientation of a component, such as the plane of the acetabulum. Patient data can include CT, MM, X-Ray or other pre-operative planning data.

In another embodiment, a hip joint navigation jig is provided that includes a platform, a cannula coupling device, and a registration jig mounting feature. The cannula coupling device is disposed on the platform and is configured to enable a cannula to be detachably coupled with a bottom surface of the platform. The cannula is configured for detachably coupling the platform with a bone adjacent to a hip joint. The registration jig mounting feature is disposed on the platform. The hip navigation jig also includes registration jig. The registration jig includes an upright member, a rotatable member, and a probe. The upright member is configured to be detachably coupled to the platform at the registration jig mounting feature. The rotatable member is coupled with the upright member for rotation about an axis that is not vertical when the jig is mounted to the bone adjacent to a hip joint and the upright member is disposed generally vertically. The probe had a tip for engaging anatomy. The anatomy engaging tip is disposed at a distal end of an elongate body coupled with the rotatable member for rotation about the axis. The orientation and position of the elongate body of the probe can be adjusted to bring the anatomy engaging tip into contact with a plurality of anatomical landmarks during a landmark acquisition maneuver.

Although the platform can have any shape or configuration, it is elongate in some implementations, for example, including a first end and a second end. The first end can be configured to be oriented inferiorly and the second end to be oriented superiorly when the navigation jig is applied to the patient. If the platform is elongate, the cannula coupling device can be disposed adjacent to the first end, which may be located inferior of the second end when placed on the patient. The cannula coupling device can be detachably coupled with a bottom surface of the platform in some embodiments. The registration jig mounting feature is disposed on a top surface of the platform and can be positioned adjacent to the first end. Again, the first end may be inferior end, just superior to or at the superior portion of the surgical field.

In another embodiment, a hip joint navigation jig is provided that includes an anatomical interface comprising a bone engagement portion. A registration jig is also provided that is coupled, e.g., removeably, with the anatomical interface. A rotatable member is provided for rotation about an axis that is not vertical when the jig is mounted to the bone adjacent to a hip joint and the registration jig is coupled with the anatomical interface. An anatomy engaging probe is coupled with the rotatable member for rotation about the axis and is translatable to enable the probe to be brought into contact with a plurality of anatomical landmarks during a procedure. An inertial sensor is coupled with the probe to indicate orientation related to the landmarks, the sensor being disposed in a different orientation relative to horizontal when the probe is in contact with the landmarks.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments.

FIGS. 17-17C-2 illustrate modified systems configured for navigating a posterior approach hip replacement procedure.

FIGS. 22-31 illustrate various aspects of methods involving custom patient-specific positioning jigs.

FIGS. 42-42B illustrate a second embodiment of pin securement devices.

FIGS. 43-43B illustrate a third embodiment of pin securement devices.

DETAILED DESCRIPTION OF THE PREFERRED EMBODIMENTS

A variety of systems and methods are discussed below that can be used to improve outcomes for patients by increasing the likelihood of proper placement of a hip joint. These systems can be focused on inertial navigation techniques, close range optical navigation, or a combination of inertial and optical navigation.

I. Hip Navigation Using Inertial Sensors

Systems and methods described below can improve prosthetic hip joint placement using navigation in connection with referencing anatomical landmarks, incorporating pre-operative custom fit jigs based on imaging, and a combination of pre-operative imaging and landmark referencing. These hip procedures generally guide a prosthetic hip to an orientation within the acetabulum that minimizes the chance of dislocation due to impingement of the femoral neck on the cup or on bones around the acetabulum or other reasons related to suboptimal orientation of the prosthetic. Various techniques leverage population averages of proper placement while others are amenable to patient specific refinements. Also various techniques for registering and confirming the position and/or orientation of the femur pre- and post-implantation are discussed herein, which are useful to control leg length and joint offset at the end of the procedure.

A. Navigation Using Inertial Sensors and Jigs for Referencing Anatomical Landmarks with Posterior Approach Most hip replacement procedures presently are performed from a posterior approach. In this approach, the patient is positioned on his/her side and the anterior pelvic plane is oriented vertically, e.g., perpendicular to the plane of the table on which the patient is positioned. Most surgeons performing hip replacement are very familiar with this approach and will immediately recognize the benefit of enhanced certainty about the orientation of the relevant anatomy when the patient is in this position.

1. Apparatuses And Methods for Posterior Approach Hip Navigation

Figure 1:
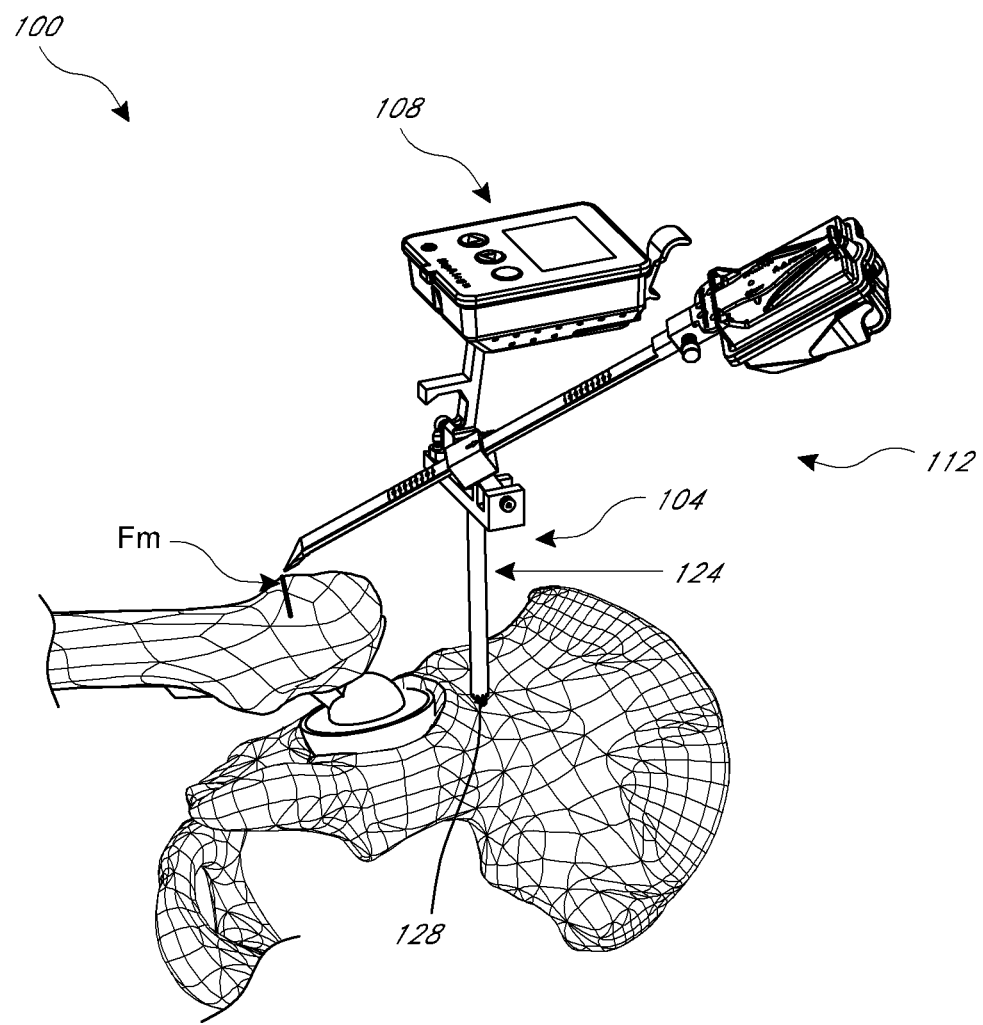
FIG. 1 is a perspective view of a hip navigation system applied to a patient illustrating a measurement of leg length and/or joint offset after implantation of the prosthetic hip joint.
Figure 4:
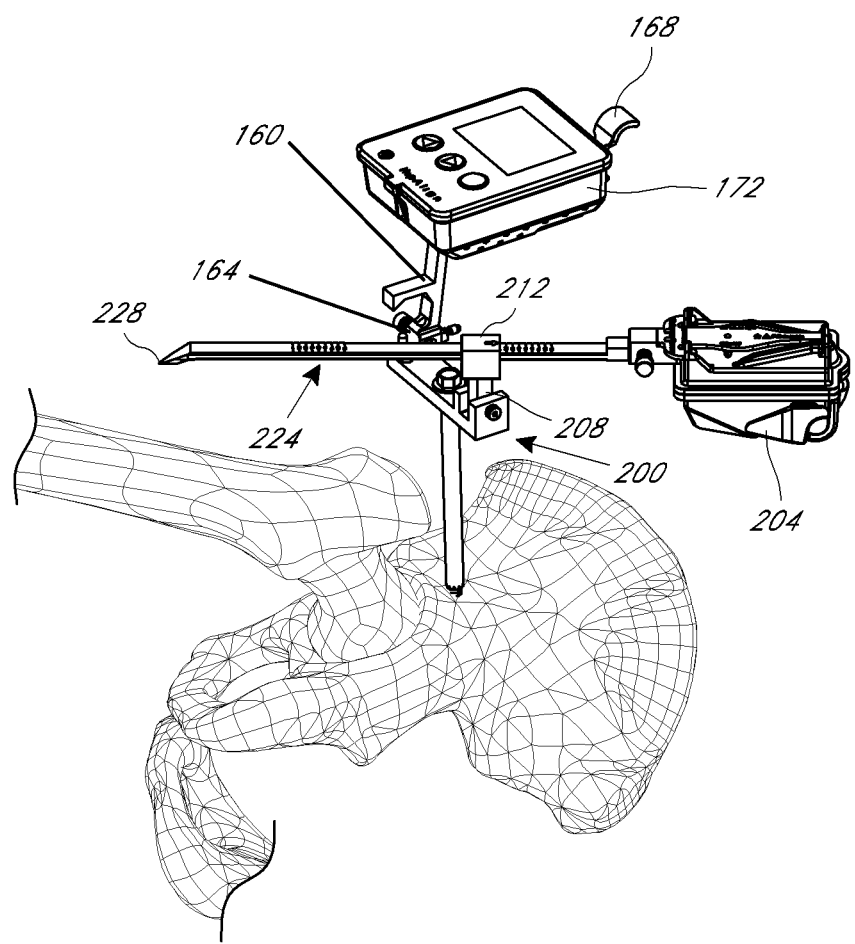
FIG. 4 is a perspective view illustrating first and second orientation detecting devices coupled with the base of FIG. 3.

FIGS. 1 and 4 show a hip navigation system 100 adapted to navigate a hip joint procedure with reference to anatomical landmarks without requiring, but not necessarily excluding, pre-operative imaging or other inputs apart from those discussed below. The system 100 is shown mounted on a pelvis in a posterior approach in FIG. 1. FIG. 4 shows an early phase of a procedure prior to the joint being dislocated but after the system 10 is mounted to the pelvis. FIG. 1 shows a late phase of some variations of techniques for which the system 100 is adapted. As discussed further below, such variations involve registering the femur prior to and after the joint is replaced to confirm an aspect of the relative position and/or orientation of the femur, e.g., leg length, joint offset, and rotational orientation of the femoral neck.

The system 100 includes a registration jig 104, an alignment assembly 108 and a landmark acquisition assembly 112. The alignment assembly 108 is rigidly connected to the hip in the illustrated configuration so that motion of the hip cause corresponding motion of sensor(s) in the assembly 108 as discussed below. Sensing this motion enables the system 100 to eliminate movement of the patient as a source of error in the navigation. The landmark acquisition assembly 112 provides a full range of controlled motion and sensor(s) that are able to track the motion, in concert with sensor(s) in the assembly 108. Additional details of systems, devices, sensors, and methods are set forth in U.S. Pat. No. 8,118,815; US US2010/0076505; and U.S. Pat. No. 8,057,479 which are all incorporated by reference herein in their entireties for all purposes. The sensors in assemblies 108, 112 preferably transfer data among themselves and in some cases with external devices and monitors wirelessly, using Bluetooth, Wifi® or other standard wireless telemetry protocol.

The registration jig 104 includes a fixation cannula 124 that has a distal end that can be advanced to a pelvic bone at an anatomical location or landmark or other selected location. In the illustrated technique, the cannula 124 is secured by a pin 132 (see FIG. 3) that is driven into the ilium on the pelvis through the cannula 124. A distal end 128 of the pin 132 is shown in FIG. 1.

Figure 2:
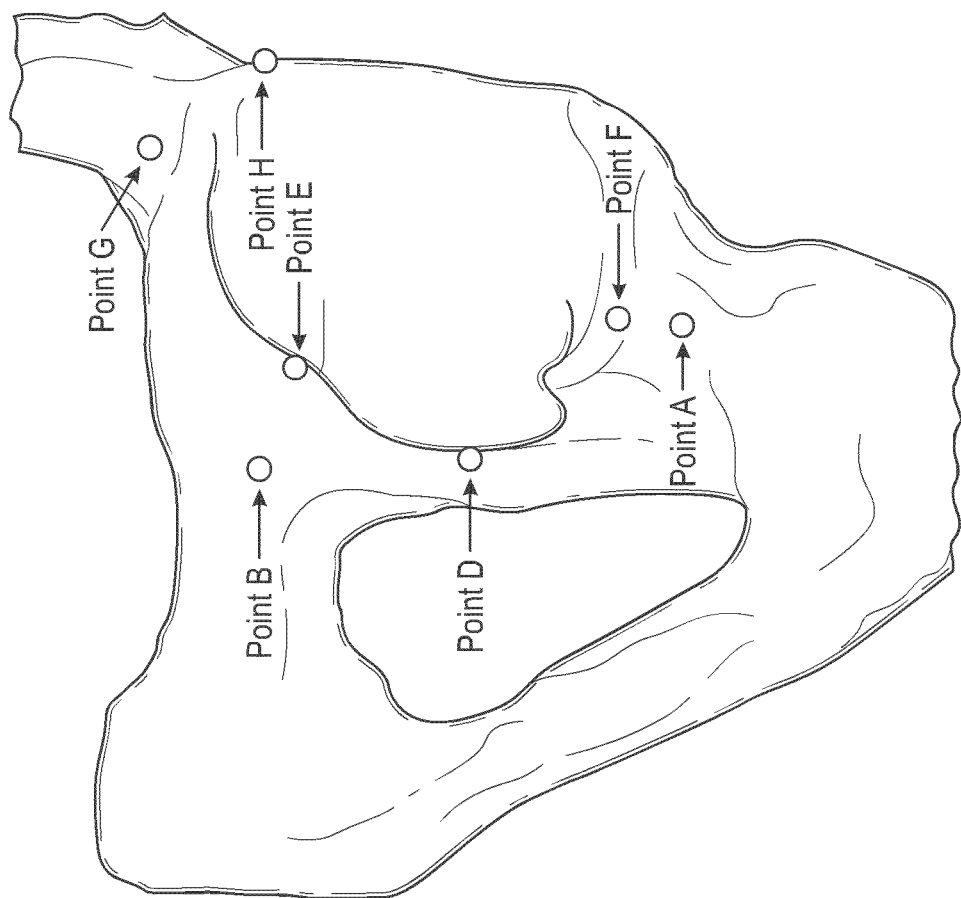
FIG. 2 is an image of hip anatomy illustrating some examples of anatomical landmarks that can be used in a method of navigating a hip prosthesis with the navigation system of FIG. 1.

As discussed further below, the cannula 124 can be coupled with other bones in other techniques with a posterior approach. For example, the cannula 124 can be coupled with the ischium or the pubis in other techniques. In some techniques, the cannula 124 is mounted to a pelvic bone but not at a landmark. The hip navigation system 450 discussed below in connection with FIG. 17-17B can be used such that the fixation member 466 is coupled at a point superior to the superior-most point on the acetabular rim. In a specific technique, the member 466 is about 10 mm above the superior-most point on the acetabular rim. In such techniques, three or more anatomical landmarks disposed about the acetabulum can be acquired, as discussed below. When the cannula 124 is coupled with a landmark, only two additional landmarks are acquired in some embodiments as discussed below. In another variation, a clamp can be used to couple with a bone without requiring that the pin 132 be driven through the cannula 124 into the bone. For example, if the bone is thinner in the region where the system 100 is to be anchored, placing the pin may be disadvantageous. FIG. 2 shows a region where a clamp may be used beneath the point "A" on the ischium. One reason for mounting or clamping the cannula 124 away from the landmarks is that the landmarks may not be visible or accessible before dislocating the hip joint. If the clinician wishes to use the system 100 to reference the femur (as discussed below), it may be required to mount or clamp the cannula 124 away from the landmarks.

FIG. 1 illustrates a step toward the end of a navigated hip joint implant procedure discussed in detail below. Some of the preceding steps involve removing the to-be-replaced joint, navigating the hip joint, preparing the implant location for the artificial joint, and placing the joint, as elaborated below. As discussed further below, FIG. 1 illustrates a technique for confirming that these steps were properly performed.

FIG. 2 shows some of the anatomy that is relevant to various methods and systems herein. In some embodiments, the navigation system 100 is configured to locate a relevant anatomical feature to aid in proper placement of a prosthetic hip joint. For example, a plane can be located using the system 100 that includes at least a portion of a patient's acetabular rim. In practice, the acetabular rim may be uneven due to development of ostephytes. So, in the context of this application locating the anatomical plane can be an approximation of the actual topography, for example an estimate of the plane, a plane including a substantial fraction, e.g., a majority of the surface of the acetabular rim, or some other manner of estimating a relevant anatomical feature. Preferably the anatomical landmark being located is used to confirm accurate placement of at least the cup and preferably the complete artificial hip joint.

FIG. 2 also shows an example of anatomical landmarks that can be used to approximate the acetabular rim or another plane relevant anatomical landmark. In many patients the acetabular rim is not well defined, due to injury, advanced stages of arthritis or other conditions. Accordingly, approximating the acetabular rim for these patients includes calculating in the system 100 a plane that references but may not include most or any of the actual acetabular rim. The plane that is defined is located near the rim but more importantly has a known anteversion and abduction angle relative to the anterior pelvic plane. For example, three points can be used to estimate the plane of the acetabular rim. In one technique, some or all of the points illustrated in FIG. 2 are used.

Figure 34:
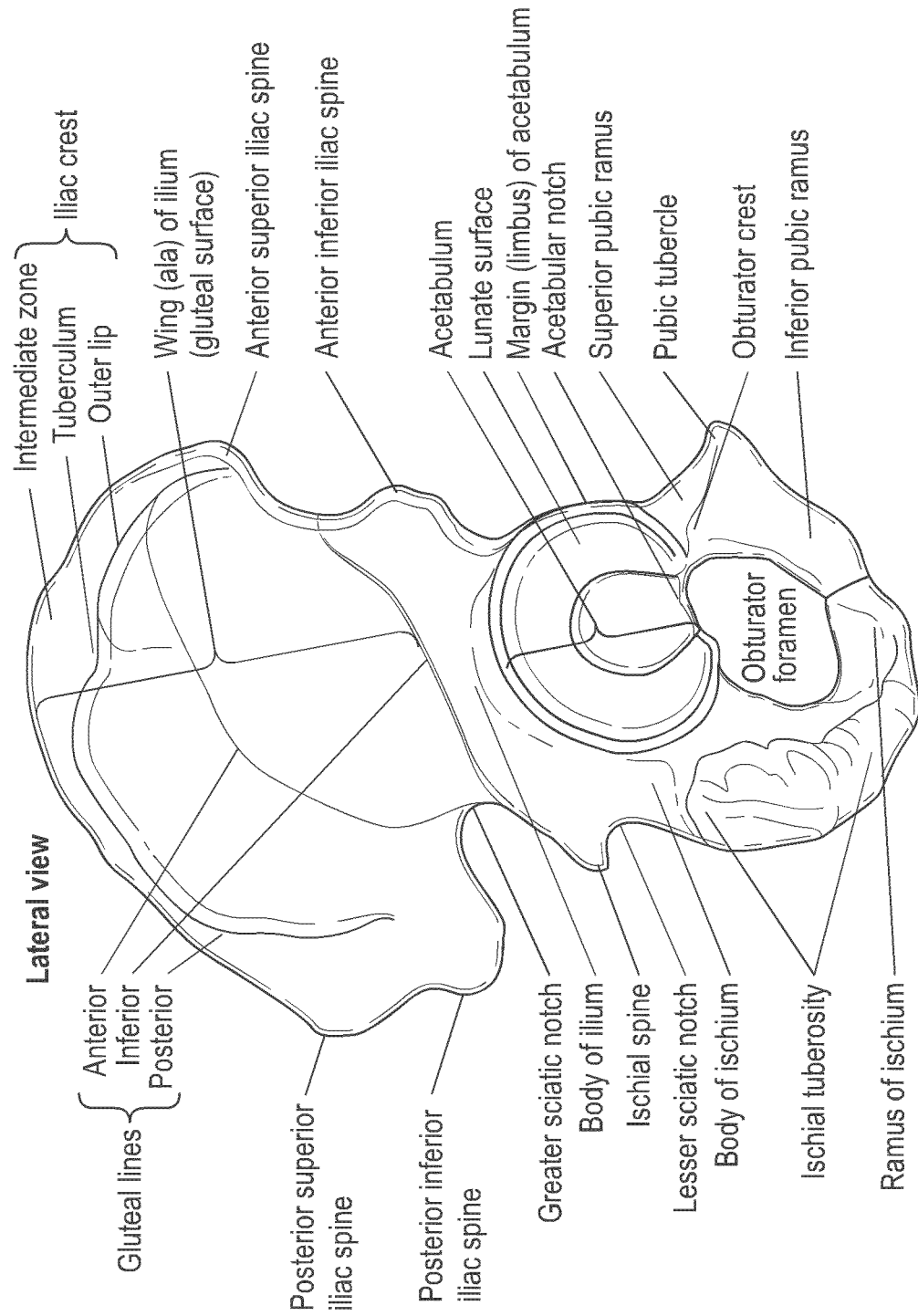
FIGS. 34-35 illustrate various anatomical landmarks that can be used in various methods involving navigating with landmarks.
Figure 35:
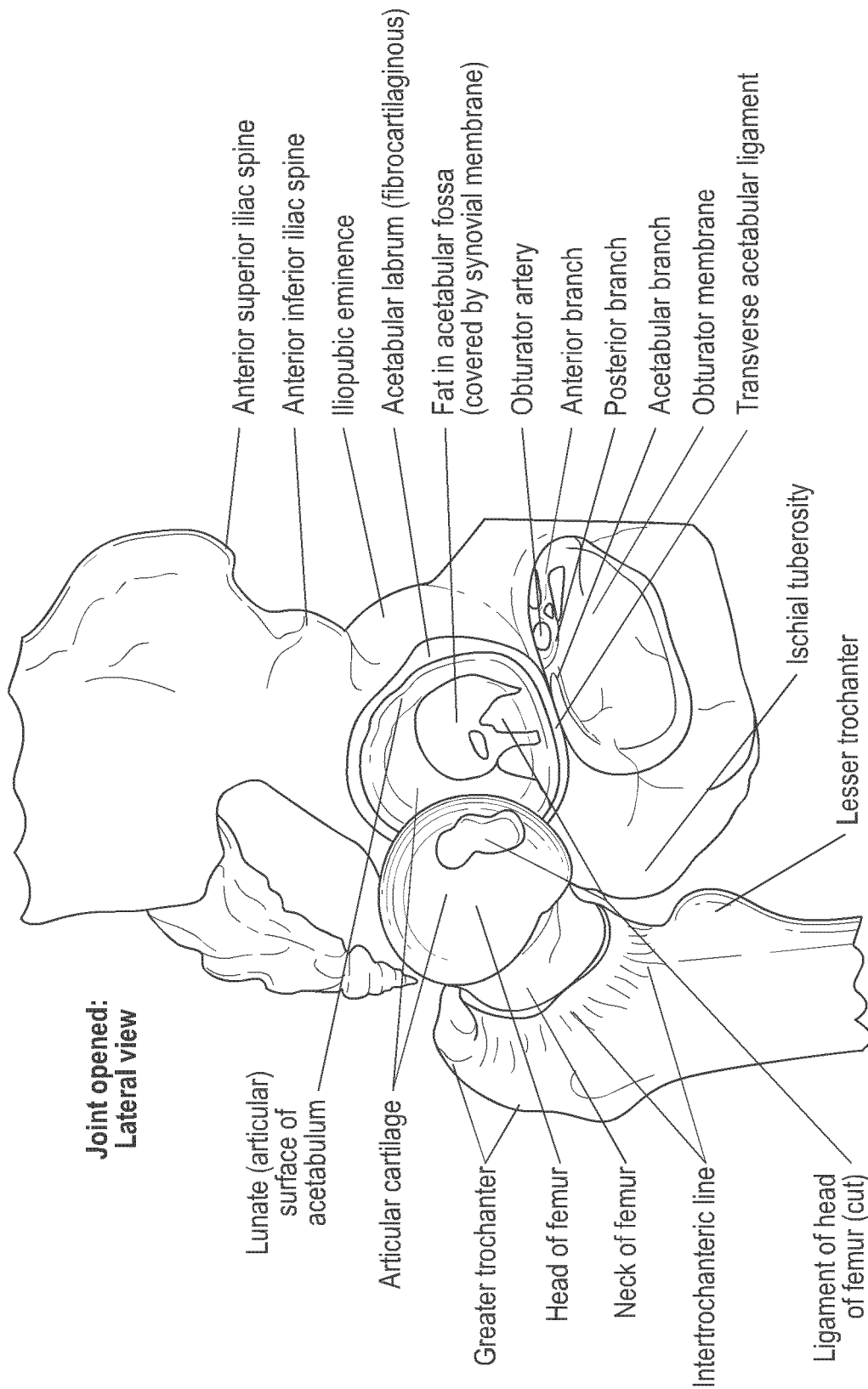

As illustrated by FIG. 2, three landmarks are defined at "A", "B", and "H". The landmark "H" is located on the ilium at a location that is spaced away from the rim by an amount sufficient to avoid irregular bony growth due to injury, advanced stages of arthritis or other conditions, for example 1 cm superior to the most superior point on the acetabular rim. The landmarks "A" and "B" can be located on the ischium and pubis respectively and can be similarly spaced from the rim to avoid damaged/diseased areas. Each of these landmarks preferably is close enough to the rim, however, to be within the standard open area, e.g., the area exposed by the surgical cut down. Other landmarks that could be used include: anterior insertion point of trans-acetabular ligament to the ischium, mid-point of the inferior aspect of the acetabular notch, the anterior superior iliac spine, anterior inferior iliac spine, convergence of the acetabulum and anterior inferior iliac spine, as well as the other landmarks illustrate on FIGS. 34 and 35. In the techniques discussed below all of the ilium, the pubis, and the ischium are used to locate the acetabular rim. The navigation system 100 has one or more processors that receive(s) data and determines the relative position of these (or other) anatomical landmarks from these points. The data can be generated by inertial sensors, as discussed elsewhere herein, or other types of sensors. Preferably the sensors are small enough to be mounted on or in handheld housings or embedded in the instruments. The navigation system 100 preferably also has a memory device to at least temporarily store the position of these points or relevant orientation data.

Figure 3:
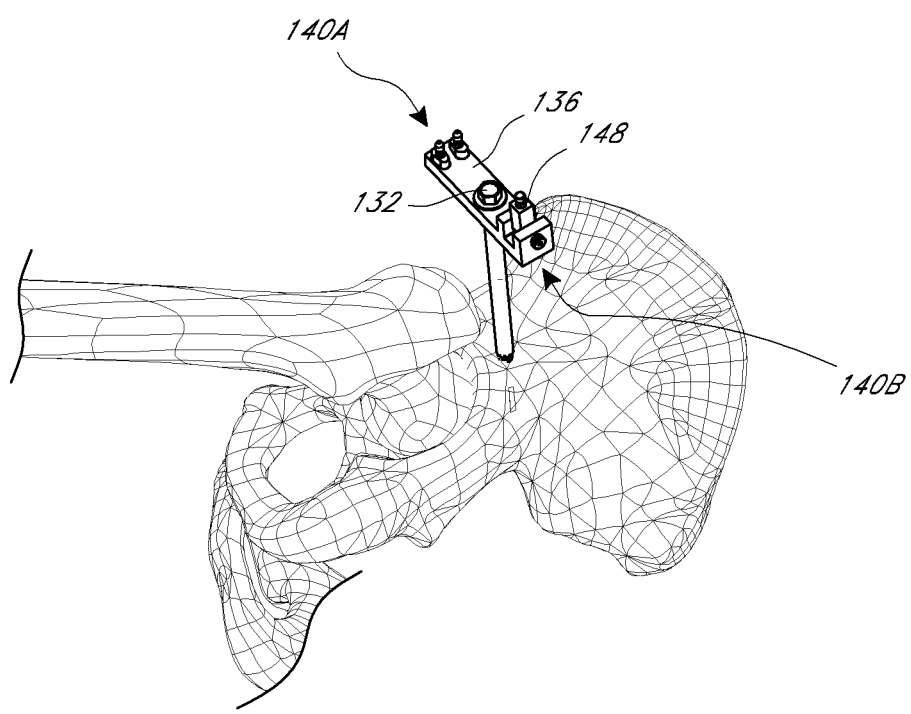
FIG. 3 shows a navigation base assembly coupled with a first anatomical landmark, in this case the ilium on the pelvis of the patient.

FIG. 3 shows further details of the registration jig 104 and further aspects of methods of navigating an artificial hip joint. A proximal end of the pin 132 is coupled with or disposed above a platform 136 that is configured to couple with the alignment assembly 108 and/or the landmark acquisition assembly 112. As shown in FIG. 1, the platform 136 can be connected to both of the alignment assembly 108 and the landmark acquisition assembly 112 at the same time. The platform 136 comprises a rigid bar fixed to the proximal end of the pin 132 and/or the cannula 124 in the illustrated embodiment. The platform 136 includes a plurality of mount features 140A, 140B, e.g., a mount feature on each of two lateral ends 144A, 144B of the platform. The mount feature 140A is configured to permit non-rotational attachment to the alignment assembly 108.

Figure 5:
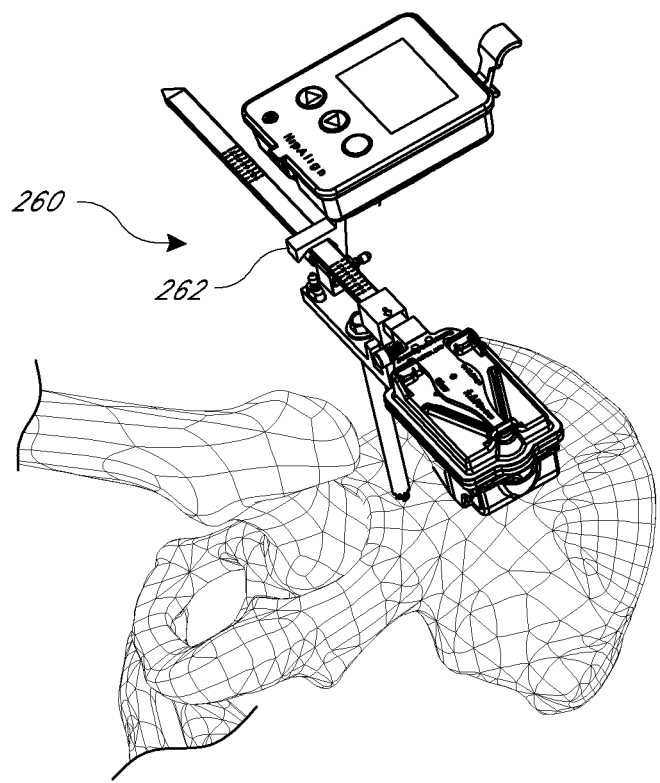
FIG. 5 is a perspective view of the navigating system, illustrating one technique for synchronizing a plurality of orientation and/or position detecting devices of the navigating system of FIG. 1.

FIG. 3 illustrates that the registration jig 104 is configured to be used in left and right hip procedures, for example having a dedicated mount feature 140A for each hip. Preferably the mount feature 140A provides a post spaced away from the joint being treated so that the alignment assembly 108 can be mounted as far away from the hip joint as possible. FIG. 5 shows the alignment assembly 108 on this post and another post exposed. The exposed post is not used during the procedure on the hip joint illustrated in FIG. 5. However, if the other hip of the patient is being treated, the platform 136 is in the opposite orientation and the posted exposed in FIG. 5 will be coupled with the alignment assembly 108. Stated another way, a longitudinal axis of the platform 136 extends between two mount posts, each of which can be dedicated to a hip on one side of the medial-lateral mid-plane of the patient.

The mount feature 140B enables rotational mounting of the landmark acquisition assembly 112. For example, the mount feature 140B can include a pivotally mounted jig 148 that projects upward to a free end that is adapted to mate with an orientation sensing device as discussed below. The joint 148 permits a registration arm, such as the elongate member 224 discussed below to be tilted downward to touch landmarks at different elevations.

In one technique, the registration jig 104 is preassembled and is driven into a suitable anatomical landmark, such as the ilium. In other techniques, an anchor jig can be mounted off-set from a landmark to be acquired. The ilium will have been previously identified by conventional means, such as by X-ray examination, palpation, or by making an incision and visually inspecting the pelvis. In one technique, the cannula 124, the pin 132, and the platform 136 are separable so that the pin can be placed and the platform 136 coupled to the pin at a later time. The cannula 124 can be coupled with other landmarks in some variations.

FIG. 4 illustrates further steps of various techniques. For example, the alignment assembly 108 can be coupled with the mount feature 140A. In one embodiment, the alignment assembly 108 includes a rigid extension 160 that is adapted to be mounted detachably to the mount feature 140A. The extension 160 has a first end 164 and a second end 168. The second end 168 is detachably mountable to a surgical orientation device 172 that detects orientation and rotation of the device 172 relative to a reference frame. The orientation device 172 preferably comprises at least one sourceless sensor, such as an accelerometer, a gyroscope, or a combination of these sensors and other sensors. In one preferred embodiment, the orientation device includes a three axis accelerometer to detect orientation relative to gravity and a plurality of gyroscopes to detect rotation. Other sensors could be used in various modifications. Examples of specific sensor combinations include Analog Devices ADIS 16445 and Invensense MPU-6050 or MPU-9150 among others. In some approaches, the orientation device 172 can be disposable and so the sensors preferably are less expensive sensors. Sensors on the landmark acquisition assembly 112 may be reusable in some configurations and thus may incorporate more expensive, more rugged or more accurate sensors.

The first end 164 of the detachable extension provides several functions. The first end 164 has a device to engage the mount 140A in a secure but releasable manner. The engagement between the extension 160 and the platform 136 minimizes or prevents relative movement therebetween to avoid any mechanical relative movement during navigation procedures so that movement of the orientation device 172 corresponds to movement of the hip. The first end 164 also has a docking device that, as discussed further below, provides a stable and controlled manner to position the landmark acquisition assembly 112 relative to the orientation device 172.

FIG. 4 also illustrates that the landmark acquisition assembly 112 can be securely coupled to the platform 136, e.g., at the mount 140B. In one embodiment, the landmark acquisition assembly 112 includes a gimbaled jig 200 and an orientation sensing device 204. The jig 200 includes a coupler 208 for detachably coupling with the mount feature 140B of the platform 136. The coupler 208 is pivotally connected to a sliding support 212. The sliding support 212 includes a slot that permits slideable extension of an elongate member 224. The slideable extension permits a range of motion of a distal end 228 of the elongate member to facilitate acquiring a plurality of landmarks that are different distances from the attachment location of the cannula 124, as discussed further below. In other words, the distal end 228 can be extended away from the axis of the sliding support 212 or can be retracted to a position closer to the axis of the sliding support 212.

Figure 6:
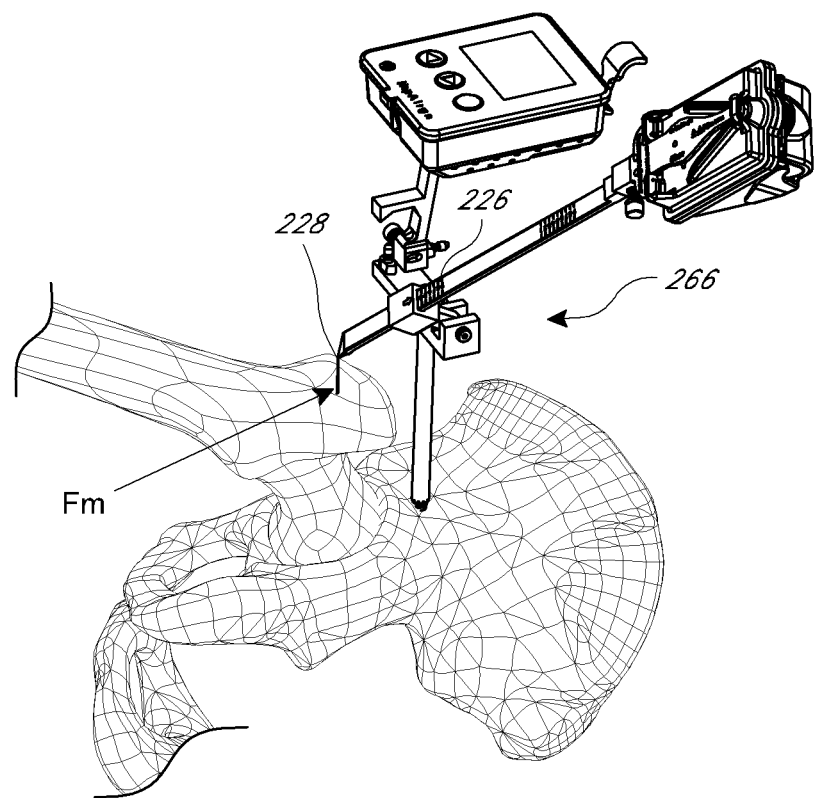
FIG. 6 is a perspective view of the navigation system of FIG. 1 coupled with the pelvis and illustrating a step of registering a landmark of a femur prior to resecting the femur.

FIGS. 4 and 6 illustrate the moveability of the landmark acquisition assembly 112 relative to the platform 136 between two positions. In FIG. 4, the elongate member 224 is swung about an axis that may be parallel to a longitudinal axis of the cannula 124 to move the distal end 228 away from the first end 164 of the extension 160. This is a moving configuration of the gimbaled jig 200. In addition to rotation enabled by the pivotal coupling between the coupler 208 and sliding support 212, the pivotally mounted joint 148 can enable the elongate member 224 to pivot about an axis that is not parallel to the axis of the cannula 124. The axis of rotation of the joint 148 can be perpendicular to the axis of rotation of the sliding support 212. This rotatability enables the distal end 228 of the elongate member 224 to pivot down to contact anatomical landmarks, as discussed above. Additionally, the slideability of the elongate member 224 within the sliding support 212, discussed above, enables the distal end 228 to move to reach anatomical landmarks in the same plane but closer to or farther from the distal end of the cannula 124 or pin 132. FIG. 6 shows the distal end 228 of the elongate member 224 positioned closer to the platform 136 for referencing landmarks at higher elevation or closer positions, e.g. on the lateral side of the femur.

FIG. 4 also shows that the distal end 228 can include an angled length that enables the elongate member 224 to avoid minor irregularities in height adjacent to the anatomical landmarks being registered. Such irregularities may be normal anatomy, osteophytes or irregular bone growth of various types.

FIG. 5 illustrates a parked configuration 260 of the landmark acquisition assembly 112. In particular, a portion of the elongate member 224 is moved into a latch 262 disposed at the first end 164 of the upright extension 160. The parked configuration 260 enables the navigation system 100 to manage errors that can compound in some inertial sensors. For example, in one embodiment, gyroscopic sensors in the orientation device 172 and in the orientation sensing device 204 can be synchronized when a stable and known orientation is detected and one or more of the gyroscopes, e.g., the gyroscope in the device 204, can be zeroed after that condition is met. Further techniques employing the parked configuration 260 will be discussed further below. As discussed below in connection with the system 450, some jigs have a registration point adjacent to the distal end of the anchor jig or bone connection site. The system 450 is capable of accurately acquiring landmarks based on only accelerometers operating in the device 204 in one mode. In such a mode, a registration feature can provide an analogous function to the parked configuration, e.g., to enhance accuracy of the sensing devices in the system.

Another example of a parked configuration of the system 100 can be provided. For example, the parked configuration advantageously includes the ability to stably position and hold the devices 172, 204 for substantially no relative movement. In one approach, the orientation sensing device 204 is mounted on the rigid extension 160. Other arrangements could include a mounting post on the platform 136 adjacent to the rigid extension 160.

Where error management is less an issue, the parked configuration 260 can still be useful in that it prevents unwanted swinging or other movement in the surgical field.

In one basic method, the jigs discussed above are connected to the pelvic bone, the system 100 is put into the parked configuration 260, and the sensors are initialized. The initializing can include synchronizing at least two sensors. In some cases, the initializing can include zeroing one or more sensors. In this context, "zeroing" is a broad term that includes any method of eliminating accumulated error in the system, including any form of resetting of the sensors, and/or confirming in one device that the data from the other device is reliable for at least a fixed period.

FIG. 6 illustrates an optional step of acquiring a landmark of a femur in connection with a hip replacement procedure. The hip is positioned in a neutral flexion/abduction position. The landmark acquisition assembly 112 is in a withdrawn configuration 266 with the elongate member 224 moved, such as by sliding in the sliding support 212, to accommodate the relatively short distance from the platform 136 and a landmark of the proximal femur. In one technique the tip of the distal end 228 is brought into contact with a part of the greater trochanter or elsewhere on the proximal femur. After the landmark is found and/or contacted, the clinician can make a mark on the femur Fm, such as a bovie mark, a pen mark, a stitch or other durable indication. Once the tip of the distal end 228 is in contact with the desired landmark, the navigation system 100 processes data from and stores the orientation of one or more sensor(s) in the orientation sensing device 204. Additionally, in some embodiments, the elongate member 224 is provided with a scale 226 indicating position of the tip of the elongate member 224, e.g., relative to the cannula 124 or some other relevant fixed feature of the patient or the system 100. By providing the scale 226 to be read by the clinician, the system is made simple and cost effective.

After the optional step illustrated in FIG. 6, the proximal femur can be resected to remove the natural ball thereon.

Figure 7:
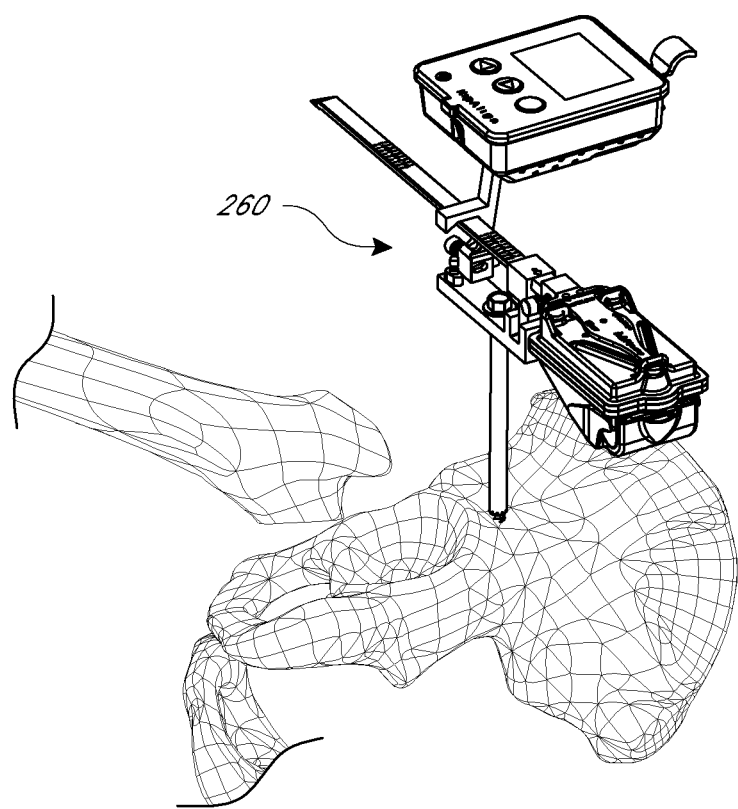
FIG. 7 shows the anatomy after the femoral head has been resected and an optional step of synchronizing a plurality of inertial sensors of the navigation system.

FIG. 7 illustrates that in one advantageous technique, the user returns the system 100 to the parked configuration 260. This step may be optional depending on the sensor(s) and the timing of the resecting of the femur. In this position, the sensor(s) in the orientation devices 172, 204 can be initialized again, e.g., zeroed. As discussed above, this is one technique for minimizing accumulation of error in some inertial sensors. By providing this optional step, less costly sensors can be used enabling the system 100 to deliver highly accurate hip replacement while helping to manage cost for the patient, medical provider and healthcare system generally.

Figure 8:
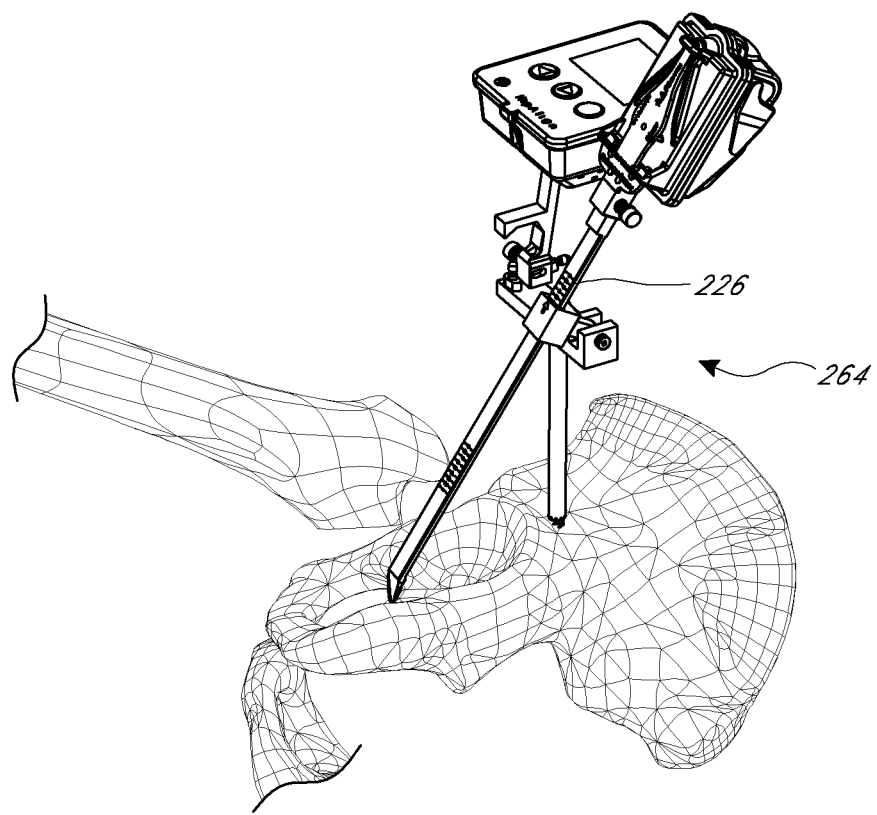
FIG. 8 illustrates a step of registering an anatomical landmark disposed about the acetabular rim on the pelvis.

FIG. 8 illustrates a first extended configuration 264 provided in a step after the resecting of the proximal femur in which a second anatomical landmark is acquired or referenced. In particular, the elongate member 224 can be extended and can be rotated by the jigs 148, 200 to be in contact with any suitable landmark. In one technique, contact is made between the distal end 228 and the ischium. To provide maximum accuracy, this contact may be provided within a short period, e.g., within about 20 seconds of being disengaged from the parked configuration 260. Once contact is made, the system 100 is configured to store the orientation of the sensing device 204. In one configuration, the orientation is stored after a button or other indirect means is pressed on the orientation device 172. In addition to acquiring the orientation, a position value is input to the system. For example, the scale 226 on the elongate member 224 can be read by the user and the value of the scale input into the system. In one technique where the scale 226 is read and input by the user, the orientation device 172 has a user interface with an input device for inputting such variables. As can be seen in the drawings, the scale 226 can in fact be two different scales, one for each of the retracted configuration 266 and the extended configuration 264. Alternatively, the scale 226 can extend the entire length of the elongate member 224 to provide a greater range of positions that can be read by the clinician or by the system as in FIGS. 13 and 14.

The extended configuration 264 is one in which the distal end 228 of the elongate member 224 is adapted to touch an anatomical landmark located between the medial cephalad-caudal plane of the patient and the acetabulum of the pelvis.

Depending on the sensors used and the timing of landmark acquiring step of FIG. 8, the user may return the system 100 to the parked configuration 260 and also may initialize, e.g., zero, the system 100 again.

Figure 9:
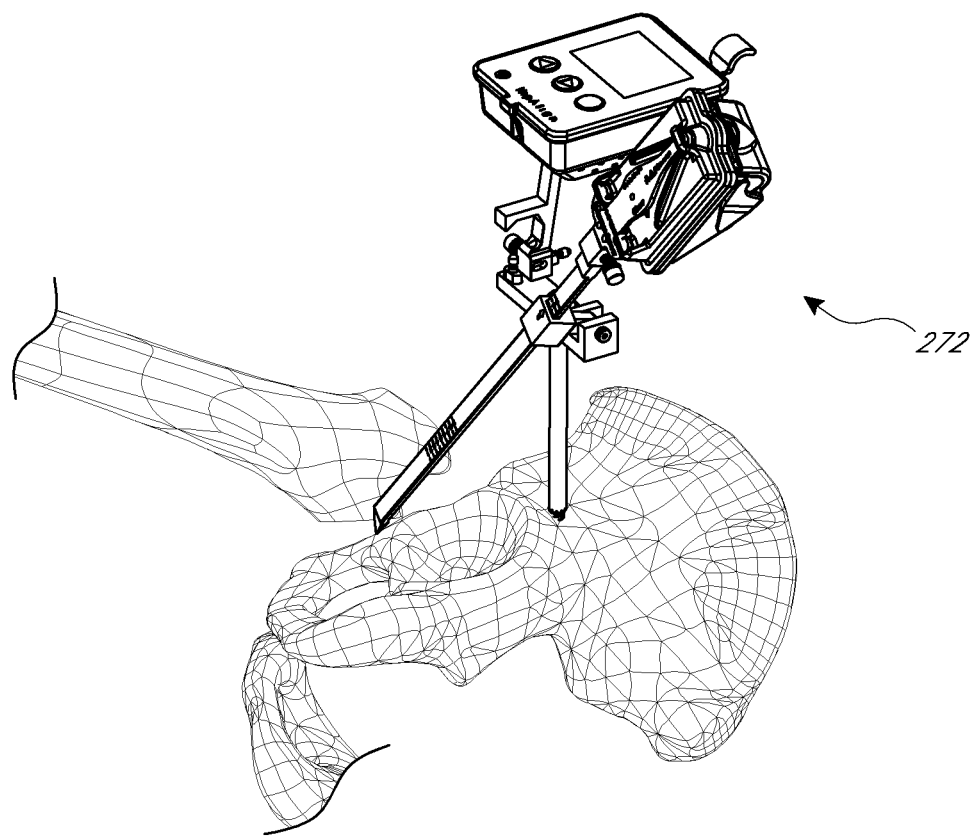
FIG. 9 illustrates a step of registering another anatomical landmark disposed about the acetabular rim of the pelvis.

FIG. 9 illustrates a second extended configuration 272 provided in a step after the resecting of the proximal femur in which a third anatomical landmark is acquired or referenced. The third anatomical landmark can be acquired before the second anatomical landmark in some techniques. In the second extended configuration the distal end 228 of the elongate member 224 moved to contact a landmark, such as the pubis. To provide maximum accuracy, this contact may be provided within a short period, e.g., within about 20 seconds of being disengaged from the parked configuration 260. Once contact is made, the system 100 can store the orientation of the sensing device 204. The orientation can be stored by pushing a button or other user interface device. In some techniques orientation and position are input into the system. For example, the scale 226 on the elongate member 224 can be read by the user and the value of the scale input into the system. In one technique where the scale is read and input by the user, the orientation device 172 has an input device, such as a user interface for inputting such variables.

The extended configuration 272 is one in which the distal end 228 of the elongate member 224 is adapted to touch an anatomical landmark located anteriorly of the acetabulum.

Once landmarks have been acquired, the system 100 can determine the bearing of three landmarks including that of the attachment location of the cannula 124, if the pin is attached to a relevant landmark. The system can calculate the orientation of the orientation device 172 relative the plane containing these three (or in other methods another group of three or more) landmarks. From this, a variety of post processing can be performed. For example, the orientation (anteversion and/or abduction) can be adjusted based on the known mean orientation of the plane containing these three (or another three or more, if used) landmarks from the pelvic anatomic reference planes.

One variant of the system 100 enables a user to select between multiple sets of landmarks for use in the above calculations. The method discussed above exploits the use of three points that are off of the acetabular rim. These points are less impacted by local prominences at the rim that may be due to disease or deformity. Thus, they have a lower likelihood of requiring intra-operative improvisation. On the other hand, another set of landmarks can be selected where the rim is free of deformities, which might be confirmed pre-operatively. For example, two or three points can be selected on the acetabular rim for landmark acquisition. The on-rim landmarks are advantageous in that they are easier to access through a smaller incision. For example, on-rim points can include the center of the posterior insertion of the transacetabular ligament, the center of the anterior insertion of the transacetabular ligament and the most superior point on the rim. A group of anatomical landmarks including one or more extra-acetabular landmarks can include the ilium (where the registration jig 104 or other anchor member can be inserted), the lowest point of the acetabular sulcus of the ischium, and the prominence of the superior pelvis ramus.

Some techniques involve referencing a fourth point. The fourth point can be used in connection with some forms of patient specific registration. The fourth point can be extra-acetabular or can be disposed on the acetabular rim. An example of an acetabular landmark is the acetabular notch. Other landmarks are discussed herein, for example in connection with FIGS. 34 and 35.

The posterior approach systems are advantageously configured to allow intra-operative selection between on-rim and off-rim points. For example, if the rim looks free of deformities pre-operatively but when exposed presents differently, the surgeon can select an off-rim landmark set.

Several techniques for enhancing the accuracy of the relationship between the sensed landmarks and the location of calculated anatomical features, such as the anterior pelvic plane or angle of the acetabulum can be employed. For example, user input can be collected indicating whether the hip being treated is on the left or the right side of the patient and whether the patient is male or female. A more refined estimation of the model can be provided based on a characterization of a study group. For example, hip joints of a group of 30 or more patients can be studied to identify the correspondence between a feature that can be accessed in one approach and an anatomical feature of more surgical relevance that cannot. A group of subjects can be studied for any number of demographic characteristics such as gender, age, weight, height or any other variable in a relevant population. For those sub-groups, a correlation or transformation between a measured parameter and a parameter that cannot be measured but is desirable to know can be generated. Once such a correlation or transformation is established, transforming a measured feature into the unmeasurable but useful to have feature can be achieved by operating software on a processor. The software can be programmed to calculate one or two angles, e.g., inclination and anteversion based on a registered pelvic plane, such as a proxy acetabular plane. Such a system can be used to generate in real time the angles of a free hand instrument relative to the anatomy, e.g., relative to an acetabulum in placing a hip socket component.

Additionally, data from the use of pre-operative imaging or positioning (discussed below) can be used to enhance the accuracy of these calculations. Thus, the posterior approach systems preferably are configured to take user input directly by actuating buttons on the orientation device 172 or by connecting an auxiliary data storage device, such as a flash memory device, to the system or by any means of other communication with the system, including wifi connection, Bluetooth, Internet connection among others.

In some techniques, the posterior approach systems described herein are adapted to determine, monitor, and confirm proper leg length and joint offset outcome in a hip replacement. For example, the system 100 can calculate and store components of a leg length metric, e.g., a vector along the superior-inferior axis (leg length) and/or along the medial-lateral axis (offset). In one approach, the device 172 has a display that indicates when the femur is in the same position pre- and post-operatively. For example, it can indicate "0" meaning no displacement causing a leg length change and "0" indicating no movement of the femur farther away from the cephalad-caudal mid-plane of the patient pre- and post-operatively. For enhanced accuracy, a plurality of points, e.g., three points, can be marked acquired and/or marked on the femur. The points can be spaced apart by an amount sufficient to provide increased accuracy. These three points can be used to confirm proper placement of the femur in abduction, rotation, and flexion.

One enhancement involves referencing the femoral neck to assure that after implanting the hip joint, the femur is positioned properly rotationally. For example, it may be desired to make sure that a feature of the femur like the greater trochanter resides in the same rotational orientation relative to an axis extending through the center of rotation of the femoral head and perpendicular to the plane of the acetabulum. To assure a substantially unchanged rotation orientation post-implantation, the system 100 can record one or more, e.g., three points on the femoral neck pre- and post-implantation. Three points that would be convenient from either the posterior approach or the anterior approach (discussed below in connection with FIGS. 18-21) are the greater trochanter, lesser trochanter and the insertion of the obdurator externus.

The foregoing are some steps that can be used to determine and store a variety of parameters useful in a navigated hip procedures. After some or all of these steps have been performed, in one embodiment, the acetabulum can be prepared for receiving a cup. For example, the acetabulum can be reamed in a conventional manner. In some embodiments, the reamer can be coupled with an orientation device containing an inertial sensor to guide the reaming process. This is discussed in some detail in US2010/0076505, published march 25, 2010 which is incorporated by reference herein in its entirety for this purpose and for all disclosure therein generally.

Figure 10:
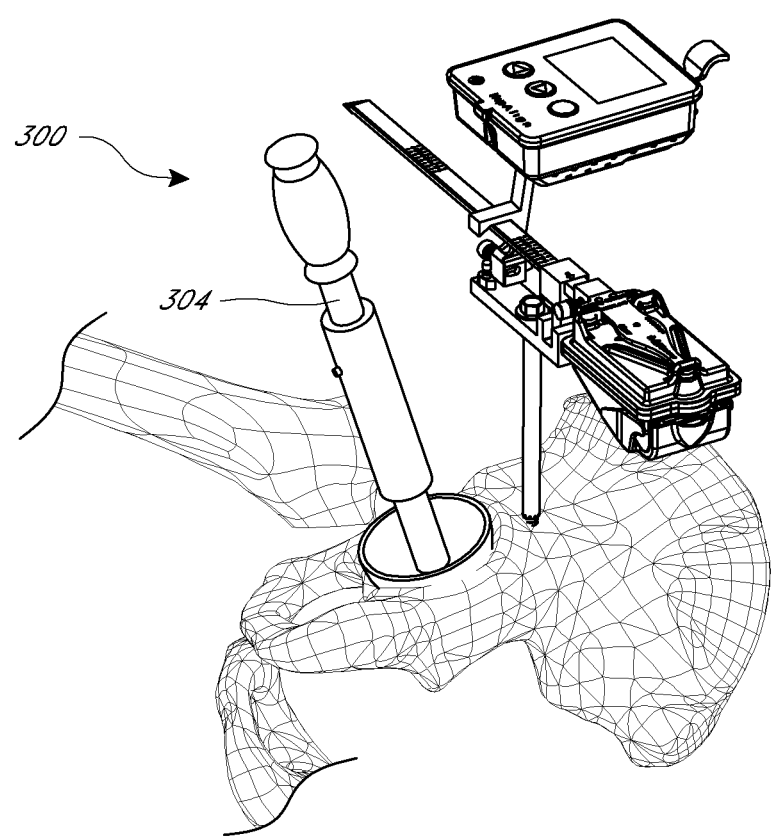
FIG. 10 illustrates initial placement of an impactor in the acetabulum.

FIG. 10 shows that after reaming, an impactor 300 may be used to place a cup of an artificial hip joint. The impactor handle 304 may be positioned in the approximate correct orientation, e.g., with a longitudinal axis of the impactor being disposed perpendicular to the plane navigated above or a plane determined based on the navigated plane. FIG. 10 shows that this initial placement can be done while the system 100 is in the park configuration 260. The impactor 300 can be substantially aligned at this time, based on visual inspection. As part of the step illustrated in FIG. 10 or shortly thereafter, the sensors can be initialized, e.g., zeroed as discussed above.

Figure 11:
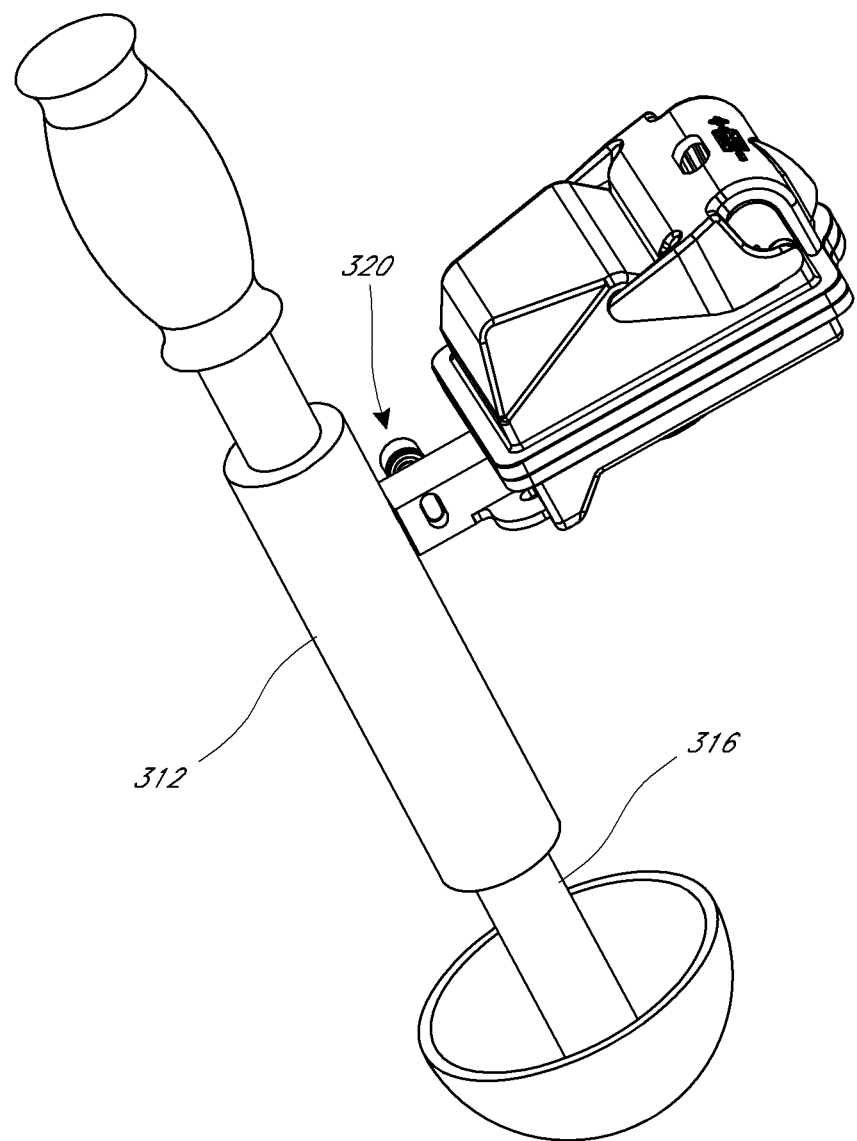
FIG. 11 illustrates a hip prosthesis placement system, including an inertial sensing device.

FIG. 11 shows that in a subsequent step the orientation sensing device 204 can be undocked from the proximal end 230 of the elongate member 224 and thereafter docked to the impactor 300. Preferably this step is performed while the impactor 300 is in place on the hip, close the proper alignment. In another embodiment, a third sensing device similar to the sensing device 204 be coupled with, e.g., pre-attached to, the impactor and the data collected above transferred to the third device. The impactor 300 and sensing device 204 comprise a cup orientation navigation assembly. Preferably the impactor 300 has a cylindrical shell 312 that is moveable relative to an inner shaft 316 of the handle 304. The shell has a docking device 320 that can receive the docking device of the sending device 204. The moveability of the shell 312 helps to isolate the sensing device 204 from the forces that are transmitted through the impactor 300. These forces are applied by a mallet or other device for forcibly moving the cup into position. By providing at least some force isolation between the shell 312 and the sensing device, impact on the sensors in the sensing device 204 can be reduced. Excessive force being applied to the sensing device 204 can put the device 204 out of service, for example until synched with the device 172.

Figure 11A:
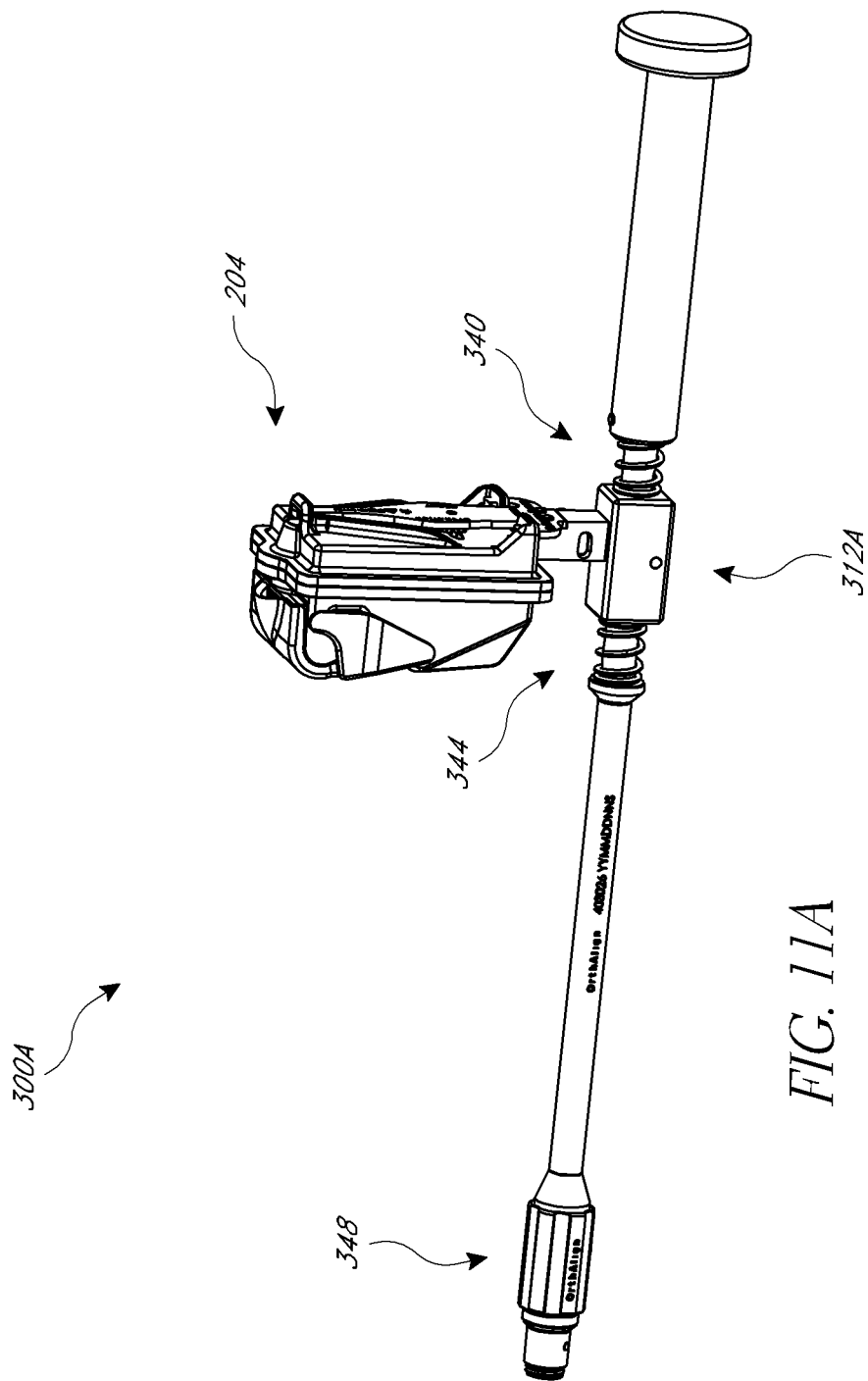
FIGS. 11A-11C illustrate an embodiment of an impactor assembly.

FIG. 11A illustrates a further embodiment of an impactor 300A in which the movement of a shell 312A is cushioned by a plurality of spring members 340, 344 which are configured to absorb at lease some of the shock of the impact on the impactor 300A. The impactor 300A also is configured to be modified to suit any of a plurality of hip prostheses. For example, a plurality of tip components 348 can be provided in a kit where each tip component is attachable to and detachable from a distal end of the shaft 316A of the impactor 300A.

Figure 11B:
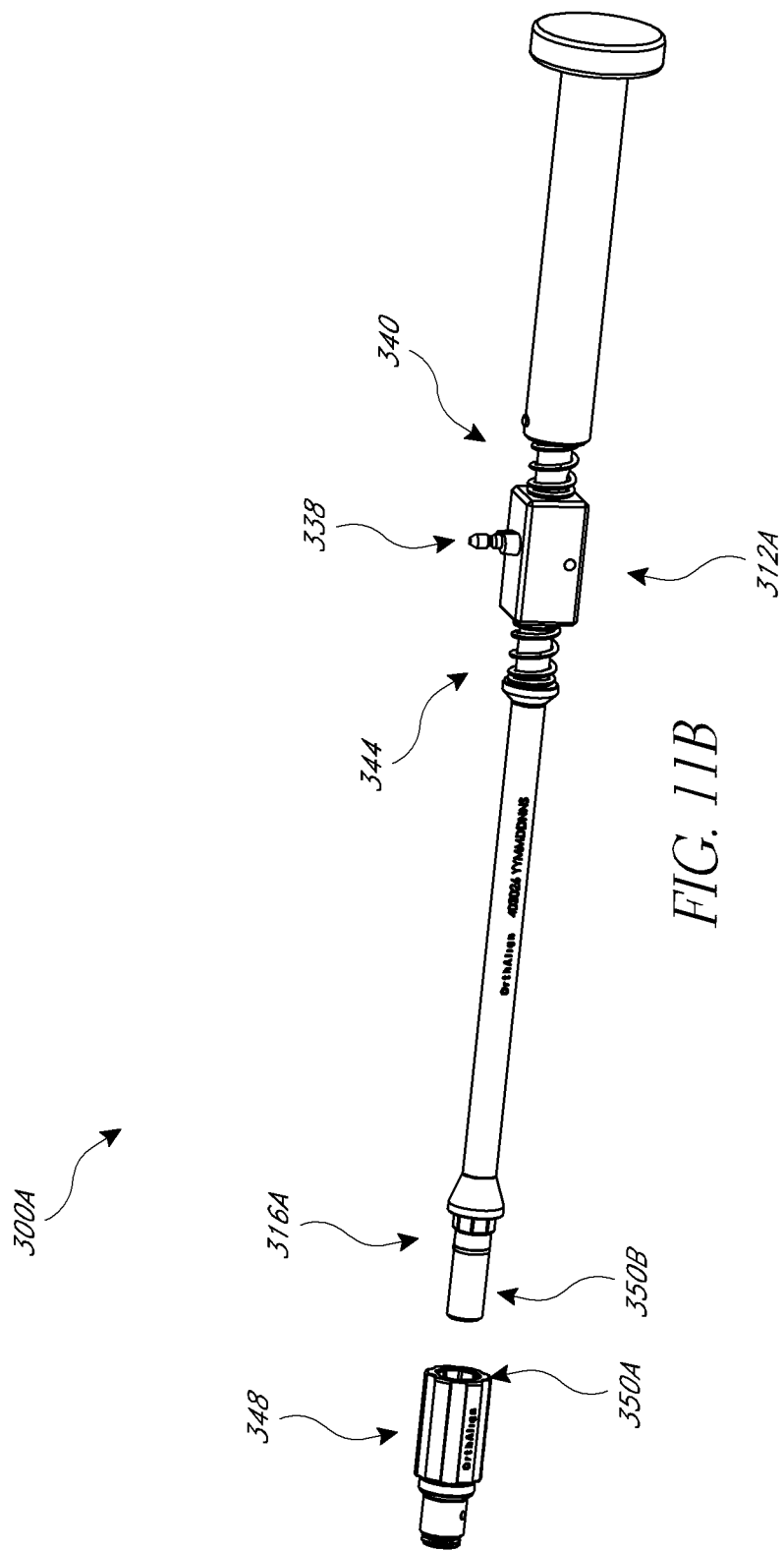
Figure 11C:
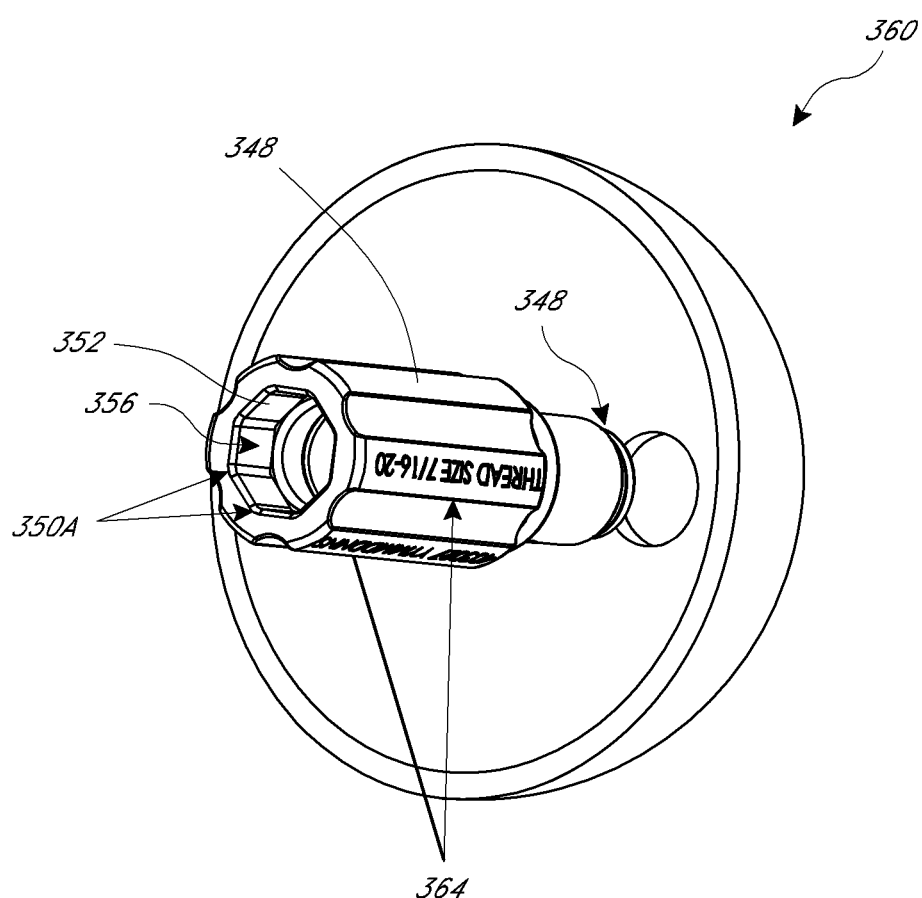

FIGS. 11B-C show more detail of distal features of the impactor 300A. In particular, the tip component 348 is removable from a shaft 316A of the impactor 300A. FIG. 11C shows that the tip component 348 can have a recess 352 formed on the proximal side thereof and an engagement device 356 formed on the distal side thereof. The recess 352 can comprises a plurality of flats 350A corresponding to a plurality of flats 350B on the distal end of the shaft 316A. The flats permit proximal-distal sliding of the recess 352 over the distal end of the shaft 316A. Preferably a detent device or other mechanism is provided between the tip component 348 and the shaft 316A so that the component does not fall off the shaft. The flats prevent the tip components 348 from rotating relative to the shaft 316A. The engagement device 356 comprises threads in one embodiment so that the cup 360 of the prosthetic hip can be screwed onto the distal end of the tip component 348. The sliding engagement of the tip component 348 on the shaft 316A is important because the impactor 300A is intended to be used with hip prostheses of a variety of manufacturers. Often the cup 360 will have a hole pattern for securing the cup to the prepared acetabulum that is unique to the manufacturer and that is dictated by the anatomy. The flats enable many discrete alternate relative angular positions of the tip component 348 (and hence the cup 360) to the shaft 316A. A plurality of flutes or elongate axial ridges 364 on the outer surface of the tip component 348 enable the user to securely grasp the tip component for mounting and dismounting the tip component on the shaft 316A.

Figure 12:
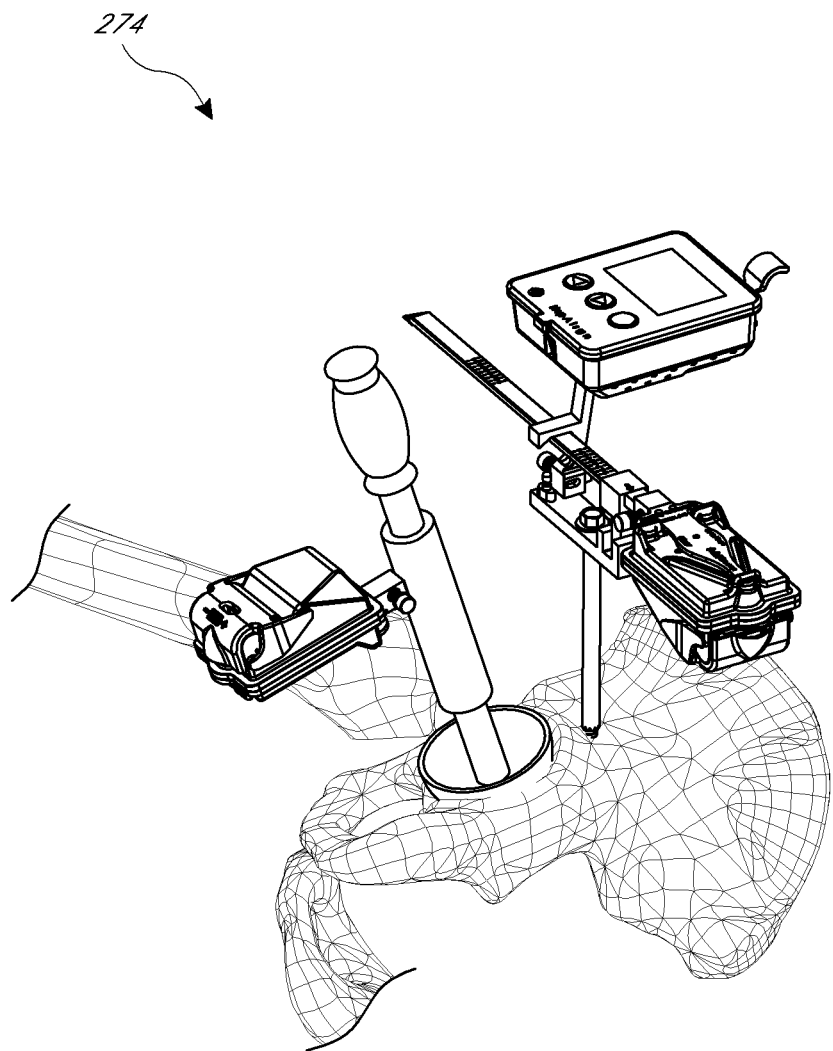
FIG. 12 illustrates a step of navigating placement of a cup portion of an artificial hip joint.

FIG. 12 shows the cup orientation placement navigation assembly of FIGS. 11A-C adjacent to the anatomy. This figure also illustrates a free-hand navigation configuration 274, in which at least the orientation devices 172, 204 are capable of six degrees of motion relative to each other. Any of the variations of FIG. 11A-11C could be substituted in the illustration. In particular, the handle 304 is oriented as desired. In one embodiment, the system 100 displays in real time the angle of the cup relative to the navigated plane, which was acquired as discussed above. Angles that can be displayed include any one or more of anteversion and abduction for example. Preferably the clinician can confirm the position of the cup within a short fixed time, such as within about 20 seconds. In one embodiment, the angles displayed can be adjusted by about 40 degrees abduction and 20 degrees anteversion. These angles are not critical, but they relate to the range of motion of the leg. It is preferred to be close to these angles because motion in abduction and anteversion extends on either side of these angles. It is believed that the systems discussed herein can increase the percentage of patients in a "safe zone" close to these angles, typically described as within 10 degrees of these angles. In contrast, studies show that conventional techniques yield close to 50% of patients outside the "safe zone."

Depending on the sensors and the timing of cup placement step of FIG. 12, the user may mount the sensing device 204 on the elongate member 224 again and may return the system 100 to the parked configuration 260 and also may initialize or zero the system 100.

The system 100 can be configured to provide a pre- and/or post-operative estimation of an angle relative to the angle of the table. In the posterior approach, the patient is placed on his/her side. In this approach, there is more chance for the patient's position to shift intra-operatively. In one embodiment, an alignment rod can be coupled with the sensing device 204 and aligned with the plane of the table. The orientation of the sensing device 204 when so aligned is recorded in the system. Later in the procedure, one or more angles is calculated and displayed to the user based on the assumption that the pelvis has not moved. At such later stages, the orientation of the sensing device 204 can be confirmed again relative to the table to provide information about whether the patient has moved. If significant movement has occurred, such that any assumptions of no movement are violated, some or all of the landmark acquisition steps can be repeated. Alternatively, the movement of the pelvis can be tracked by the sensing device and corrected for. The manner of incorporating the table orientation with landmark acquisition is discussed in greater detail below.

The user will have placed the artificial ball of the replacement hip join in the proximal femur and thereafter can place the ball in the cup, which was properly oriented using the techniques discussed above.

FIG. 1 shows that thereafter, the user can optionally confirm orientation and/or leg length using the system 100. The leg with the artificial hip joint assembled is placed in a neutral flexion and/or abduction and/or rotation position. The acquisition assembly 112 can be placed in the retracted configuration 266. The distal end 228 of the elongate member 224 can be brought into contact with a landmark, which may be the same landmark acquired in FIG. 6. Once contact is made with this landmark (e.g., the bovie mark), the orientation of the sensing device 204 is determined by the system 100. Also, the distance indicated on the scale 226 of the elongate member 224 is input into the system in any of the manners discussed above (e.g., manual or sensed). The system 100 can thereafter calculate components of vectors along the S-I axis (leg length) or M-L axis (offset).

Once leg length and offset are determined post-operatively, they can be compared the pre-operative measurements (FIG. 6) to let the surgeon know if any adjustments should be made before completing the hip replacement surgery.

Figure 13:
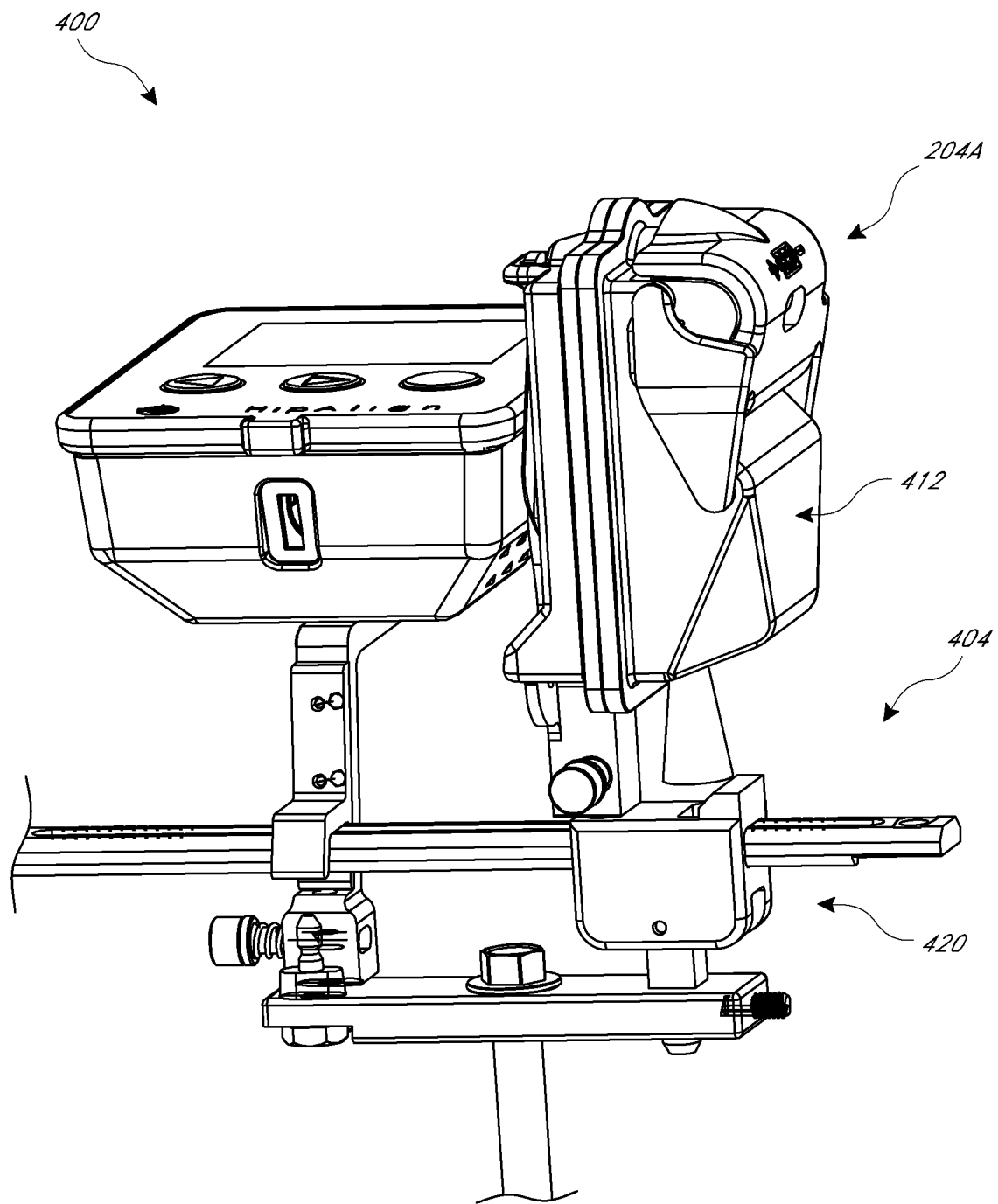
FIG. 13 is a perspective view of another embodiment of a hip navigation system.
Figure 14:
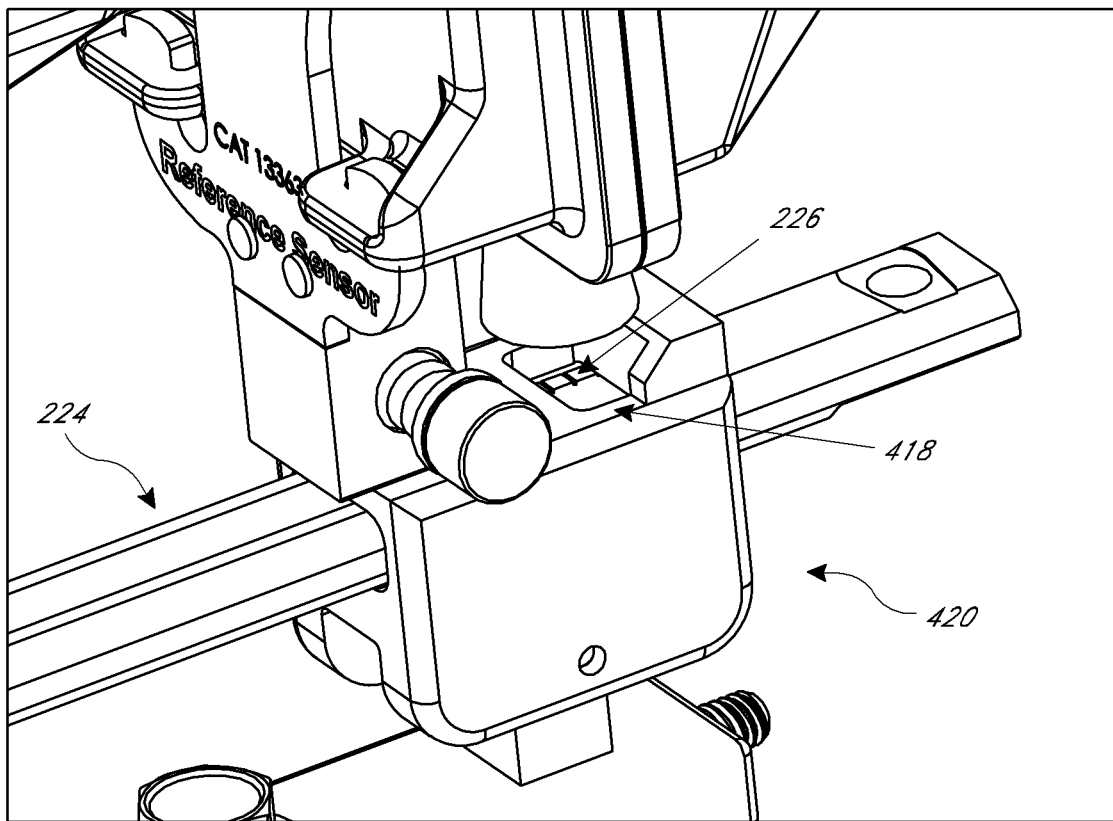
FIG. 14 is a detail view of portion of the system of FIG. 13, with a camera recording linear position of a registration arm.

FIGS. 13 and 14 show other embodiments of a hip navigation system 400 that can include any of the features discussed above. In addition, the system 400 includes a free-hand sensor mount 404 that can be used to mount a freehand orientation device 204A in one configuration. The freehand orientation device 204A preferably includes inertial sensors, similar to those hereinbefore described. The device 204A preferably also includes a camera 412. The field of view is illustrated by the cone projecting downwardly from the base of the freehand orientation device 204A. FIG. 14 shows that the field of view includes a window 418 in a sliding support 420. The window 418 enables the scale 226 to be viewed therethrough.

Because hip replacement procedures involve an open surgical field with a substantial amount of exposed tissue and blood the line of sight the camera 412 to the scales can become obstructed. In one embodiment, a hood is provided above the window 418. The hood keeps most of the blood and tissue out of the space where the camera views the scales. Additionally, a scrubber component, e.g., a thin rubber member, can be provided above the scales 226, 226A (discussed below) to prevent this tissue or fluids from entering into the field of view laterally.

One advantage of the system 400 is that the camera 412 can automatically process the image captured through the window 418 and thereby determine the position of the elongate member 224 relative to the sliding support 420. A further advantage of this is to eliminate one step from the navigation process, e.g., to eliminate the need to enter the linear dimension into the system 400. Eliminating the step can reduce time and/or personnel in the operating room. Also, the camera 412 can be configured to read a much higher resolution than can be read by a clinician. This can provide greater accuracy in the system overall. Not only that, but he camera can be configured to make fewer or no errors in reading the position, which can improve outcomes overall. For example, miniature cameras can produce data in JPEG or other image format that a processor in one or both the orientation devices 172, 204A can process to extract the linear position of the elongate member 224.

Figure 15:
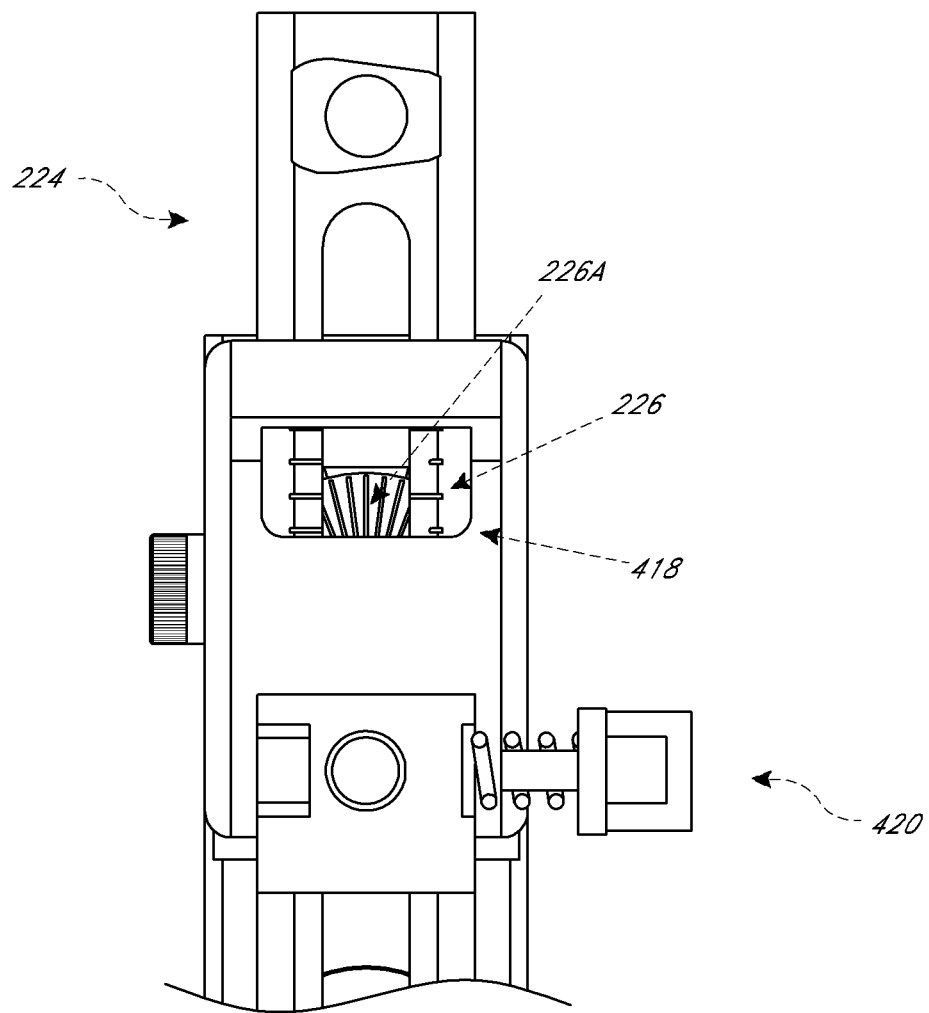
FIG. 15 shows a variation of the embodiment of FIGS. 13 and 14 in which rotational orientation and linear position can be acquired by a camera viewing a radial scale.
Figure 16:
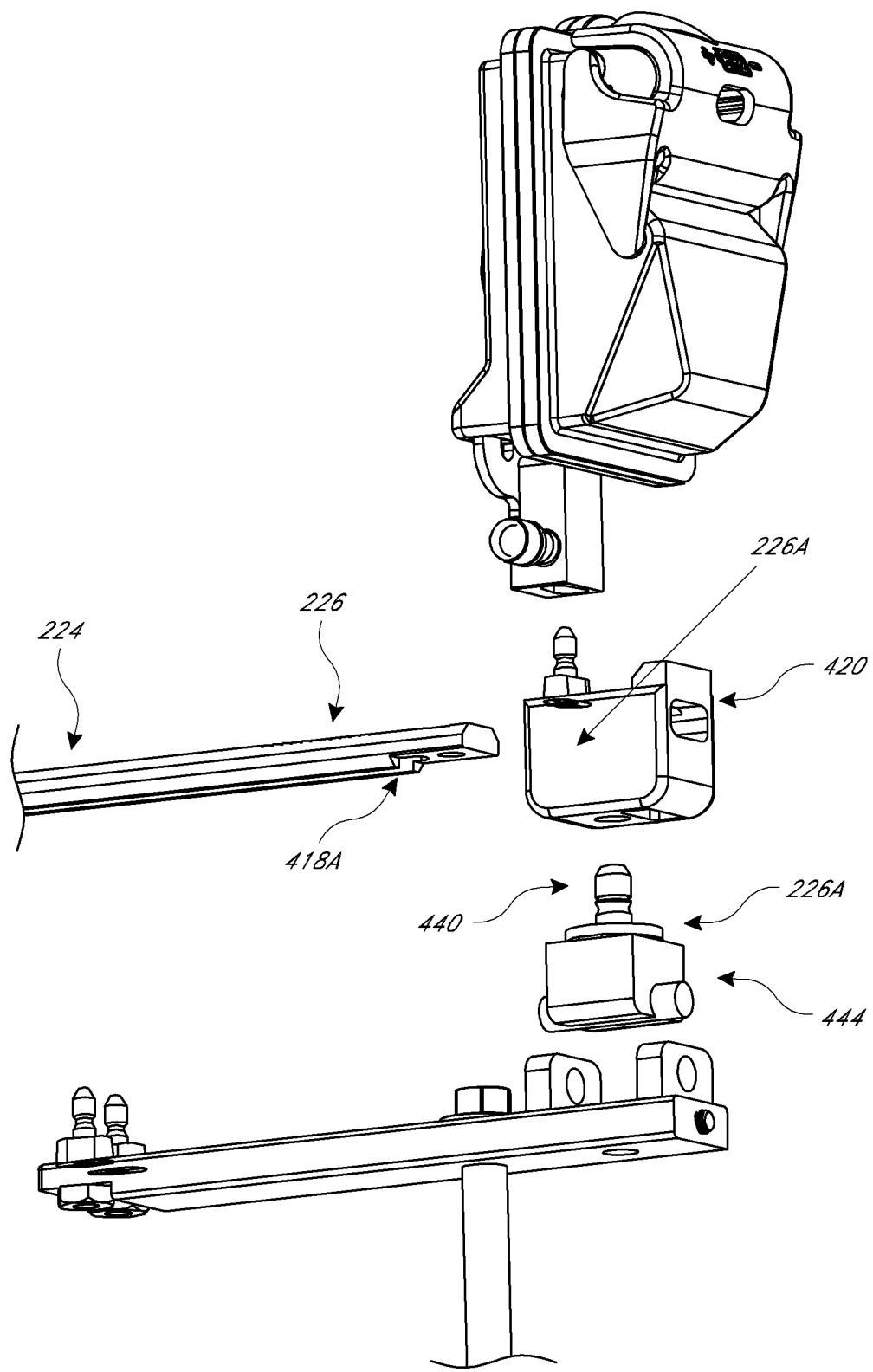
FIG. 16 is an exploded view of an assembly showing a tilt/rotation mechanism adapted to enable a camera to track at least one rotational position.

A further modified embodiment is described in FIG. 15, which shows an arcuate scale 226A that can be positioned on a structure beneath the elongate member 224, e.g., on a structure beneath the orientation device 204A that is rotationally fixed relative to an axis extending out of the page. FIG. 16 shows one configuration with this arrangement. A pivot 440 enables the sliding support 420 to rotate about an axis extending upward on the page. Although the pivot 440 is fixed about this upward extending axis, it can rotate about a pivot 444. A window 418A in the elongate member 224 enables the camera to see through the support to view the scale 226A disposed on an arcuate or disk shaped feature of the pivot 440. The scale 226A can be read by the camera 412 or a second camera to provide accurate determination of the rotational position of the elongate member 224. This can enable one of the sensors in the orientation device 204A to be eliminated or inactivated. In another embodiment, camera date derived from the scale 226A can be used to confirm the data from sensors in the orientation device 204A. Preferably the scale 226A has markings over a range of from about 15 to about 90 degrees, for example, between about 30 and about 60 degrees, e.g., at least between about 40 and about 50 degrees.

2. Posterior Approach Systems Adapted for Accelerometer Sensitivity

Figure 17A:
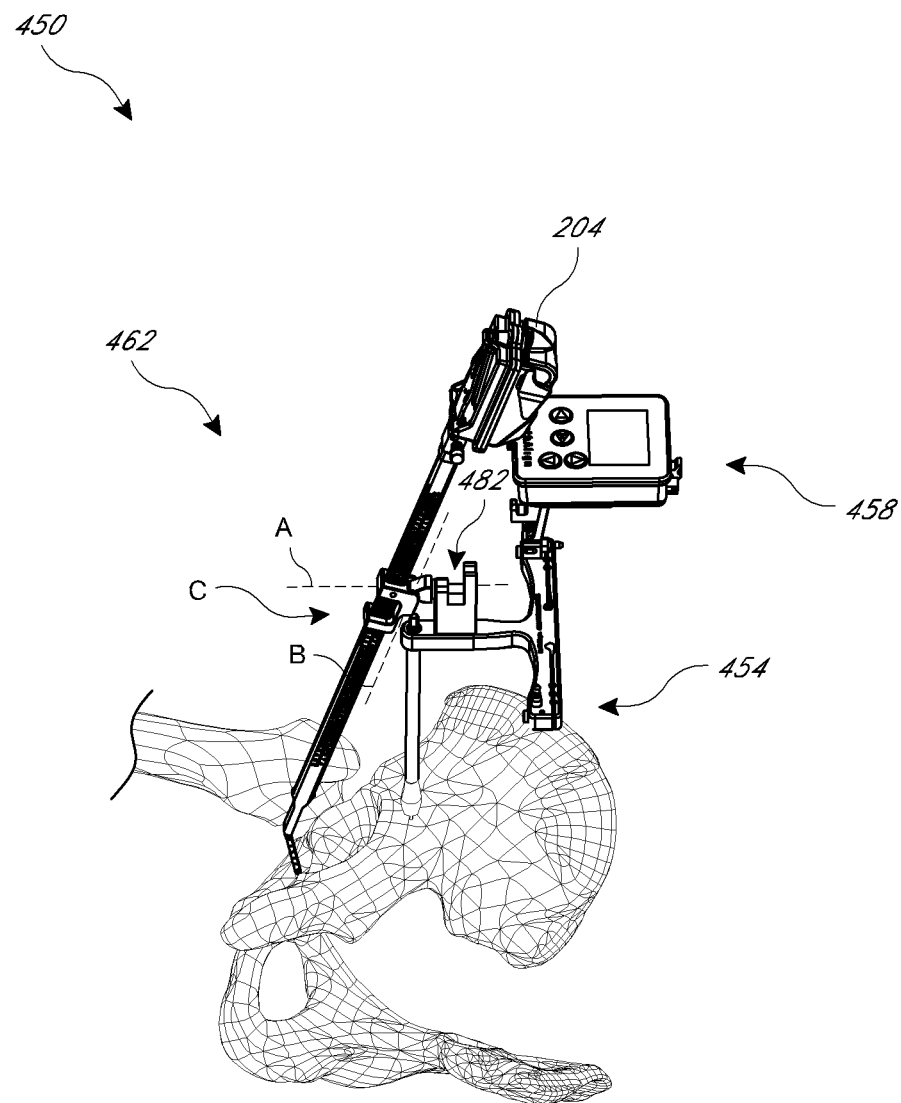
Figure 17B:
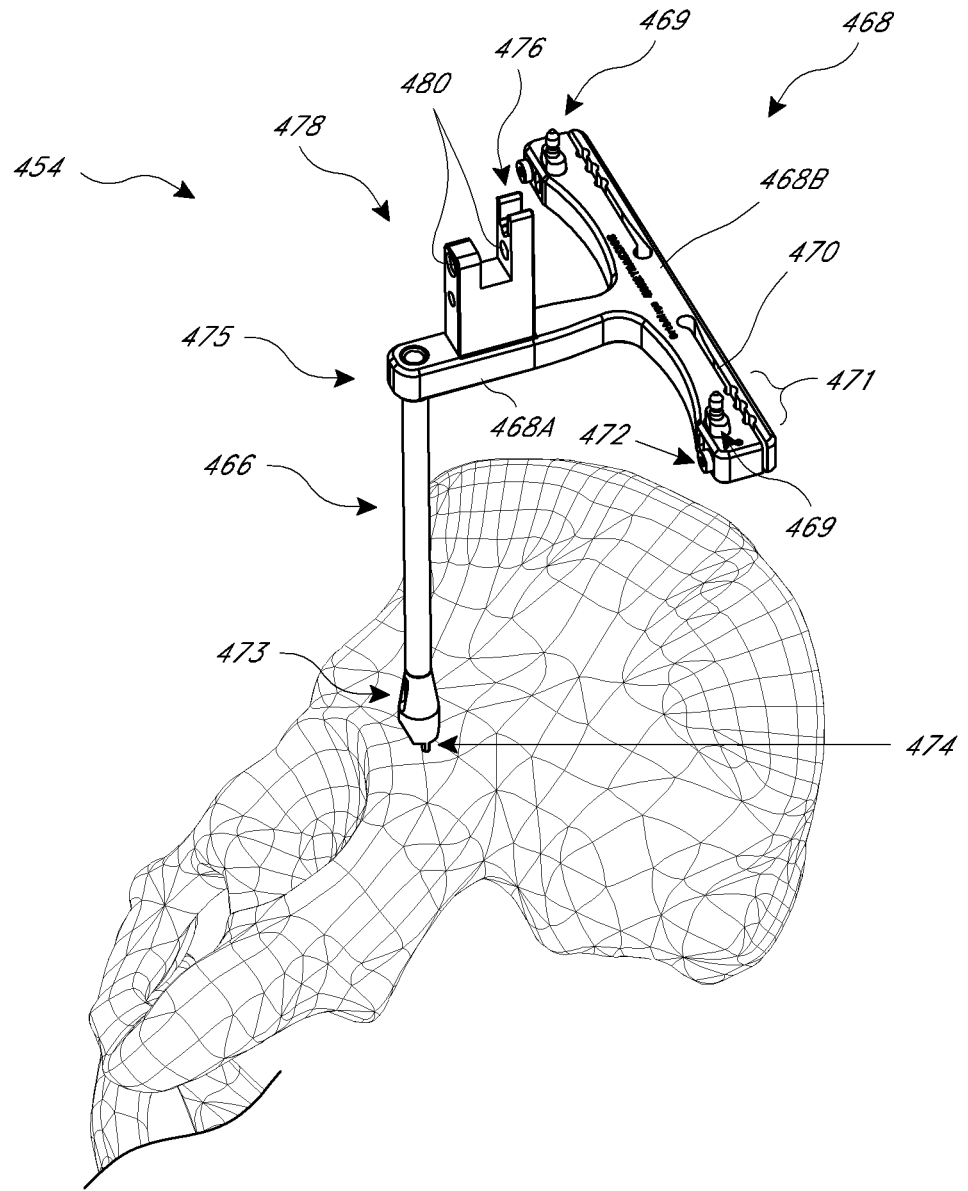

FIGS. 17-17B illustrate another embodiment of a system 450 for navigating a hip procedure from a posterior approach. The system 450 includes an anchor jig 454, an alignment system 458, and a landmark acquisition assembly 462. The components may be similar in some respects to those discussed above, and such descriptions are incorporated with this embodiment where consistent.

The jig 454 includes a hollow fixation member 466 and a platform 468 for coupling a plurality of devices to the pelvis. The platform has a generally T-shaped configuration including a first portion 468A coupled with the proximal end of the fixation member 466 and a second portion 468B disposed transversely to the first portion 468A. The first portion 468A provides a support for a cradle 476 discussed further below. The second portion 468B can include a plurality of docking devices 469 for coupling directly or indirectly with the orientation device 172. The T-shaped configuration provides the advantage that the docking devices 469 can be disposed father away from the surgical site than is the case with the system 100. This reduces any intrusion of the orientation device 172 into the working field.

In some cases, the fixation member 466 provides adequate stability in anchoring the system 450 to the pelvis. In other situations, the jig 454 can be coupled with the pelvis from the second portion 468B. For example, a slot 470 can be formed in the second portion 468B on one or both sides of location where the first portion 468A extends from the second portion 468B. The slots 470 can extend from a lateral edge of the second portion 468B toward location where the first portion 468A extends from the second portion 468B. The slots 470 can include a plurality of channels 471 configured to receive fixation pins (e.g., Steinmann pins) that can be advanced into the pelvis. The channels 471 extend generally parallel to the fixation member 466. The fixation pins can be securely connected to the second portion 468B in the channels 471 by a clamp device 472. The clamp device can include a screw configured to draw the portions of the second portion 468B on either sides of the slot 470 toward each other and thus to create large frictional forces on the pins in the slots 471.

The slots 470 preferably are aligned such that a plane extends along both of the slots 470 along their length. Because the slots 470 are long and slender this plane can be readily visualized in an X-ray image. It is preferred that the jig 454 be aligned to the pelvis such that the plane extending along the slots 470 is perpendicular to an axis of the patient (e.g., the intersection of the medial lateral plane and the transverse mid-plane of the patient). This feature provides a convenient way to visually confirm proper positioning of the jig 454 in one embodiment.

The fixation member 466 includes a registration feature 473 and a foot 474 adjacent to a distal end thereof and a coupling 475 adjacent to the proximal end thereof for connecting to the platform 468. The foot 474 includes a plurality of spaced apart spikes extending from a distal end thereof capable of preventing or limiting rotation of the jig 454 when the fixation member 466 is connected to the pelvis. FIG. 17 shows that securing the jig 462 to the pelvis can include positioning a pin or other bone engaging device through the fixation member 466. The pin and spikes extending from the foot 474 can provide three or more points of contact with the pelvis providing secure mounting of the jig 462.

The coupling 475 generally secures the platform 468 to the fixation member 466. In some embodiment, the coupling 475 has a rotational capability that enables the platform to be positioned at selective locations about the longitudinal axis of the pin 466, for example to enable the platform 468 to be initially positioned in the correct orientation or to be moved during or after the procedure to make space for other surgical devices. One arrangement provides matching splines that extend parallel to the longitudinal axis of the fixation member 466. This arrangement would permit splines on an upper portion of the coupling 475 to be disengaged from splines on a lower portion of the coupling 475. When disengaged, the platform 468 and the upper portion of the coupling 475 can be rotated relative to the lower portion of the coupling 475. The splines can thereafter be re-engaged.

The jig 454 also preferably includes a cradle 476 that can be used to hold a probe arm 477. The cradle 476 includes a U-shaped recess having a width between two upright members that is about equal to the width of an arm 477 of the landmark acquisition system 462. FIG. 17 shows the probe arm 477 in a parked configuration as discussed above. If the sensor 204 operates with components that are prone to accumulated error sources, the parked configuration can be used to eliminate such error. As discussed above, the system 450 can be configured such that the position and/or orientation of the sensor 204 relative to the orientation device 172 is known. Thus, when the arm 477 is in the cradle 476 any accumulated error of components of the sensor 204 can be eliminated.

The cradle 476 can provide other convenient functions even if the sensing devices in the sensor 204 are not subject to sources of accumulated error. As discussed elsewhere herein, for confirmation of accuracy of the system or to provide a simplified reference frame not requiring landmark acquisition, it may be desirable at some point of the procedure to use the probe arm 477 and the sensor 204 to estimate the plane of the surgical table upon which the patient is resting. If, as discussed above, the plane intersecting the slots 470 is oriented perpendicular to the axis of the patient when the jig 454 is mounted to the pelvis, the cradle will be parallel to the axis of the patient. If the fixation member 466 is oriented vertically, the arm 477 will be parallel to the plane of the table when in the cradle 476. The system 450 can thus use the plane of the table as a reference frame for guiding the placement of the cup without registering landmarks. Or, the plane of the table can be used in combination with registering the anatomy about the acetabular rim, as discussed above, to increase the accuracy of navigating the cup.

The cradle 476 also provides a convenient home position that keeps the arm 477 stationary and out of the way of other surgical instruments. FIG. 17A illustrates the probe arm 477 withdrawn from the cradle 476 and free to move into contact with landmarks.

The jig 454 also includes a pivot feature 478 that is disposed horizontally. FIG. 17B shows that the pivot feature 478 includes two horizontal apertures 480. One of the apertures 480 is formed in the same structure forming the cradle 476 but at an elevation below the cradle 476. The other aperture 480 formed between the cradle 476 and a projection of the fixation member 466. FIG. 17A shows that the probe arm 477 is connected to the pivot feature 478 by a shaft 482 that extends through the apertures. A movement device is provided between the shaft 482 and the arm 477 to enable a distal tip of the arm to be rotated about perpendicular axes and to be advanced linearly relative to the stationary jig 454. One axis of rotation A of the movement device is disposed parallel to and at an elevation above the platform 468. Another axis of rotation B is disposed generally perpendicular to the axis A. Sliding of the arm 477 is enabled by a snug but sliding fit of the arm in a housing C. By orienting the axis A in this manner, the sensitivity of accelerometers in the sensor 204 to small angular motions references points about the acetabulum is heighted or maximized. This can enable landmark acquisition with the system 450 based solely on accelerometers, which advantageously are not subject to accumulated error, which can simplify the landmark acquisition process. Further variations of systems that are configured to allow landmark acquisition based solely on accelerometers are discussed below in connection with Figures*.

The registration feature 473 is a convenient way to enhance the accuracy of the sensor 204. In particular, in one variation of the method discussed above, a distal tip of the probe arm 477 is brought into contact with the registration feature 473. In one embodiment, the registration feature 473 is a notch configured to receive and temporarily retain the tip. Thereafter, the user can interact with the orientation device 172 to initialize accelerometers within the sensor 204. Thereafter the points to be acquired can be sequentially contacted and the orientation and position of the sensor 204 can be sequentially recorded in the system 450. Because the accelerometers are initialized close to the points to be acquired, accuracy of the reading is enhanced as the angular error resulting from an error in the scale factor of the accelerometers is minimized due to the small arc from the registration feature. For example, the jig 454 is configured to enable the landmark acquisition assembly 458 to reach all points to be registered by moving less than about 45 degrees from an initial or home position in some embodiments. In other embodiments, the jig 454 is configured to enable the landmark acquisition assembly 458 to reach all points to be registered by moving less than about 25 degrees from the initial position. In other embodiments, the jig 454 is configured to enable the landmark acquisition assembly 458 to reach all points to be registered by moving less than about 15 degrees from the initial position.

The jig 454 also is configured to interact well with the soft tissue that is disposed around the surgical site in the posterior approach. In this approach, an incision is made in soft tissue that is kept as small as possible. In one approach, the fixation member 466 is positioned at the end of the incision. Where the incision is made as minimal as possible, the jig 454 can also function as a retractor. The T-shaped configuration is particularly well suited for this function because the first portion 468A of the platform 468 can be received between the middle and ring fingers of the user with the second portion 468B in the palm of the hand. With the foot 474 gripping the pelvis, the jig 454 can be tilted from the platform 468 away from the hip joint to retract the tissue away.

Figures 1, 17C:
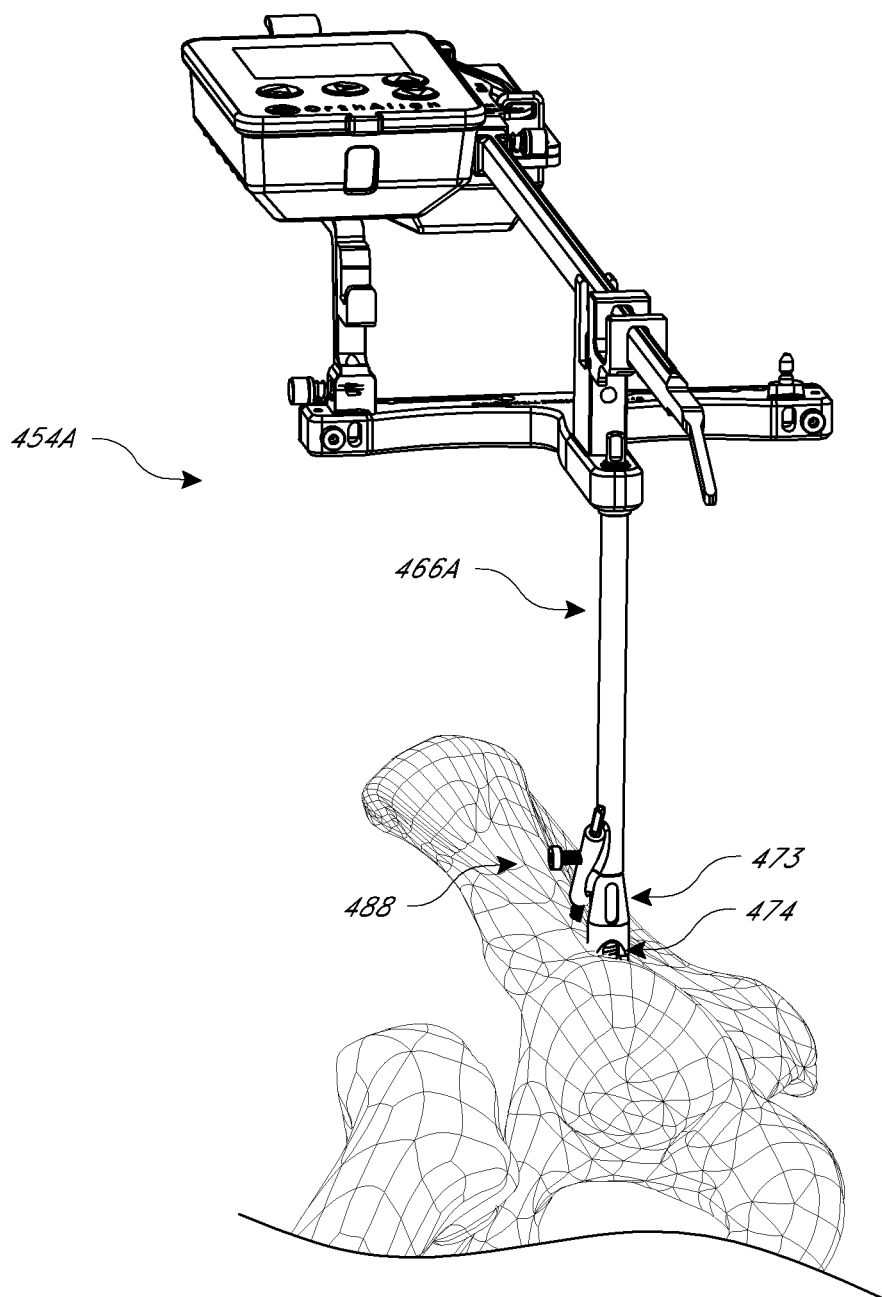
Figures 2, 17C:
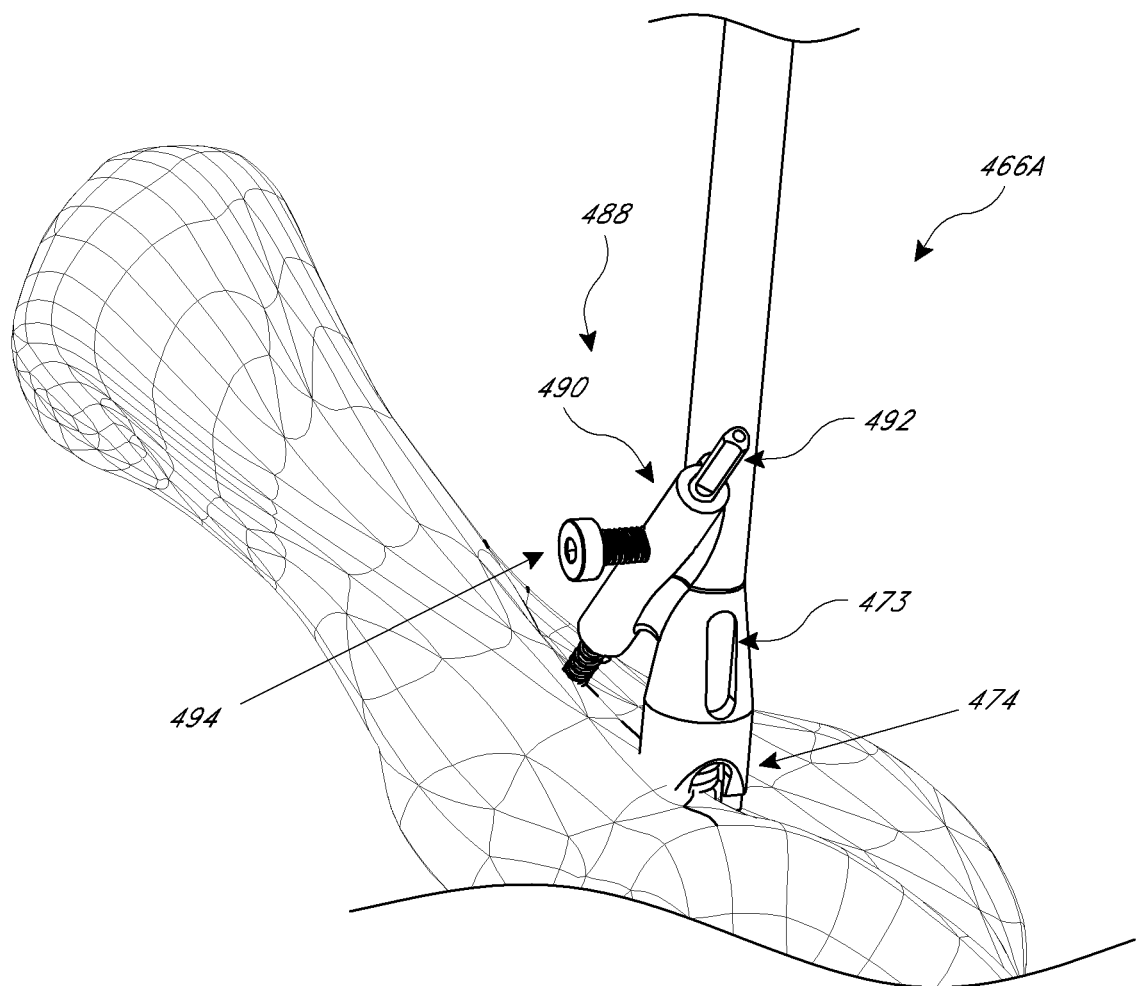

FIGS. 17C-1 and 17C-2 illustrate further embodiments of a posterior approach jig 454A having a mounting device 488 disposed adjacent to the distal end of a fixation member 466A, which is otherwise similar to the fixation member 466. The fixation member 466A includes a tubular body 490 coupled with the fixation member 466A, which in this embodiment acts as a primary fixation member. The tubular body 490 extends along a lumen that is angled relative to the lumen of the fixation member 466A. The lumen in the tubular body 490 is configured to accept a fixation pin 492 that can be driven into the bone, as illustrated in FIG. 17C-2 at an oblique angle. The fixation pin 492 supplements the fixation provided by the fixation member 466A. The fixation pin 492 can be used in conjunction with the optional long pin(s) extending through the channels 471, e.g., into the ilium or as a substitute for that option. The fixation pin 492 has the advantage of not requiring any additional holes in the skin because it is located within the primary incision made to access the joint in the procedure. The fixation pin 492 can be threaded to engage the bone in one embodiment. In some embodiments, a locking device 494 can be provided to secure the pin 492 in the lumen of the tubular body 490. A set screw is one example of a locking device 494 that can be used. The locking device 494 enables the fixation pin 492 to be headless, which avoids issues with screw threads stripping the hole in the bone into which the pin 492 is inserted.

3. Workflow Considerations for Posterior Approach

As noted above, a workflow problem arises in typical hip replacement procedures in that anatomical features that can be more easily references are unavailable in the traditional posterior approach for operating on the joint.

By performing a CT-based study of a large number of human pelvises, the assignee of this application has been able to calculate a population-based average relationship between multiple planes created by various points in, on or around the acetabulum that are accessible during posterior approach hip replacement (each plane, an "Acetabular Plane"), and the Anterior Pelvic Plane. One of the key features of posterior hip navigation for some embodiments disclosed herein is the ability of a module, e.g., software incorporated into a processor, which may be on a computer, or one or both of the orientation device 172 and sensor 204, to calculate a transformation from one reference frame to another. As described in more detail elsewhere herein, several points are referenced in, on or around the acetabulum and from these points a proxy Acetabular Plane is calculated.

Next, in certain embodiments described herein a module operable to process an algorithm, e.g., by executing software in one or both of the orientation device 172 and sensor 204 alone or with a separate computer, is able to calculate a transformation from the proxy Acetabular Plane to Anterior Pelvic Plane. The approach indirectly registers the Anterior Pelvic Plane without requiring a direct supine registration and subsequent patient movement and re-draping necessary in standard navigation. A module in certain embodiments described herein is then able to provide the user real time navigation data of the orientation of a hip instrument (e.g., the impactors 300, 300A) with respect to the Anterior Pelvic Plane.

In certain systems described herein, a further advantage is that the systems are able to implement the plane transformation algorithm to calculate an Anterior Pelvic Plane from one of any number of proxy Acetabular Planes that the surgeon chooses to register. This enables the surgeon to have greater flexibility in Acetabular Plane landmark selection to take into account the quality or accessibility of certain landmarks. For example, in cases of minimal deformity around the acetabular rim, the surgeon may choose to register landmarks around the rim, which are easily accessible. In cases where there is great deformity or high presence of osteophytes on the acetabular rim, the surgeon may instead choose to register an Acetabular Plane based on extra-acetabular landmarks (or described as "off-rim" elsewhere herein) outside of the rim that are unaffected by disease or prior hip replacement surgery.

Examples of anatomical landmarks that may be used to create a proxy Acetabular Plane and that are shown in FIG. 2 include but are not limited to:

Extra-acetabular landmarks (Ischium/Ilium/Pubis)
(A) The lowest point of the acetabular sulcus of the ischium
(B) The prominence of the superior pubic ramus
(G) The confluence of the anterior inferior iliac spine (AIIS) and the outer border of the acetabular rim Acetabular Rim Landmarks
(E) The center of the anterior insertion of the trans-acetabular ligament
(F) The center of the posterior insertion of the trans-acetabular ligament
(H) The most superior point of the acetabular rim.

Additional points can be combined with either of the groups of points listed above. For example, in one embodiment, point "D" is used. Point D is the midpoint of the inferior border of the acetabular notch. As discussed in connection with FIG. 36 below, point D corresponds to the bottom landmark 380B used to form the line 382. Point D is used in that approach to provide patient specific refinements to the positioning.

A further key benefit of certain embodiment discussed herein is that the foregoing plane transformation capabilities increase the accuracy of the transformation between the proxy Acetabular Plane registered and the Anterior Pelvic Plane above the general population average data by the user inputting certain patient-specific information, such as gender.

Additionally, certain embodiments of systems including one or more of the orientation device 172, sensor 204, or a separate computer may have modules that are operable, e.g., by processing software, to allow the user to input an angular or plane relationship between an proxy Acetabular Plane and Anterior Pelvic Plane that the surgeon measured based on pre-operative imaging, allowing for a partial or whole plane transformation based on patient-specific data rather than population data. By way of example, the surgeon may choose to pre-operatively measure an angle created by (a) landmarks that are both visible on an A/P pelvis x-ray and that can be referenced during posterior hip replacement, and (b) landmarks that are both visible on the pelvis x-ray and that are directly associated with inclination measurement in the Anterior Pelvic Plane. If this angular relationship is inputted into a module of a system including one or more of the orientation device 172, the sensor 204, or a separate computer, which module is capable of making calculations processing software and the surgeon registers the landmarks described in (a), inclination navigation will be based specifically on that patient rather than a population average. Landmarks (D) and (H) listed above are examples of landmarks that are both visible on an A/P pelvis x-ray and that can be referenced to create a proxy Acetabular Plane in posterior hip replacement.

These aspects of the systems adapted for posterior approach hip joint replacement can greatly enhance both workflow and accuracy in such procedures.

B. Navigation Using Inertial Sensors and Jigs for Referencing Anatomical Landmarks With Anterior Approach 1. Apparatuses for Anterior Approach Hip Navigation FIGS. 18-21 illustrate a hip navigation system 500 adapted to navigate a hip joint procedure from an anterior approach. Anterior approach to hip replacement advantageously can be less invasive than posterior approach. In particular, the anterior approach can enable smaller incisions, less soft tissue dissection, and shorten recovery time for patients. The system 500 includes an anchor system 504, an alignment assembly 508 and a landmark acquisition assembly 512.

Figure 18:
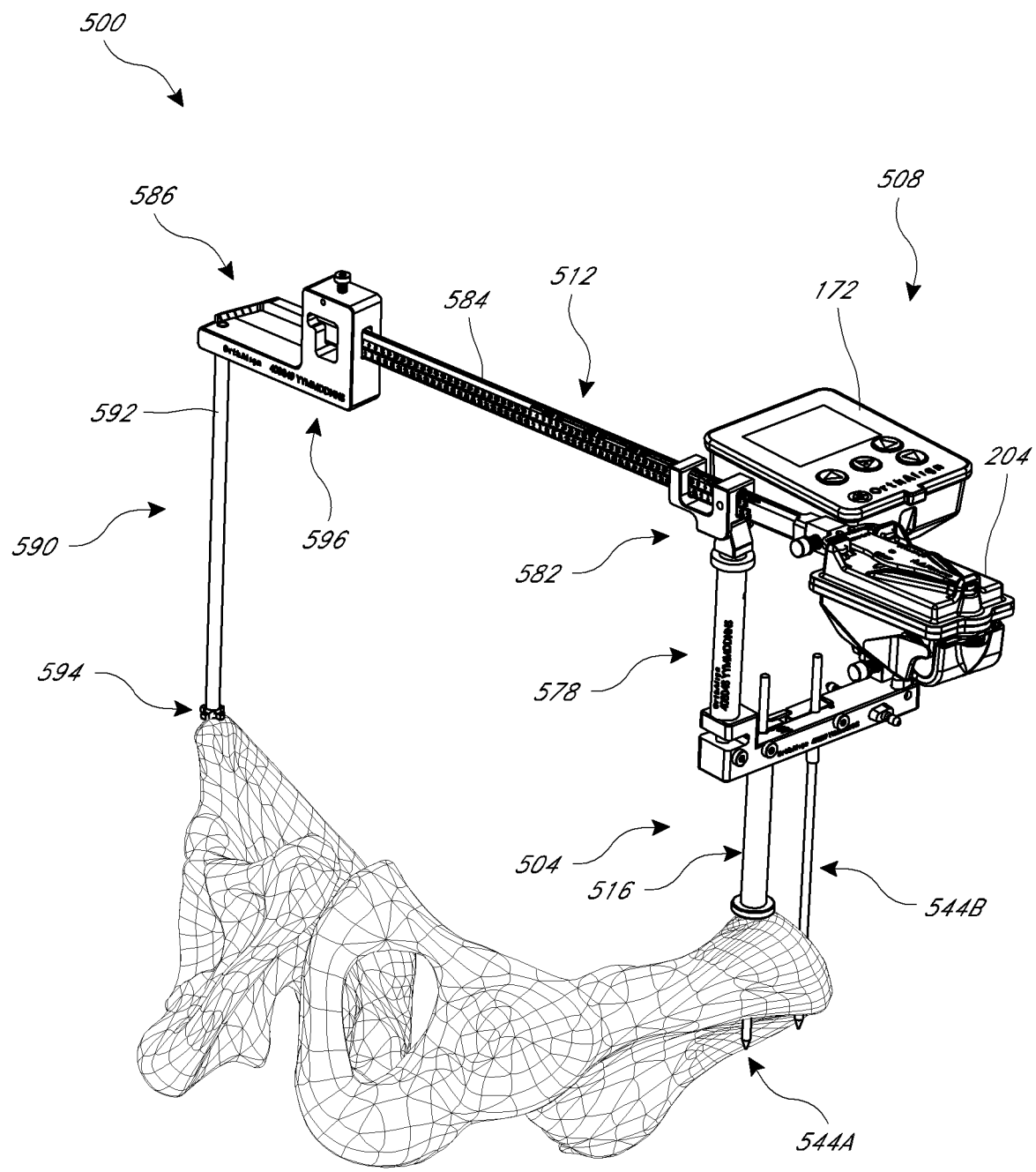
FIGS. 18-21B illustrate a hip navigation system configured for an anterior approach hip replacement procedures, and various aspects of such procedures.

FIG. 18 shows the anchor system 504 in more detail. The system 504 is configured to securely couple the navigation system 500 to the hip, such that movement between the system and the hip are minimized or eliminated. The anchor system 504 includes a cannula 516 having a distal end 520 and a proximal end 524 with a lumen 532 extending between the distal and proximal ends. The proximal end 524 of the cannula 516 is coupled with a platform 536, for example adjacent to one lateral end of the platform. The platform 536 is similar to those hereinbefore described having a plurality of docking device 538, 538A disposed away from the location where the proximal end 524 and the platform 536 are connected.

The docking devices 538 are configured to couple with detachable mounting devices that securely but temporarily couple sensor to the anchor system 504. The two docking device 538 on the top surface of the platform 536 enable the anchor system 504 to be used for either left or right hip procedures. As shown in FIG. 18, the docking device 538 on the side of the platform 536 closest to the medial plane of the patient is preferably used for docking. The top side docking feature not in use in FIG. 18 would in fact be used in performing a procedure from the other side of the patient. The docking device 538A on the side surface of the platform 536 is provided for a temporary intra-procedure mounting of a sensor to the platform 536. As discussed further below, this temporary mounting provides a known orientation and/or location of two sensors relative to each other during a procedure, which enables the system 500 to control sources of error with certain types of sensors.

The platform 536 also can have a channel 540 disposed away from the cannula 516. The channel 540 can have a lumen disposed along an axis substantially parallel to the lumen 532 of the cannula 516. In one embodiment, the anchor system 504 is configured to securely couple the platform 536 to the hip by placement of two spaced apart pins 544A, 544B. FIG. 18 shows that the pin 544A can be advanced through the cannula 516 such that a distal end of the pin 544A contacts and penetrates a bony prominence of the pelvis. In one technique the pin 544A is positioned at or as close as possible to the anterior superior iliac spine (ASIS) of the pelvis. The pin 544B is advanced through the channel 540 and into the pelvis at a location offset form the ASIS. The distance between the pins 544A, 544B and the precise positioning of the pin 544B are not critical, but are determined by the locations of the connection of the cannula 520 to the platform 536 and of the channel 540.

The pins 544A, 544B can take any suitable form but preferably have the same cross-sectional profile as the lumens in the cannula 520 and in the channel 540, e.g., they can be circular in cross-section. The pins 544A, 544B can be modified Stienmann pins, e.g., configured to extend at least about 5 cm above the platform 536 and having a diameter of about 4 mm.

The anchor system 504 also has a locking device 556 for securing the platform 536 to the pins 544A, 544B. In one embodiment, the portion of the platform disposed around the pins comprises medial and lateral portions 560M, 560L that can move away from each other to release the pins 544A, 544B or toward each other to frictionally engage the pins. For example, a pair of hex-driven screws can engage the medial and lateral portion 560M, 560L to translate them toward and away from each other respectively. The locking device 556 preferably is quickly and easily removed from the pins such that other instrument, such as X-Ray or other diagnostic devices can be brought into the vicinity of the surgical field during the procedure. Preferably the pins 544A, 544B have markings along their length such that if the platform 536 is removed for imaging or other reasons it can be quickly re-positioned at the same elevation.

The cannula 520 also has a foot 568 adjacent to or at the distal end 528 to minimize or eliminate error that could arise due to uneven penetration depth of the anchor system 504 when compared to the position of a distal probe of the landmark acquisition system 512 when landmarks are being acquired. The foot 568 can include an annular projection disposed outward of the cannula 520. Preferably the foot 568 extends laterally from the outer surface of the cannula 520 by a distance equal to or greater than the wall thickness of the cannula 520. In some embodiment, the surface area beneath the foot is equal to or grater than the surface area of the cannula when viewed in cross-section at a location where the foot 568 is not located, e.g., at an elevation about the foot 568.

The alignment assembly 508 is similar to those hereinbefore described. It can have a rigid extension 570 configured to detachably secure a orientation device 172 to the docking device 538.

Figure 19:
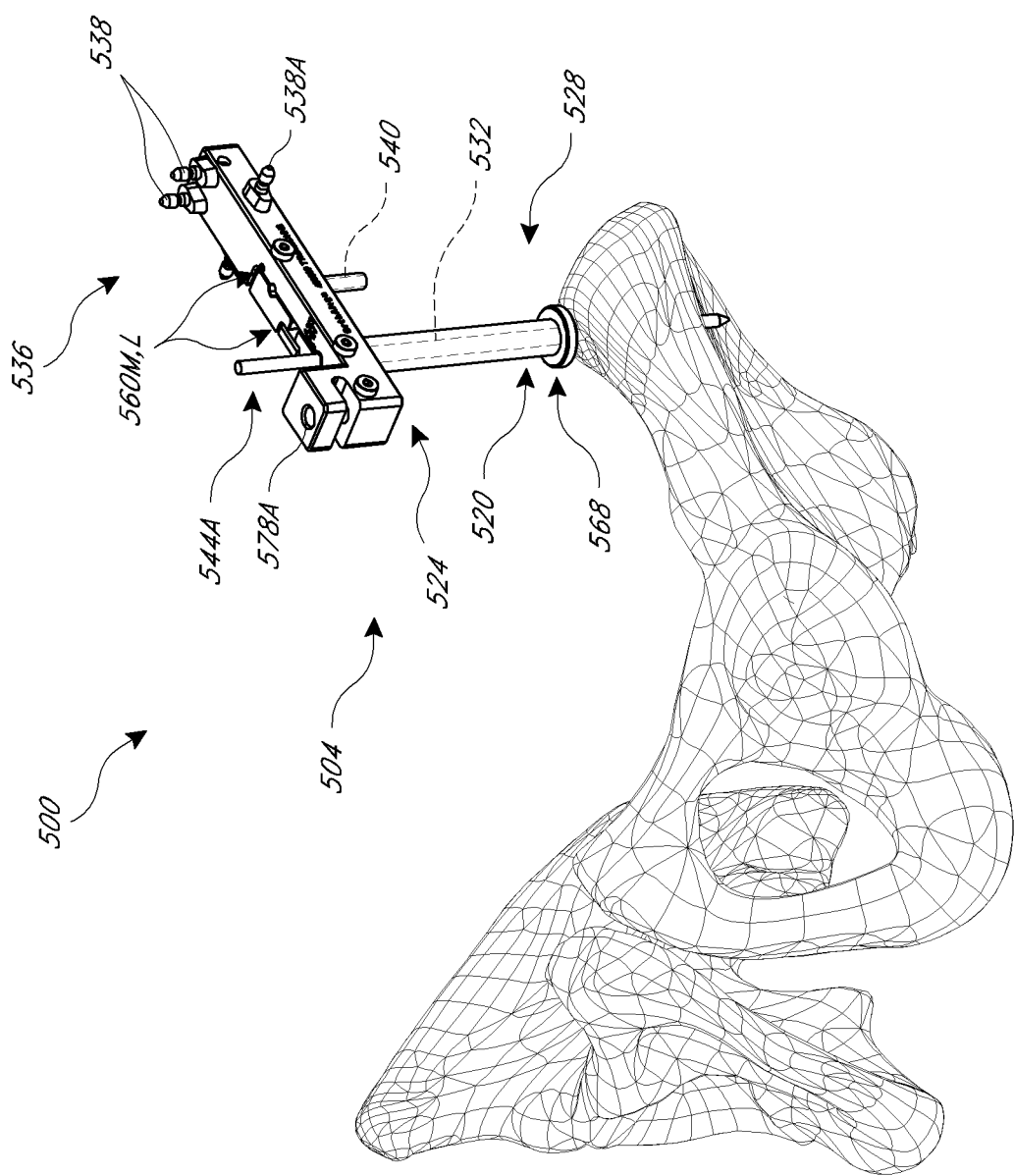

The landmark acquisition assembly 512 is similar to those hereinbefore described, but is configured to be unobstructed in use by soft tissue anterior to the pelvis of the patient. In one embodiment, an extension 578 is provided to elevate a pivoting and sliding mechanism 582. The pivoting and sliding mechanism enables a probe arm 584 to slide away from the extension 578 toward the location of landmarks to be acquired. The pivoting and sliding mechanism 582 can be similar to any of those discussed above. The distal (lower) end of the extension 578 can be coupled to the platform 536 in any suitable way. For example, the distal end can include a pin-like projection that is received in, e.g., friction fit in, an aperture 578A having the same shape. Detents or other locking features can be provided to securely connect the extension to the platform 536 in the aperture 578A. FIG. 19 shows that the aperture 578A can be formed in a portion of the platform 536 that is elevated compared to the portions of the platform through which the pin 544A extends. This portion is elevated to provide sufficient bearing engagement to minimize play. It also has a slot generally parallel to the top surface of the platform 536 which serve the function of engaging a ball detent on the lower end of the extension 578.

The probe arm 584 can be configured as an elongate member with a plurality of markings, discussed below. A distal end of the probe arm 584 can include an angled tip 586 that assists in probing anatomy in some techniques, e.g., portions of the femur for leg length and femoral head positioning confirmation. In the posterior approach, the angled tip 586 is used to directly contact anatomy.

In the anterior approach, the angled tip 586 is coupled with a probe extension 590 configured to contact selected anatomy. The probe extension 590 has an upright member 592 that is configured to extend, in the anterior approach, between the elevation of the probe 584 down toward the elevation of the tissue to be probed. A foot 594 on the distal (lower) end of the upright member 592 is configured to engage the tissue in a way that minimizes error due to uneven tissue compression between the point of mounting of the pin 544A and the foot 594. For example, the foot 594 can have a cross configuration that spreads out the force or pressure applied by the landmark acquisition system 512 in use. The proximal end of the extension 590 includes a coupler 596 that connects a distal end of the probe arm 584 with the upright member 592. Preferably the coupler 596 is easily manipulable by the user to modify connect to the probe arm 584. The coupler can include an L-shaped member with an aperture configured to receive the tip 586 of the probe arm 584. A set screw can be advanced through the L-shaped portion to lock the arm 584 in place. The L-shaped portion is configured to couple to the arm 584 such that the tip of the angled tip 586 rests on a projection of the longitudinal axis of the upright member 592.

2. Example Methods for Navigating Using the Anterior Approach

The system 500 can be used to navigate from an anterior approach in the following ways. The orientation device 172 and the sensor 204 can be paired such that they are in wireless communication with each other. This permits one or other of the device 172 and sensor 204 to control the other, store data from the other, and/or display information based on signals from the other. In one method, the orientation device 172 has a display that confirms to the surgeons certain angles based on the data sensed by the sensor 204. The pairing the device and sensor 172, 204 can involve coupling them together and comparing sensor output between the two devices at a plurality of orientations, e.g., horizontal, vertical, and angled at 30 degrees. Some of these positions may be repeated with a plurality of attitudes, e.g., vertical with left side up, vertical with right side up, and vertical with top side up.

As noted above, the components discussed herein can be provided as a kit that enables the surgeon to select among different surgical approaches, e.g., posterior and anterior approaches. The orientation device 172 and sensor 204 may operate differently in these different approaches. Thus, in one method the user will enter into one or both of the orientation device and sensor 172, 204 which approach is being used. This will implement a software module in the orientation device 172 (or in the sensor 204 is the processor running the software is located there) corresponding to the selected approach.

In various embodiments suitable for the anterior approach, the orientation device 172 and the sensor 204 can both have a plurality of sourceless sensors. These components can have both accelerometers and gyroscopes in some embodiments. Some gyroscopes are subject to accumulated error that can be significant in the time frames relevant to these methods. Accordingly, various methods are provided to prevent such errors from affecting the accuracy and reliability of the angles displayed to the surgeon by the system 500. Some approaches can be performed with accelerometers only. For example, variations of the anterior approach can be performed with accelerometers with somewhat less but still acceptable accuracy using accelerometers only. The reduction in accuracy of the accelerometers is balanced against the benefit of eliminating the accumulated error that arises with some gyroscopes. The resolution of accelerometers is sufficient because the points navigated are relatively far apart.

The calculations performed by the system 500 are unique to the hip being treated in some embodiment, so the system receives input of the hip being treated.

The foot 568 is placed on a selected anatomical location, e.g., on the ASIS as discussed above. With the cannula 520 in an approximately vertical orientation the platform 536 is secured to the hip. Securing the platform 536 to the hip can be done in any suitable way, such as with two spaced apart Stienmann pins. Thereafter, the orientation device 172 and the sensor 204 are attached to the platform 536 in the manner shown in FIG. 20A. Depending on the nature of the sensing devices deployed in the sensor 204 it may be advantageous to initialize the sensor at this point of the procedure. As discussed above, certain inertial sensors (e.g., some gyroscopes) are subject to accumulated error. One technique for managing this error source is to periodically initialize or zero out this error. Some techniques involve initialing at this point.

In some embodiment, a frame of reference based on the plane of the table can be input into the system 500. The table reference frame can be a secondary reference frame. In one technique, the sensor 204 is moved from the platform dock position of FIG. 20A to the navigating position on the probe arm 584 as shown in FIG. 18. The probe arm 584 is then pivoted by the mechanism 582 such that the arm points in a direction that is parallel to the patient's medial-lateral midplane and the angled tip 586 superiorly (generally toward the patient's head). The probe arm 584 is also held substantially parallel to the plane of the table. With this heading and orientation the user interacts with a user interface on the orientation device 172 to signal to the orientation system 508 to capture the orientation of the sensor 204. This orientation provides an estimation of the orientation of the anterior pelvic plane. This estimation may be tracked in the system 500 and may alone provide an improvement over the state of the art in un-navigated hip replacement, which involves discrete maneuvers guided by the unaided eye.

At the surgeon's discretion the system 500 can be used to navigate a condition of the femur prior to hip replacement. A mark Fm may be made on the proximal femur. Thereafter the sensor 204 can be initialized or zeroed such as by placing it back in the dock position on the platform (as in FIG. 20A). Thereafter, the probe tip 586 can be brought into contact with the femur mark Fm and locked in place in such contact. See FIG. 21A. The sensor 204 can be transferred to the proximal end of the probe 584 and the orientation device 172 can be signaled to record the orientation of the sensor 204. A distance from the point of attachment of the cannula 520 to the ASIS to the marked position on the femur can then be recorded in the orientation device 172. The position can be based on reading graduated marks on the probe 584 or can be captured automatically by a camera system or a sensor built into the system 500. In one embodiment, graduated marks are read at an upright edge 598 within a bight of a sliding portion of the pivoting and sliding mechanism 582.

Figure 20A:
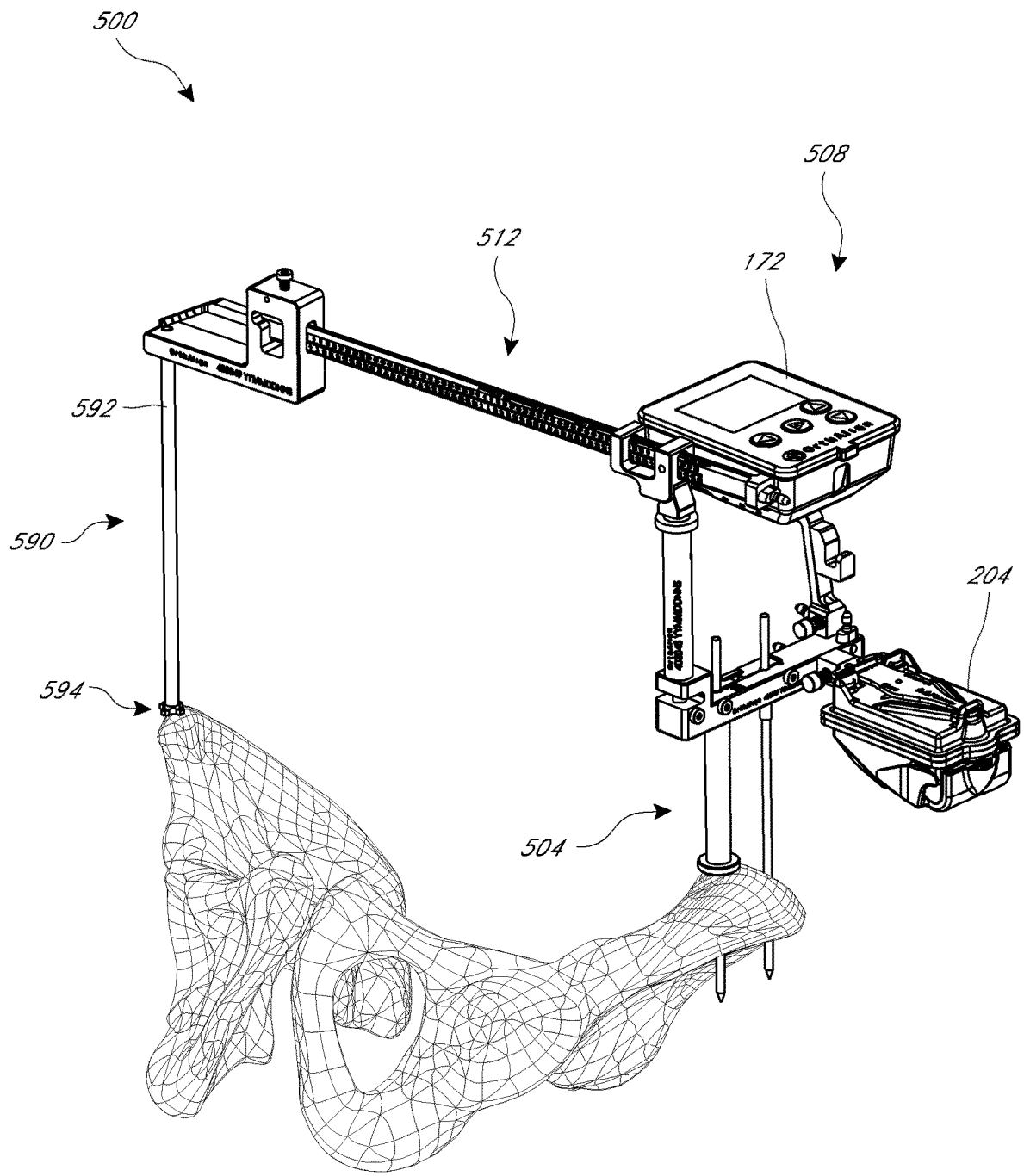

FIG. 20A illustrates a further step of navigating the anterior pelvic plane. As shown, the sensor 204 is docked on the platform 536, in which position any accumulated error associated with some sensors can be eliminated. In a preceding step, the extension 590 is coupled with the distal portion of the probe 584. The foot 594 is brought into contact with the contralateral ASIS. Thereafter, the sensor 204 can be attached to the proximal end of the probe 284 as shown in FIG. 18. The landmark acquisition system 512 can be immobilized and the orientation of the sensor 204 can be recorded in memory in the orientation device 172. Additionally, the distance that the probe 584 is extended to contact the contralateral ASIS can be recorded in the orientation device 172. As noted above, that distance can be read from the scale on the probe 584 at the upright edge 598.

Figure 20B:
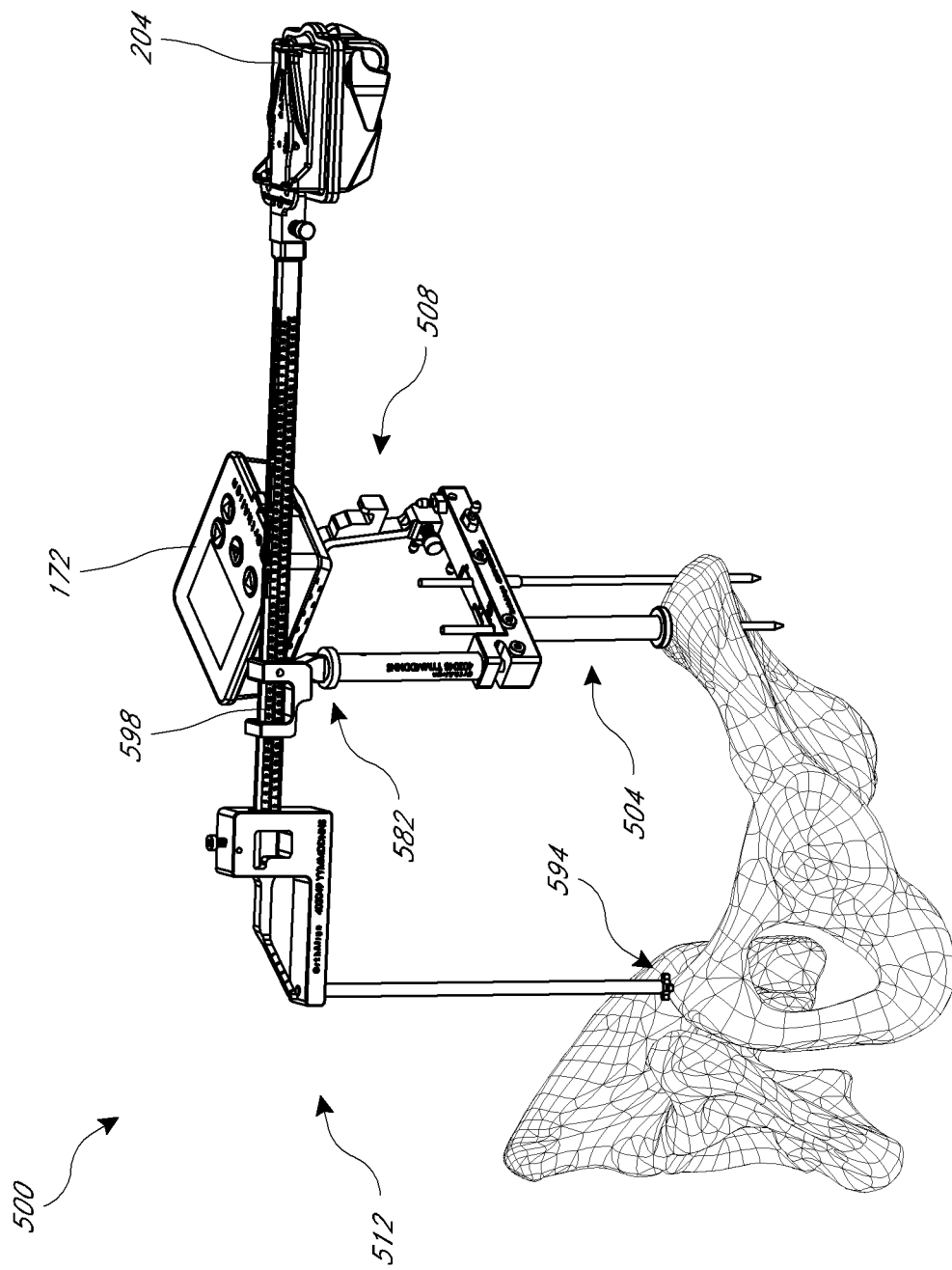
Figure 21A:
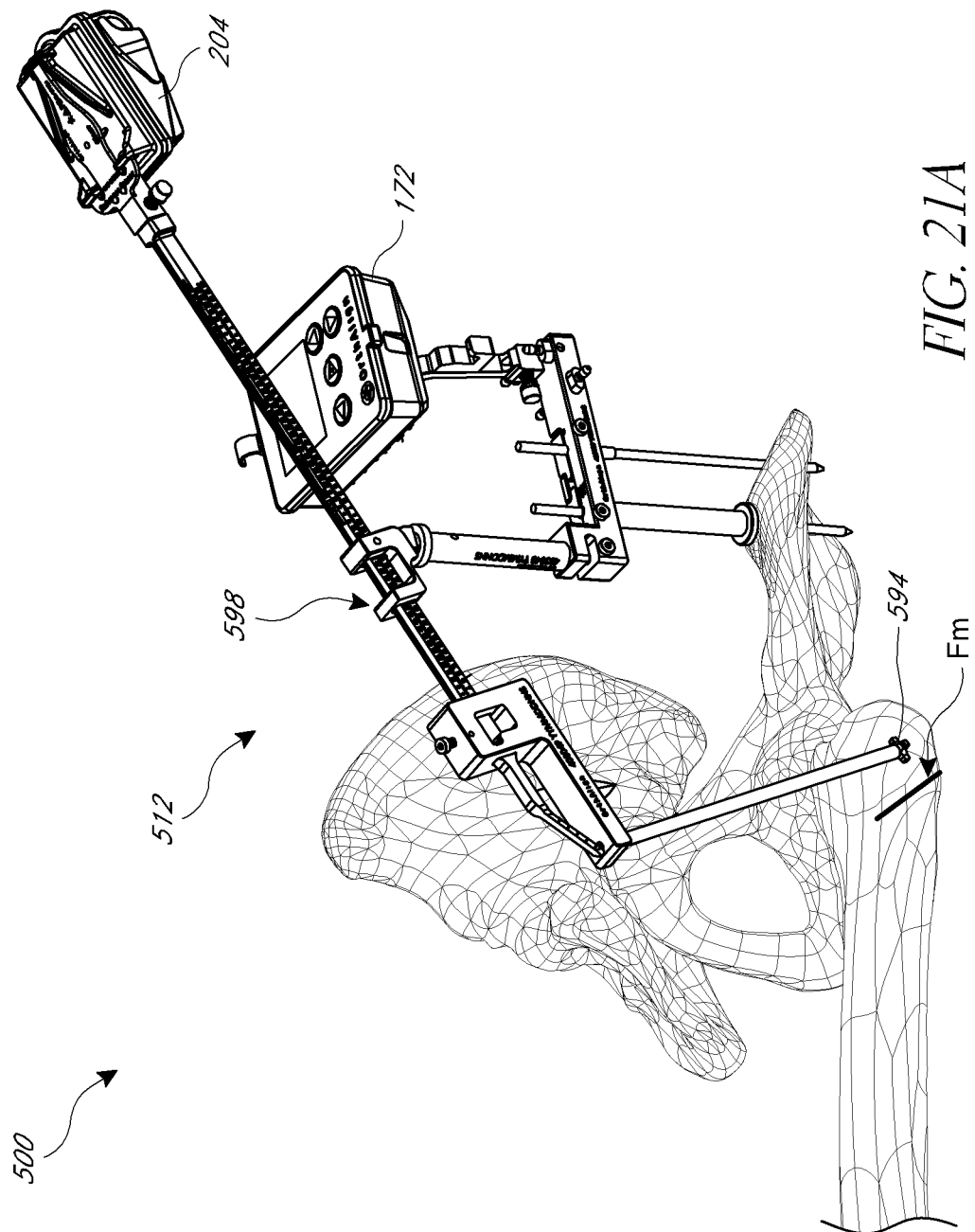

The process to record the contralateral ASIS can be repeated for one or more additional points. The sensor 204 can be docked to the platform as in FIG. 20A to eliminate sources of accumulated error. The probe 584 can then be moved to cause the foot 594 to be in contact with a pubic tubercle. The probe 584 can be immobilized and the sensor coupled with the proximal end as shown in FIG. 20B. Thereafter data indicative of the orientation of the sensor 204 and the distance to the pubic tubercle are recorded in the orientation device 172 in any of the manners discussed above.

Once the foregoing points of the pelvis have been navigated and the data recorded into the orientation device 172 the anterior pelvic plane can be calculated from data indicating the navigated points. The orientation of the anterior pelvic plane is a baseline for placement of the cup portion of a hip prosthesis.

The sensor 204 and the orientation device 172 can at this point be used to guide placement of the cup 360 in the prescribed orientation. Prior to placement the impactor 300, 300A is provided. For example, the impactor 300A can be provided by selecting the appropriate tip component 348 onto the distal end of the shaft 316A. The tip component 348 is coupled with the cup 360, e.g., by threads. The rotational orientation of the cup 360 to the shaft 316A that is most convenient given hole patterns and position of the sensor 204 is selected by matching up the flats 350A, 350B as appropriate. During the process of providing the impactor 300 the sensor 204 can be docked to the platform 536 and source of accumulated error can be eliminated just prior to navigating the cup 360 into place in the acetabulum.

In one technique, the cup 360 is inserted into the acetabulum and placed to approximately the correct orientation. Thereafter the sensor 204 is connected to a docking device 338 on the impactor as shown in FIG. 11A. The orientation device 172 is the activated to display angles indicative of the orientation of the cup, e.g., degrees of inclination and anteversion with respect to the anterior pelvic plane. The angle displayed can directly reflect the table reference frame discussed above. The angle displayed can directly reflect the frame of reference from the acquisition of landmarks. In some cases, angles can be displayed that directly reflect both table reference frame and landmark reference frame. In other embodiments, the table reference frame is not displayed but rather causes a user instruction to be displayed on the orientation device 172, such as a direction to re-acquire landmarks due to disagreement between the angles generated by the two reference frames.

Any of the foregoing combinations of table and landmark reference frames provides redundancy that ensures that the angle information provided to the user is accurate and reliable such that the procedures performed will be better contained within the "safe zone".

When the correct angles are achieved, a tool is used to strike the proximal end of the impactor 300 to lodge the cup 360 in place at the desired angle. In some techniques, the sensor 204 is removed prior to striking the proximal end of the impactor 300. The system 500 includes a module that monitors signals from the sensor 204 and if a large deviation in the readings occurs, the module prevents the angles on the display of the orientation device from changing. This "freezing" of the display is both a safety and an accuracy precaution because a large force due to impact can affect the accuracy of the sensor 204.

If femoral landmarks are acquired in the procedure prior to separating the natural joint, the same landmarks can be acquired after the prosthetic joint is placed to confirm that the replacement of the joint has not changed either the length of the leg, the off-set of the leg from the trunk of the patient or both. For example, the sensor 204 can be docked to the docking device 538A as shown in FIG. 20A. Sources of accumulated error can be eliminated by initializing the sensor 204. Thereafter, the probe arm 538 can be brought into contact with the same landmark (e.g., Fm) acquired early in the procedure. See FIG. 21B. The probe arm 538 can be locked into place and thereafter the sensor 204 can be coupled with the proximal end of the probe arm 538. The orientation of the sensor and the distance to the probe arm 538 can be input into the orientation device 172. These data enable the orientation device 172 to output amounts of change in leg length and leg offset.

In one variation a plurality of points, e.g., three points, on the femur are acquired before and after the joint is replaced. This approach enables a further confirmation that the rotation orientation of the neck of the femur relative to an axis extending through the center of the cup 360 perpendicular to the plane of the acetabulum is unchanged after the procedure.

Of course, the femur registration procedures enable correction of diagnosed deformities including excessive leg length offset and joint offset, as well as mal-orientation of the femoral neck in the natural joint. In other words, the surgeon can begin the procedure with the intent of adding some offset or changing rotational orientation to improve the patient's bone positions and/or orientations post-operatively.

C. Navigation Using Pre-operative Imaging or Characterization

Although the foregoing approaches can improve the standard of care currently in place, further increases in accuracy and even better outcomes and streamlining of the procedure can be provided if the system is configured to account for patient specific anatomical variability.

1. Navigation Using Inertial Sensors and A Custom Jig

Figure 22:
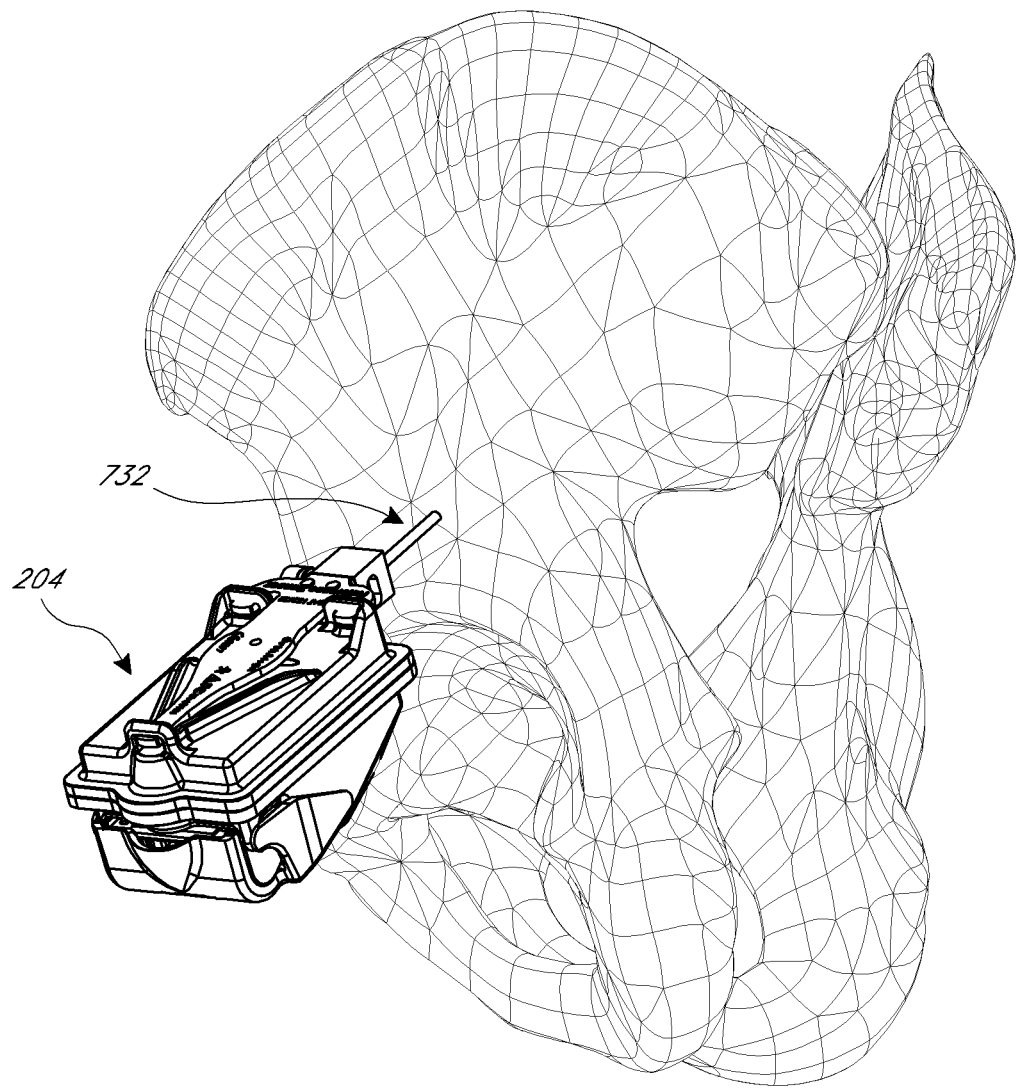

FIG. 22 shows the placement of a hip movement tracking sensor 204 on a pin 732 adjacent to the acetabulum. This position is not limiting, in that the hip movement tracking sensor 204 can be mounted anywhere on the pelvis, but adjacent to the acetabulum is convenient. The pin 732 has been placed with the aid of a pre-operative characterization of the hip of the specific patient. In these methods the pin 732 is placed without the need for intra-operative landmark acquisition.

In one approach, a pre-operative three-dimensional characterization of the acetabulum is performed using any suitable technology, such as CT scan or MM. This pre-operative procedure can be performed to fully characterize the pelvis and, in some cases, the proximal femur. Thereafter, the shape, location and orientation of the acetabulum are known.

Also, the bony features around the acetabulum are known. From this data, a custom jig 700 can be fabricated specific to the patient. The custom jig 700 not only has features that are specific to the individual patient's anatomy but also a registration feature 702 that will be at a known orientation to the plane of the acetabulum and to the anterior pelvic plane.

FIG. 23 shows an example of the custom jig 700. The jig 700 has an anterior side 704 and a posterior side 708. The posterior side 708 is formed with an acetabular portion 712 configured to mate with at least one feature of the acetabulum in a secure manner. For example, the acetabular portion 712 can fit snugly over the acetabular rim with a central portion of the posterior side 708 positioned in the acetabulum. The jig 700 preferably has only one pre-defined orientation. A surface on a posterior portion of the jig can define a plane that corresponds to a preferred orientation angle of the cup post-implantation. One or more channels 716 can be formed on the posterior side 708 that receive the local bony prominences of the acetabular rim only when the jig 700 is in the proper position and orientation. In another approach, the registration feature 702 of the jig 700 has a face or a hole that is oriented in the desired orientation for the shell or cup of the implant. Thus, once the jig 700 is placed, the sensing device 204 can be positioned against the face or surface or, if coupled with a pin 732, the pin can be inserted into the hole. From the orientation of the device when so placed, the orientation of the acetabular rim or a proxy thereof can be recorded in one or both of the devices 172, 204. The hole 702 preferably extends from the anterior side 704 to the posterior side 708 of the jig 700. The distance between the anterior and posterior surfaces 704, 708 provides the depth of the hole 702 being sufficient to guide a pin to specific anatomy along a specific direction.

Figure 24:
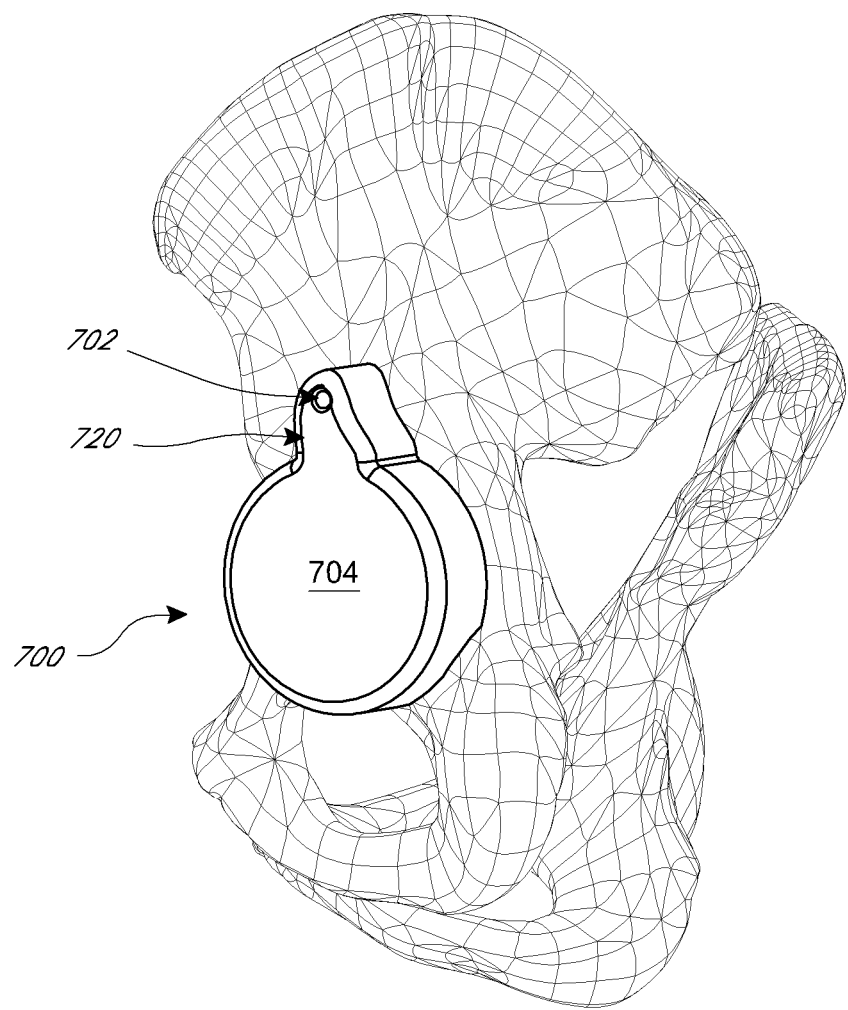

FIG. 24 shows initial placement of the jig 700 in the acetabulum in an orientation dictated by the fit of the jig 700 over the anatomy. The profile of the posterior side 708 including the channel(s) 716 receives the specific patient's acetabular rim including local prominences and recesses of the bone at and around the acetabulum. The hole 702 is located on a peripheral projection 720 of the jig 700. The configuration of the projection 720 is such that the hole 702 is disposed over a specific bone or bone region of the hip. In this example, the projection 720 is configured to be disposed over the bone superior to the acetabulum. Other regions of bone around the acetabulum can be used if sufficiently thick or strong and in a convenient position to not block actions of the surgeon during the procedure. The precise location of the projection 720 chosen can be determined by the pre-operative imaging and factored into the forming the custom jig 700.

Figure 25:
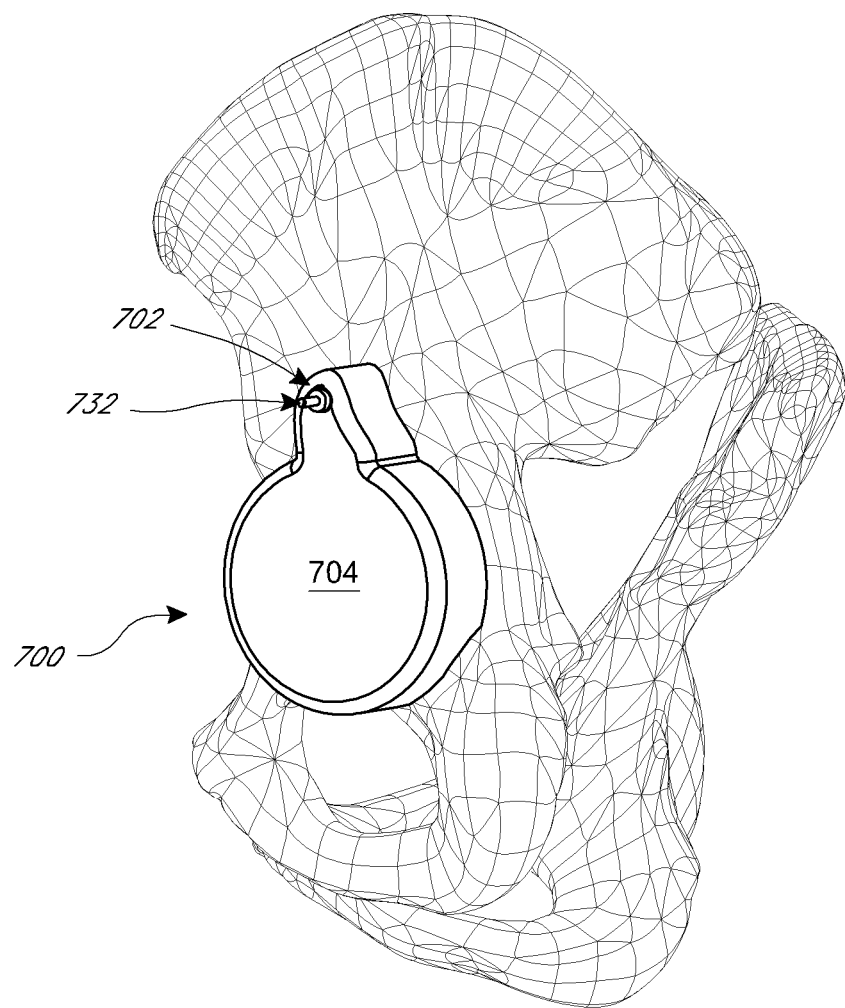

FIG. 25 shows that after the jig is placed the pin 732 can be placed through the hole 702. The pin 732 has a length that extends above the anterior surface 704 of the jig 700 such that the sensor 204 can be mounted thereto. Once the sensor 204 is mounted to the pin, the sensor can track any movement of the pelvis during the procedure. There is no need for registration of landmarks in this technique because the position and orientation of the pin relative to the acetabulum and/or to the anterior pelvic plane are known from the pre-operative imaging.

Figure 26:
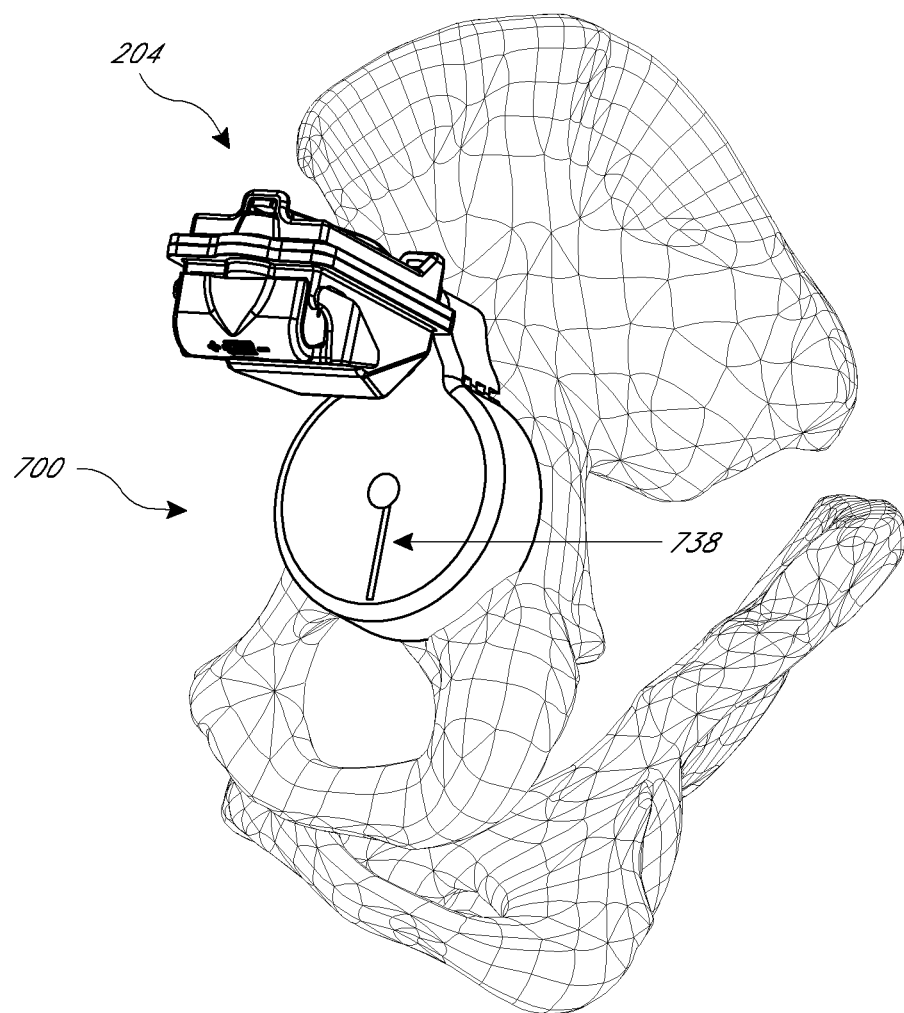
Figure 27:
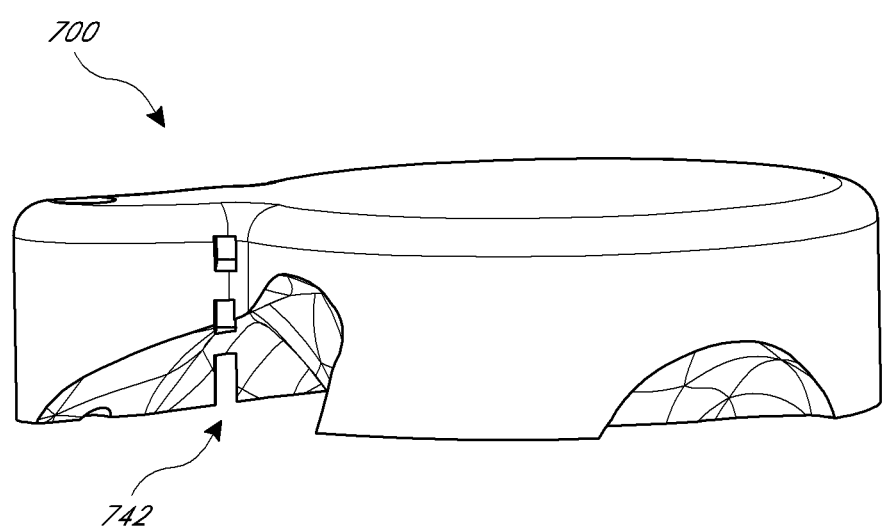

FIG. 26 shows that the plug 700 advantageously can include an alignment guide 736 to control rotational orientation of the sensor 204 on the pin 732. The alignment guide 736 can be a line extending along a specific direction relative to the registration feature 702. As noted above, the sensing devices inside the sensor 204 can be sensitive to the direction of gravity. Tilting of the sensor about the pin 732 can change the readings of these sensing devices. To eliminate sources of error associated with this sensitivity, the navigation system incorporating the sensor 204 can be programmed to assume that the sensor will be at a specific rotation position about the longitudinal axis of the pin 732. The sensor 204 may be mechanically or visually aligned with the guiding mark 738 to assure that this assumption is met in use. In one variation, the sensor 204 has a laser that projects onto the jig 700 and can be aliened with the mark 736 to facilitate alignment. Alternatively, the pin 732 may be configured to only enter the hole in a unique orientation (for example, with an asymmetric non-circular cross-section), and to allow the sensor to mount to the pin in a unique orientation (by including asymmetric coupling features).

Figure 28:
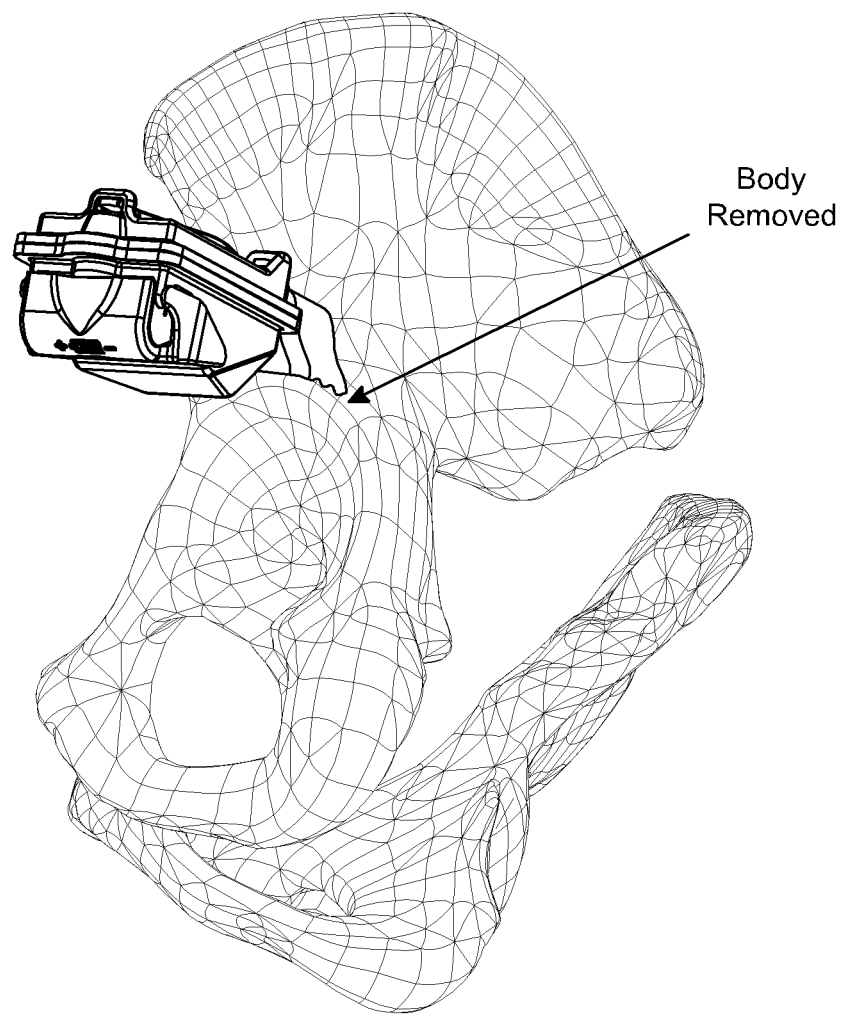

Once the sensor 204 is mounted to the pin 732, the jig 700 can be removed from the surgical area. For example, the jig 700 can be made of material can be cut along a line 742 in a lateral edge of the jig. A saw or rongeur can be used to cut through the jig 700. Thereafter, the majority of the body of the jig 700 can be removed from the surgical area. FIG. 28 shows that in some methods, the projection 720 is left in place so that the position and orientation of the sensor 204 is not disrupted.

A second sensor 204 is attached to a cup impactor, which may be the same as in FIGS. 11A-11C. The impactor guides the placement of the cup with reference to the signals from the sensor 204 mounted on the pin 732 on the pelvis. Signals from the sensor on the impactor can be corrected if movement of the hip is detected by the sensor on the pin 732.

2. Navigation Using Inertial Sensors and A Cannulated Guide

Figure 29:
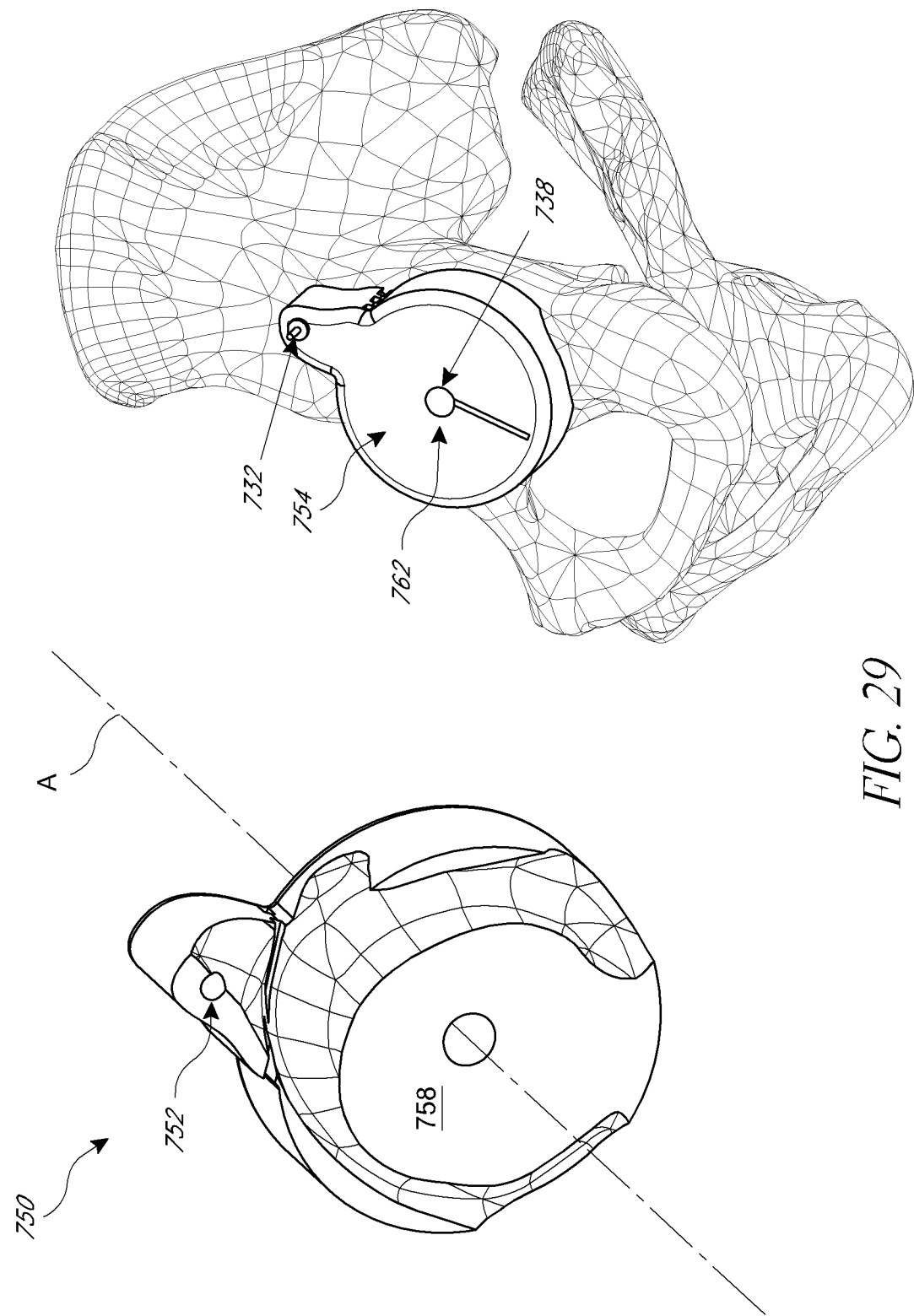
Figure 30:
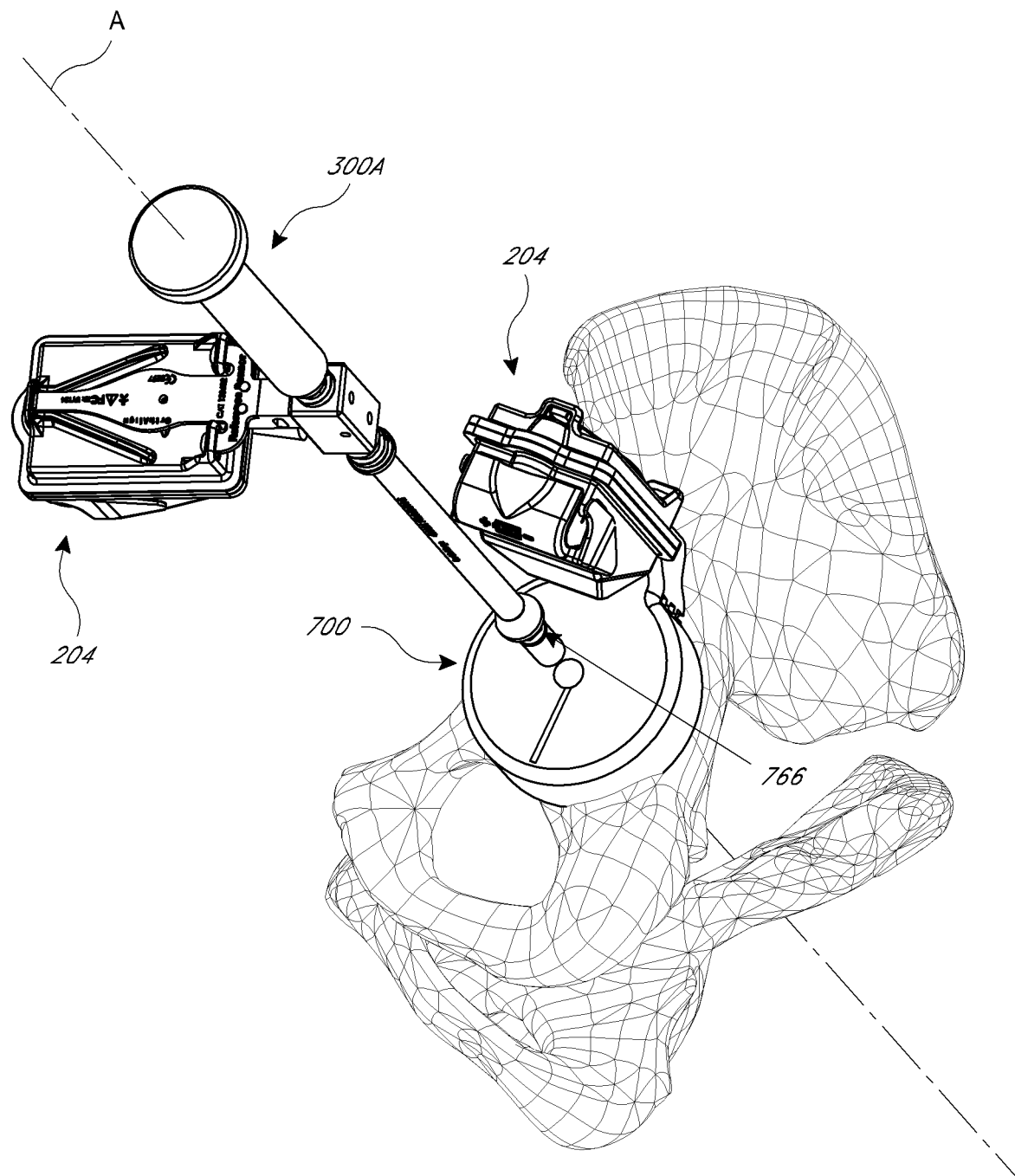
Figure 31:
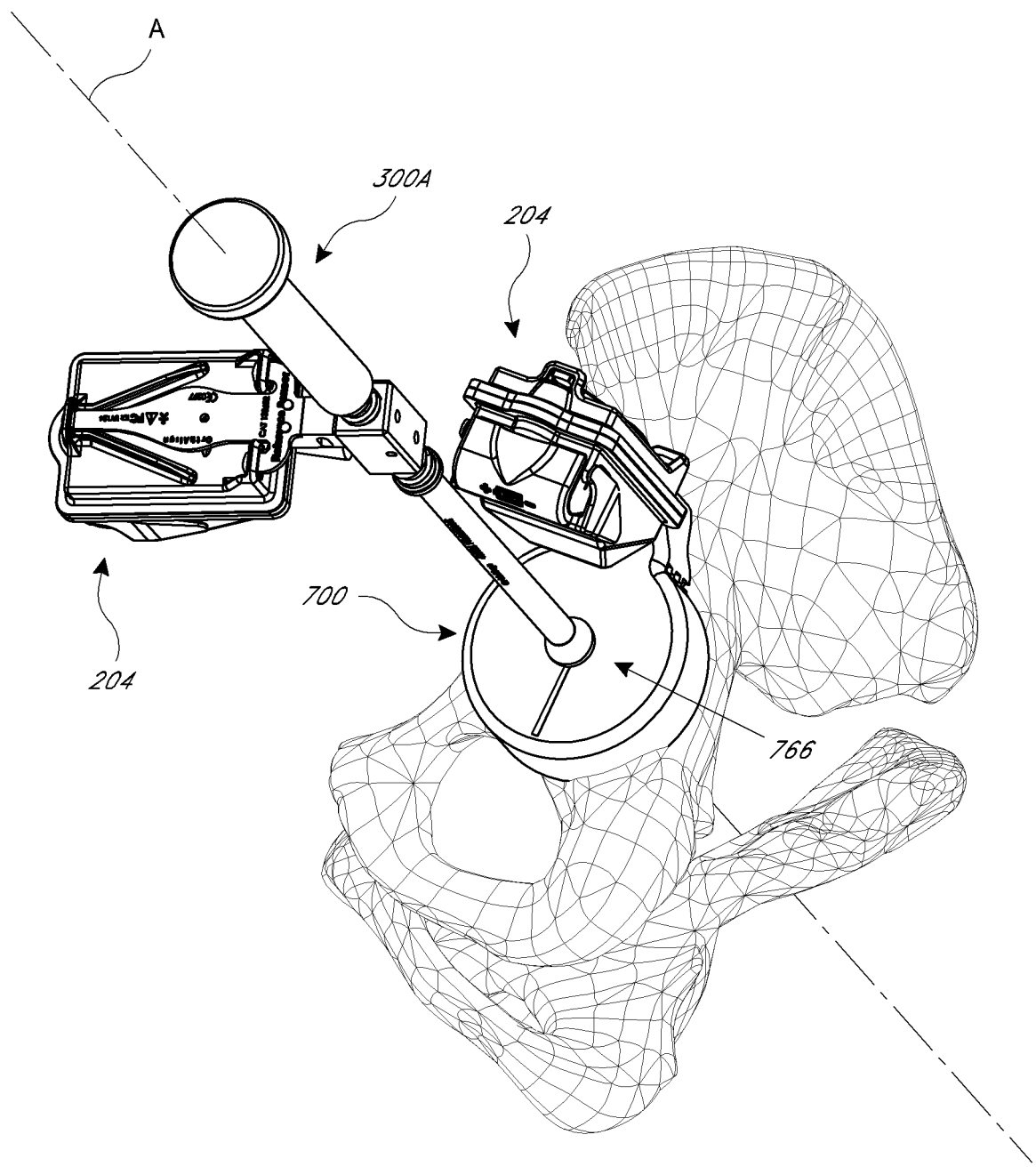

FIGS. 29-31 illustrate one way of implementing cannulated guide delivery methods. Cannulated methods are advantageous in that once a guide member is mounted, the tracking of orientation is simplified and may no longer be necessary in some cases, which can eliminate accumulated errors, sensor drift, or erroneous readings of other sorts as a concern.

A custom jig 750 is formed by the process discussed above in connection with the jig 700. The jig 750 has many of the same components as those of the jig 700, including a registration feature 752 extending between the anterior and posterior surfaces 754, 758. A guiding mark 738 can be provided on the anterior surface 754 to align the sensor 204 rotationally about the pin 732. The jig 750 also has a guide channel 762 located generally centrally in the jig 750. The guide channel 762 has an anterior opening on the anterior surface 754, a posterior opening on the posterior surface 758, and a wall extending between these openings. The wall is disposed about a central axis A. The position and orientation of the axis A can be determined based on the pre-operative characterization of the acetabulum. In one embodiment, an MRI or CT scan reveals an optimal axis for delivering a prosthetic cup along. The wall forming the guide channel 762 is formed about the axis A which coincides with this optimal axis when the jig 750 is placed on the specific patient's acetabulum.

FIG. 30 shows that the impactor 300A can then be advanced along the axis A into the guide channel 762. A distally facing shoulder 766 on the impactor 300A can mate in a pre-defined way with the anterior surface 754 and the entrance to the channel 762 and when so mated the orientation of the sensor 204 on the impactor 300A can be recorded. In this technique, the jig 750 is a cannula with the channel 762 configured to receive the impactor 300A. If patient movement is possible, the sensor 204 on the pin 732 can be retained in place to track such movement. If not, the sensor 204 on the pin 732 can be removed. The sensor 204 on the impactor 300A will have stored the orientation of the axis A in memory and will be able to inform the user of any variance of the impactor from this axis. It is preferred to retain the sensor 204 on the pin 732, as the orientation can only be accurate stored by the sensor 204 on the impactor 300A for a short time due to accumulated error (e.g., drift) of some sensors, e.g., some lower cost gyroscopes.

In one variation, the impactor 300A has a central channel that coincides with the axis A when the impactor is placed into the guide channel 762 and the shoulder 766 abutted with the surface 754. A guide pin can be advanced through this channel and into the acetabulum. The guide pin can be lodged in the base of the acetabulum. The sensor 204 coupled with the pelvis by the pin 732 can be removed because the guide pin placed through the channel of the impactor 300A provides a mechanical way of tracking movement of the hip. Thereafter the impactor 300A with the cup mounted thereon can be slide over the guide pin and into place in the acetabulum.

In a further variation, the sensor 204 coupled with the impactor 300A can also be removed. In this further variation, the guide pin is configured along with the cup to prevent tilting of the prosthetic cup relative to the axis A. In particular, an interface between the guide member and the cup of the hip prosthesis could be made to have sufficient length along the axis A that tilting is prevented by this interface. In some cases, the cup 360 is coupled to the impactor 300, 300A. A variation of the impactor 300, 300A can be tubular or have another feature for interfacing with, e.g., tracking along the guide pin in the pelvis.

3. Navigation Using Inertial Sensors and Pre-operative Imaging

In another technique using less comprehensive imaging, a correspondence between one or more linear dimensions and an angle can be exploited to enhance accuracy. For example, a clinician can use an X-ray or other standard radiographic imaging device to provide an anterior pelvic bone image. This image can be read to derive the location of the anterior pelvic plane and a dimension on the anatomy. For example, an angle between top and bottom landmarks around the acetabulum (as further describe below) and a trans-ischial line or other anatomic medial-lateral reference line can be a useful patient specific variable to minimize patient-to-patient variation in at least one relevant angle, e.g., the abduction angle.

Patient specific data can be provided for use by the surgeon based on best medical judgment. For example, any of the systems herein can be used in a mode that is based on broad population studies. Such studies can define a distribution of patients with sufficient clarity and detail to enable significant improvement over the current standard of care. In one mode, the dimensions taken from radiograph or CT can be used to inform the surgeon whether some patient specific adjustments should be considered. Alternatively, patient specific adjustments can be coded into the system 100 so that they are transparent to the doctor. Such adjustments can be downloaded to either or both of the devices 172, 204 or into a separate monitor or control device that communicates wirelessly with the devices 172, 204. Thus, the system 100 can either fully implement patient specific adjustment, e.g., for anteversion, abduction, leg length, joint offset, or other parameter or can enable the surgeon to make a judgment as to whether to do so.

Figure 36:
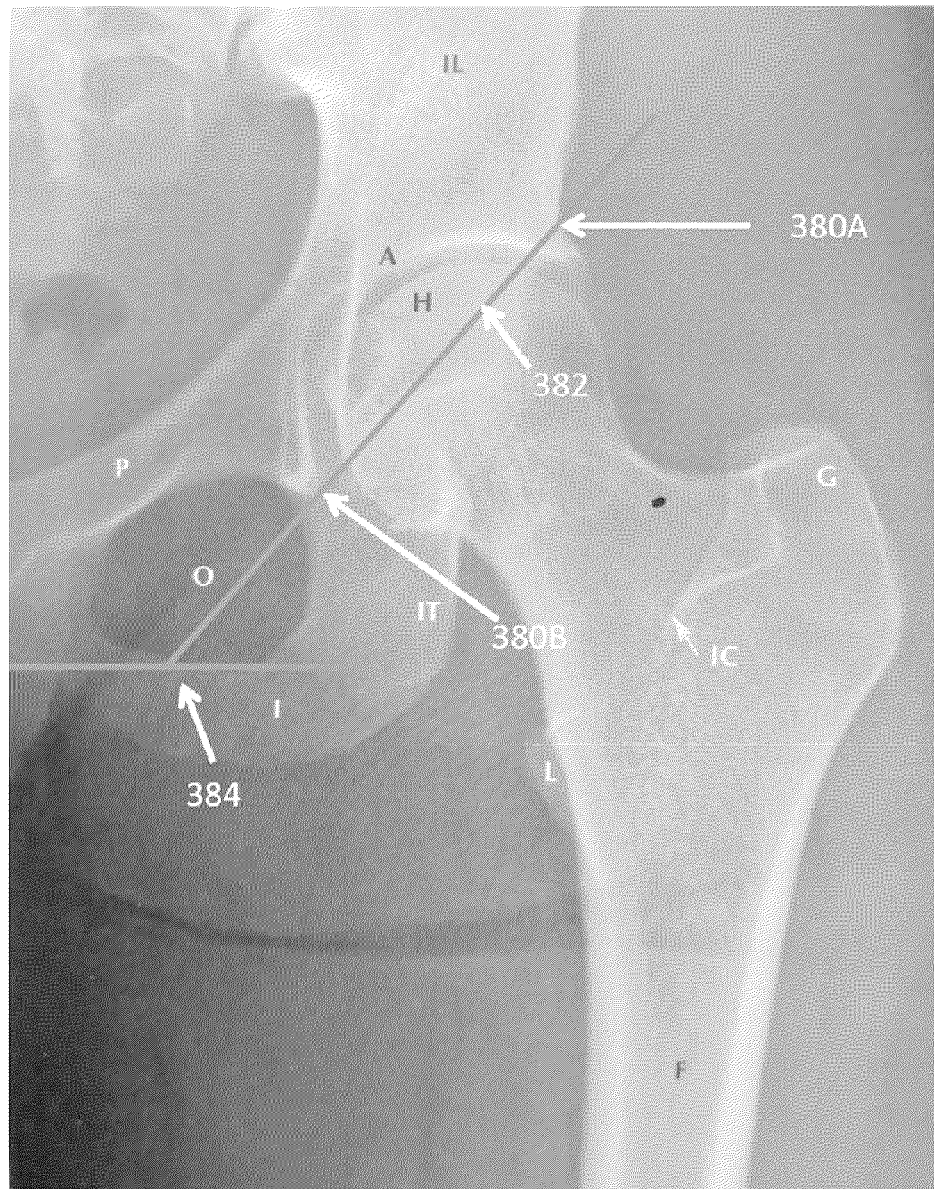
FIG. 36 is a pre-operative image that can be used to enhance alignment in a hip procedure by providing patient specific data.

FIG. 36 illustrates an example of a pre-operative image that can be used in one technique. The lines 380 point to landmarks which are used intraoperatively and are also visible in an anterior pelvic radiograph. The top landmark 380A is about 1 cm superior to most superior point of acetabulum. In another approach, the top landmark 380A can be the most superior point on the acetabular rim. The bottom landmark 380B is adjacent to or at the acetabular notch (tear drop). An angle between line 382 and the line 384 is a patient-specific abduction of line formed by landmarks, which can be entered into an interface of the system 100 (or the other systems herein) at time of surgery to provide patient specific reference frame. Line 384 may be any anatomic medial-lateral reference line. Examples include trans-ischial line and line across the inferior borders of the obturator foramina (shown in FIG. 36).

4. Navigation Using Drift Insensitive Inertial Sensors

In one variation, one or both of the devices 172, 204 can comprise only accelerometers and can be configured as tilt meters, or the devices could be put into a mode that relies mostly on the accelerometer data or otherwise be configured to be insensitive to accumulated errors that arise from integration of data. If the patient is set in a reproducible and stable position, patient movement and mis-orientation can be eliminated. This enables some methods to be performed without using rate sensor data. In one variation of this tilt-meter approach, one or both of the sensors 172, 204 can be configured to inform the surgeon if a condition is sensed that suggests a landmark acquisition approach would yield a superior alignment outcome. This method can advantageously be used for procedures that do not require complex movements, like freehand motions. Where freehand motion is involved, incorporating some indication of heading (gyroscopes, magnetometer, or other indication of heading) would be useful.

5. Navigation Using Inertial Sensors to Track Motion to Define a Patient-Specific Safe Zone In another technique illustrated by FIG. 32, a patient-specific "safe zone" is defined by recording the patient's natural range of motion of one more of the patient's joints. For example, if a hip procedure is to be performed, the patient's range of motion can be recorded pre-operatively. If the hip to be replaced is not overly arthritic, the range of motion can be determined on the hip to be replaced. If the range of motion of the hip to be replaced is unnatural due to disease state, the contralateral hip can be characterized.

In one hip replacement technique a sensor S is coupled with the femur. The sensor can be coupled above the knee to prevent movements at the knee from affecting the measurements made. The sensor S can be connected below knee if the knee is immobilized. The sensor S can be initialized and otherwise prepared to record accurate readings. Thereafter one or more movements of the hip joint can be performed with the output of the sensor recorded and processed. The movements can include, for example, movement in anterior and posterior (A-P) directions to the full extent of the range of motion and movement in medial and lateral (M-L) directions to the full extent of the range of motion. These motions define the patient's natural range of motions in these planes.

Figure 32:
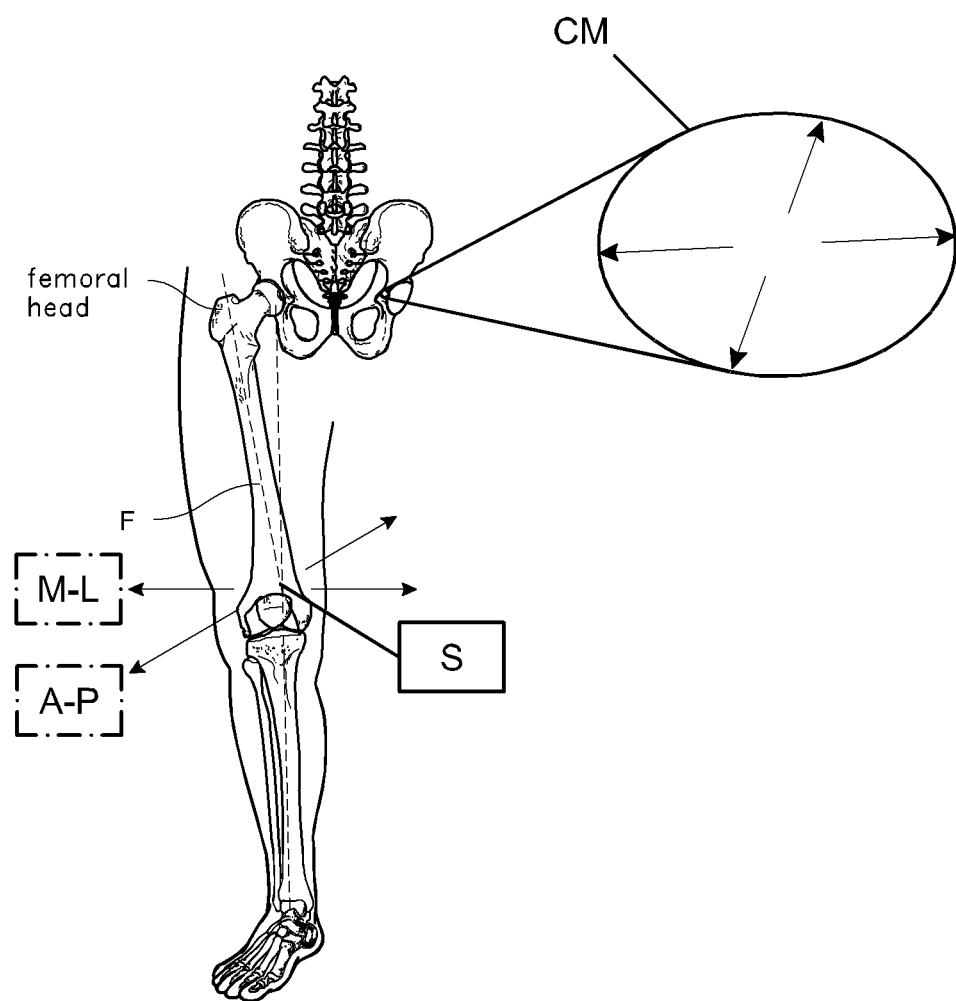
FIG. 32 illustrates methods for defining a patient-specific safe zone in a hip placement procedure.

Based on the extents of motion in the A-P and M-L directions, a cone of motion CM can be defined. The cone of motion CM can be defined as originating at a point defined as the center of rotation of the femoral head and extending out from the acetabulum to a circular base located a distance from the center of rotation equal to the distance to the mount point of the sensor. The circular base can be defined as having a radius equal to the average extent of motion in the A-P and M-L directions. In FIG. 32, the cone of motion is shown on the contralateral side for clarity. As noted above, the data collected to estimate the cone of motion can be based on the leg to be treated or the contralateral leg.

Placement of the cup of the hip prosthesis is dictated by some metric of centering within the cone of motion. For example, the cup can be centered such that an axis extending perpendicular to the plane of the entrance to the cup crosses the circular base of the cone of motion precise in the center of the cone. In some systems, the orientation of the cup is controlled such that the crossing point of the axis so projecting is closer to the center of the circular base than it is to the periphery of the circular base. In other systems, the orientation of the cup is controlled such that the crossing point of the axis so projecting is within a distance from the center point that is less than 25% of the radius of the circular base.

In a class of patients, the movement of the hip is not symmetrical in each of the A-P and M-L directions. As such, the cone of motion can have a more complex geometry. For example, the cone of motion can originate at the center of rotation of the femoral head and extend to a base having an oblong shape, for example shortened in the medial direction, but longer in the lateral, anterior, and/or posterior directions. Various metrics of "within the safe zone" can be defined based on these irregular shaped cones. For example the geometric center of a complex base shape can be calculated and the cup of the prosthetic joint can be centered such that an axis extending perpendicular to the plane of the entrance to the cup crosses the irregular shaped base of the cone of motion at or within some maximum distance of the centroid of the cone.

Any suitable set of motions can be used to obtain the center of rotation of the femoral head and/or the boundaries of the base of the cone of motion. Examples of methods for determining the center of rotation of a femoral head using inertial sensors are discussed in U.S. Pat. No. 8,118,815, which is hereby incorporated by reference for this and all other purposes. A more complete perimeter of the base of the cone of motion can be directly recorded using sensors that are capable of tracking both position and orientation. For example, several other points between the A-P and M-L direction can be taken so that six, eight, ten, twelve or more extents are recorded. In other embodiments, arcuate motions of along all or portions of the perimeter of the base of the cone of motion can be traced and recorded. Because several degrees of freedom of the sensor S are constrained, the sensor can operate based on accelerometers only in some approaches, which simplifies sensor S and enables it to be disposable and/or less expensive to make. Such approaches may be most accurate if rotations about a vertical axis are minimized or eliminated.

In one embodiment, the procedure illustrated in FIG. 32 generates an origin and a direction that can be input to a cup placement system. The origin can be the center of rotation of the femoral head and the corresponding center of rotation of a prosthetic socket. The direction can be a line connecting the origin and the point of intersection with the base of the cone of motion. This data is transferred to a cup placement system, such as any of those discussed above. For example, the impactor 300A can include the sensor 204 to which this data has been saved. Thereafter movements of the impactor 300A can be tracked with reference to this origin and direction to assure proper placement of the cup. Such placement can be with the aid of a patient movement tracking sensor pinned to the pelvis for example.

In other embodiments, cannulated systems can be used to minimize the number of steps during which inertial sensors are used. For example, once the origin and direction of the axis connecting the center of rotation and the intersection with the base of the cone of motion are determined, a guide member can be placed via a cannulated impactor (or other cannula). The guide member can dock with an impactor-mounted cup. The cup can be slid over the guide member into place in the acetabulum. The direction and origin information collected in the steps illustrated by FIG. 32 are preserved by the guide member and by the tilt preventing features on the guide member and/or prosthetic cup.

If the patient's joint is subject to extensive disease, a cone of motion can be established by a combination of data collected in motions similar to those discussed above in connection with FIG. 32 and pre-operative imaging. For example, X-rays can be taken when the femoral neck is moved close to the acetabular rim to supplement some of the data points defining the cone of motion. Thus, the cone of motion can be in part established by inertial sensing and in part by imaging to characterize the native anatomy.

D. Modular System for Anterior or Posterior Approach to Navigation Using Inertial Sensors and Anatomical Landmark Acquisition Jigs FIGS. 37-40 illustrate a system 900 for navigating a hip procedure. The system 900 can be similar to some of those discussed above. But, while some of the foregoing systems are specialized for a particular approach, the system 900 includes a first sub-system 900A adapted for a posterior approach and a second sub-system 900B adapted for an anterior approach. As discussed more below, both systems 900A, 900B are configured to enable navigation to be conducted without requiring gyroscopic or other sensors that are subject to accumulated error (drift). This refinement makes the system simpler to implement and to use in a wider variety of settings and with more patients.

The system 900A includes a jig 904A that is adapted for hip joint navigation from a posterior approach. The jig 904A is similar in some respects to the jig 454, and any consistent description thereof is incorporated herein. The jig 904A includes a platform 908, a cannula coupling device 912, and a registration jig mounting feature 914. The platform 908 can have any shape, but in some implementations can be elongate, e.g., having a first end 916 and a second end 920. The elongate shape enables at least a portion of the jig 904A to be low profile in one direction and to provide a plurality of positions along a length for coupling devices to the jig. The first end 916 is configured to be oriented inferiorly and the second end 920 to be oriented superiorly when the navigation jig is applied to the patient. The medial-lateral dimensions or extent can be minimized to not obstruct the surgical field or the surgeon.

The cannula coupling device 912 is disposed adjacent to the first end 916 and is configured to enable a cannula 924 to be held adjacent to a bottom surface of the platform 908. The cannula 924 can have a top surface connected to a bottom surface of the platform 908. A connection between these components can be secured by a device disposed above within or below the platform 908. In one form, a proximal structure of the cannula 924 can be received within a bottom recess of the platform 908 and can be held within the recess by a compression device, such as a set screw S. Details of several variants of cannula coupling devices 912 are discussed below in connection with FIGS. 41-43B. A connection to a bone adjacent to a hip joint is made through the cannula 924. For example, a pin 928 can be placed through the platform 908 and the cannula 924 into the bone.

Figure 39:
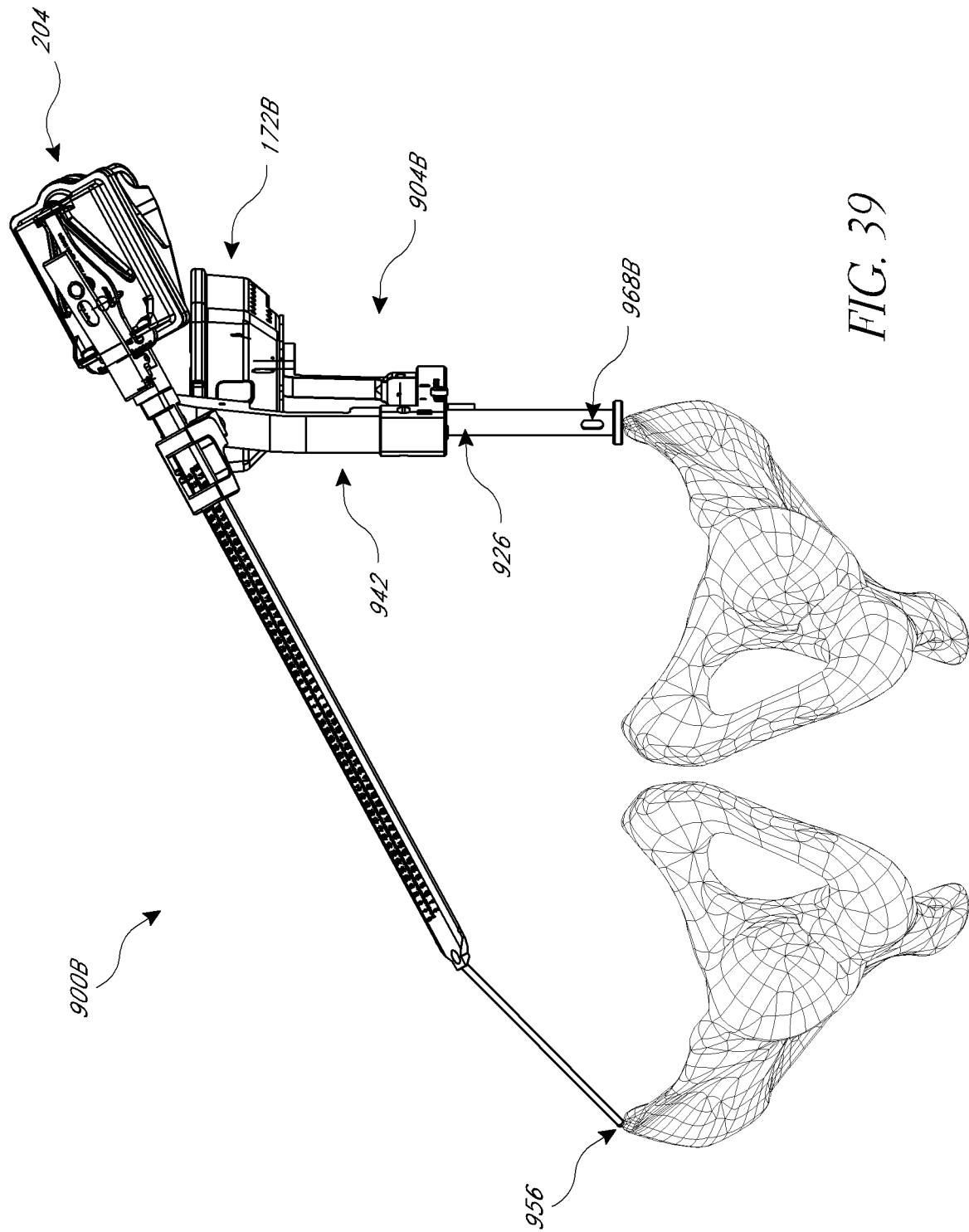
FIGS. 39 and 40 are view of the hip procedure navigation system of FIG. 37-38 modified and applied to a pelvis in an anterior approach.
Figure 40:
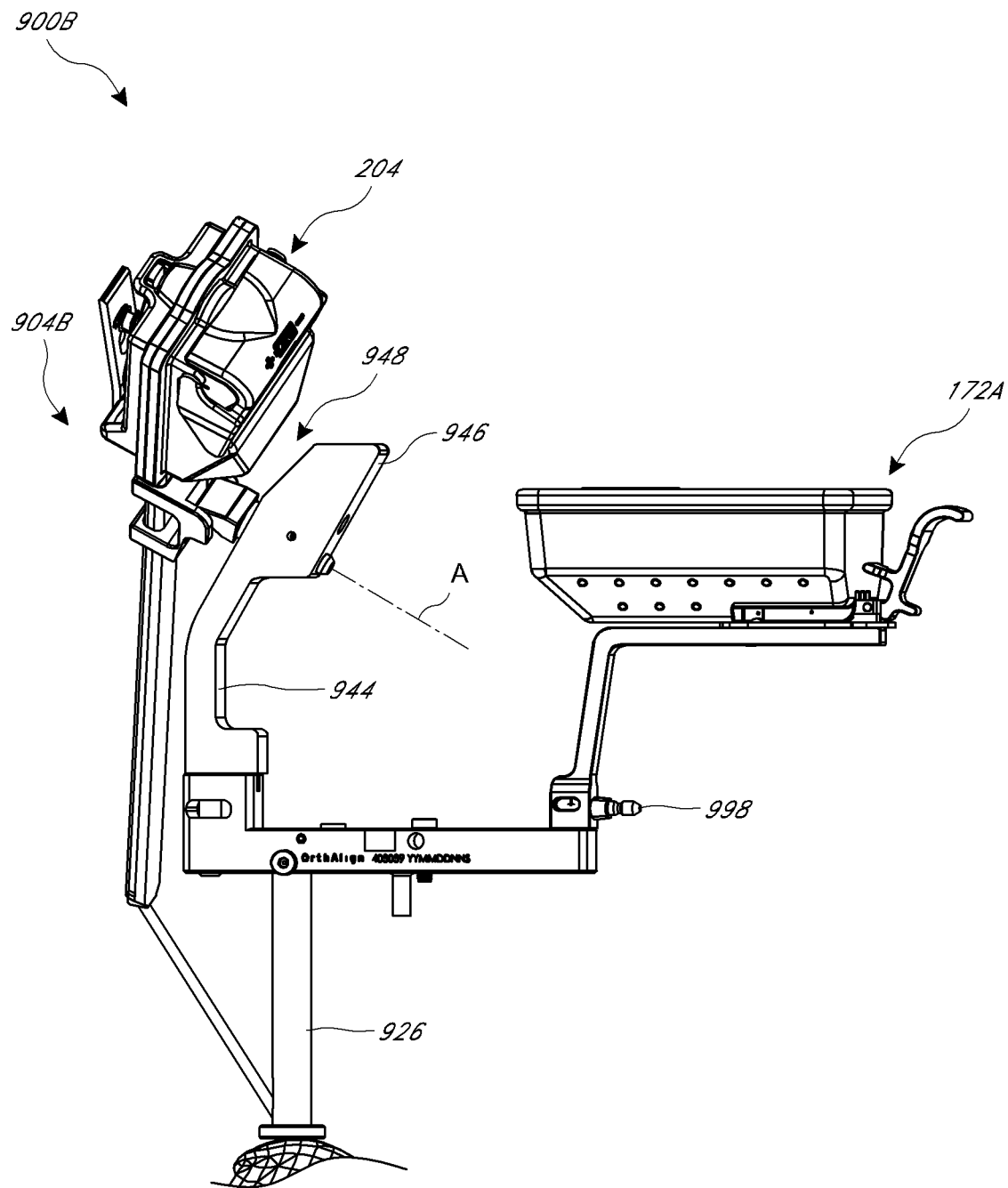

An anterior approach cannula 926 is shown in FIGS. 39 and 40 and is similar to the cannula 516, the description of which is incorporated herein. The description of the cannula coupling device 912 applies equally to the cannula 924 for posterior approach and to the cannula 926 for anterior approach.

Figure 41:
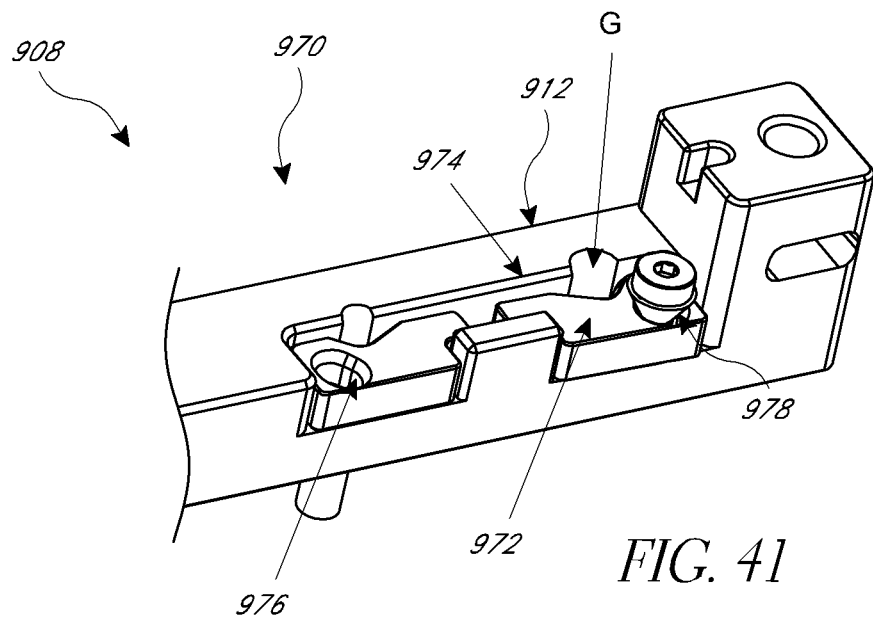
FIGS. 41-41A illustrate a first embodiment of pin securement devices.

The registration jig mounting feature 914 is disposed on a top surface 932 of the platform 908 adjacent to the first end 916. In one form, the mounting feature 914 includes an elevated portion of the platform. The mounting feature can include one or more, e.g., two recesses into which pins can be received. In one embodiment, the elevated portion includes a window, e.g., a through hole, for viewing such a pin to confirm correct placement. As illustrated in FIG. 41, in one variant, a circular recess can be provided for a first pin and an U-shaped slot can be provided for another pin or member.

The hip navigation jig 904A also includes registration jig 940. The registration jig 940 can have some features similar to those discussed above. The registration jig 940 includes an upright member 942, a rotatable member 948, and a probe 952. The upright member 942 is configured to be detachably coupled to the platform 908 at the registration jig mounting feature 914. For example, a plurality of (e.g., two) pins can project from a lower surface of the upright member 942, the pins being configured to be received in corresponding recesses in the registration jig mounting feature 914. One of such pins is visible through the window in the registration jig mounting feature 914 seen in FIG. 38. The upright member 942 includes a first portion 944 and a second portion 946 disposed above the first portion 944. The first portion 944 is substantially vertical and increases the elevation of the second portion 946 when the registration jig 940 is mounted to the registration jig mounting feature 914. The second portion 946 is inclined away from a vertical longitudinal axis of the first portion 944. The incline of the second portion 946 provides several advantages. It enables the upright member 942 to be out of the way of the range of motion of the probe 952, as discussed below. This is important because the probe 952 has to be able to easily and quickly reach a plurality of anatomical features.

The incline of the second portion 946 also provides a simple way to incline an angle of rotation of the rotatable member 948 relative to a vertical axis. The rotatable member 948 is coupled with the upright member 942 for rotation about an axis A that is not vertical when the jig is mounted to the bone adjacent to a hip joint and the upright member is disposed generally vertically. This arrangement is one way to enable a navigation system employing inertial sensors to eliminate the need to manage sensor drift. As discussed above, certain sensors, such as gyroscopes, are more subject to accumulated errors (drift). The orientation of the axis A enables the jig 904 to be used in a system that includes accelerometers and other sensors that are sufficiently sensitive if activated and moved about axes that are not vertical.

As in the registration devices discussed above, other degrees of freedom of rotation and position can be provided in the registration jig 940 and such description is incorporated here.

The probe 952 had a tip 956 for engaging anatomy. The anatomy engaging tip 956 is disposed at a distal end of an elongate body 960 coupled with the rotatable member for rotation about the axis. The orientation and position of the elongate body 960 of the probe can be adjusted to bring the anatomy engaging tip into contact with a plurality of anatomical landmarks during a landmark acquisition maneuver. Such adjustments can be by sliding through a sliding support, similar to those hereinbefore described.

The upright member 942 can include a cradle 954 that allows the elongate body 960 of the probe 952 to be held in place when not in use during a procedure. The cradle 954 can be used to latch the sensor 204, as discussed above. In various implementations, the system 900 does not require any steps of zeroing, however, since the sensors are configured to be generally drift insensitive. Eliminating sensitivity to drift can be achieved by configuring the sensor 204 as a tilt meter, and/or by using any sort of inertial sensor that will not introduce excessive error due to drift during the procedure time. As such, even sensors that have some drift can be used, so long as their accumulation of error does not reach a significant level until during the procedure. The cradle 954 could be used to zero error if a procedure was unexpectedly long and the sensor were subject to some drift. In one advantageous embodiment, the sensor 204 can operate solely with signals from accelerometers, which are insensitive to drift.

FIGS. 37-40 show that the systems 900A, 900B can include one or more sensors for detecting orientation of the probe 952. The sensors can take any form, e.g., can include the surgical orientation device 172 and the sensor 204 discussed above. Accordingly, the jig 904 can include a sensor mounting feature 962 disposed on the platform 908. Where the platform is elongate, the sensor mounting feature 962 can be disposed at the second end 920. Another advantage of the jig 904A, 904B is that it is symmetrical and can be used on both hips. The jig 904A, 904B thus can have a single sensor mounting feature disposed on a plane of symmetry. If the platform 908 is elongate, the sensor mounting feature 962 can be located on a vertical mid-plane of the platform. Vertical here refers to the orientation of the jig 904A, 904B when applied to the hip in a posterior or anterior approach.

The registration jig 940 can include a sensor mounting feature 964 disposed thereon for movement with the probe 952. For example, the sensor mounting feature 964 can be located at a proximal end of the elongate body 960. This location is one of convenience, placing the sensor 204 at the proximal end. However, the sensor mounting feature 964 and the sensor 204 could be located on a side surface of the elongate body 960.

As discussed herein, the orientation of the axis of rotation A of the rotatable member 948 enables the change of orientation of the sensor 204 to be other than in the horizontal plane. This is accomplished by orienting the axis A other than in the vertical direction. With this arrangement, it is possible to configure at least the sensor 204 as a tilt meter, e.g., using primarily or only accelerometers to output a signal indicative of orientation of a component, such as of the prove 952. Example of angles or ranges of angles of the axis A that can be provided include about 20 degrees from horizontal, about 30 degrees from horizontal, about 45 degrees from horizontal, at less than about 60 degrees from horizontal.

Figure 38:
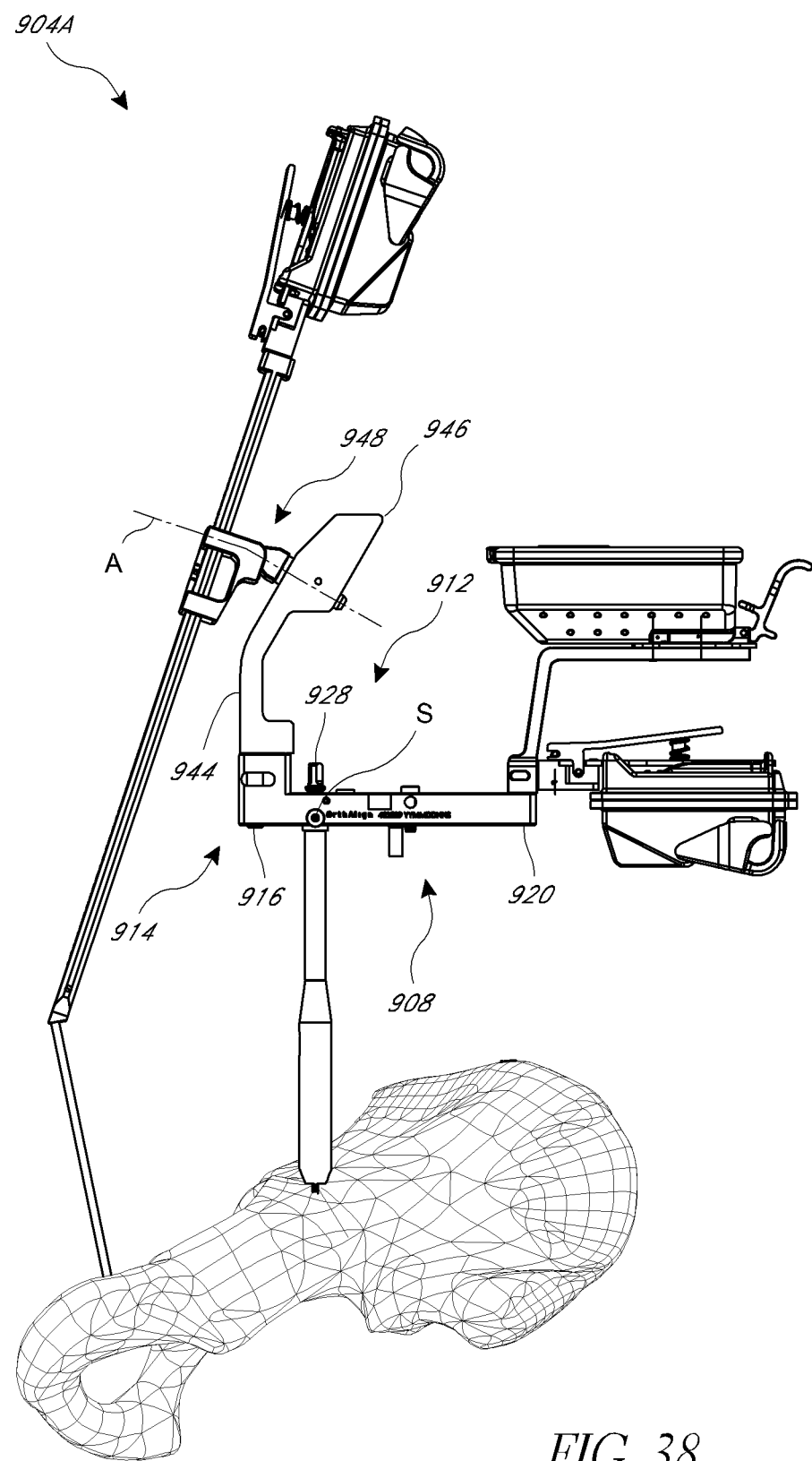

FIG. 38 shows a further feature of the system 900A, which includes the jig 904A and the cannula 924. The cannula 924 is adapted for posterior approach is similar to or the same as the hollow fixation member 466. An upper or first end of the cannula 924 is configured to couple with the cannula coupling device 912, such as by a set screw as discussed above. A second end of the cannula 924 is configured to couple with a bone adjacent to the hip joint. The bone can be any of those discussed above for coupling the fixation member 466 or other analogous structures discussed in any embodiments above. A home point feature 968 is disposed adjacent to the second (lower) end of the cannula 924. The home point feature 968 is in a predefined, known position and can receive the anatomy engaging tip 956 of the probe 952. When these structures contact, they are in a predefined position and orientation. The home point feature 968 can be similar to the registration feature 473 discussed above.

Because the system 900 can be adapted for posterior approach or for anterior approach (discussed below), the cannula 924 should be made removable from the platform 908 in the operating room or at a back table in preparation for surgery. As such, the connection between the cannula 924 and the platform 908 can be made orientation specific. This reduces a potential source of operator error, i.e., the home point feature 968 always faces toward the surgical field from the hip bone attachment location, e.g., faces inferiorly if the jig 904 is mounted to a superior location of the surgical field. For example, a projection on a proximal portion of the cannula 924 and a corresponding projection in a recess on the lower side of the platform 908 can define only one rotational orientation of the cannula relative to the platform in which these components can be coupled.

As discussed above, the cannula 926 is provided in the system 900 to enable a surgeon to switch to an anterior approach. Anterior approach is discussed in great detail above, e.g., in connection with FIGS. 18-21B, which description are incorporated here as well. The system 900B differs from the system 500 in that the orientation of the axis A of rotation in the system 900B is not vertical, as discussed above. As such, the sensors can be greatly simplified compared to the system 500. The cannula 926 has a home point feature 968B. The home point feature 968B is in a predefined, known position and can receive the anatomy engaging tip 956 of the probe 952. When these structures contact, they are in a predefined position and orientation. The home point feature 968B can be similar to the registration feature 473 discussed above. The cannula 926 and the platform 908 can be configured for limited, e.g., only one, rotational position of attachment. This assures that when the jig 904B is assembled in the operating room or back table that the jig 904B will be properly set up.

In one method to maximize the accuracy of the landmark acquisition, jig 904B is coupled with the patient in an anterior approach. The tip 956 is put into contact with the home point feature 968B. Thereafter, user input can be applied to the surgical orientation device 172A to indicate that the tip 956 is in the home point feature 968B. Thereafter, the system registers movements and landmark acquisition in the manner discussed above. These data provide a basis to guide the placement of the acetabular cup, as discussed above.

Figure 37:
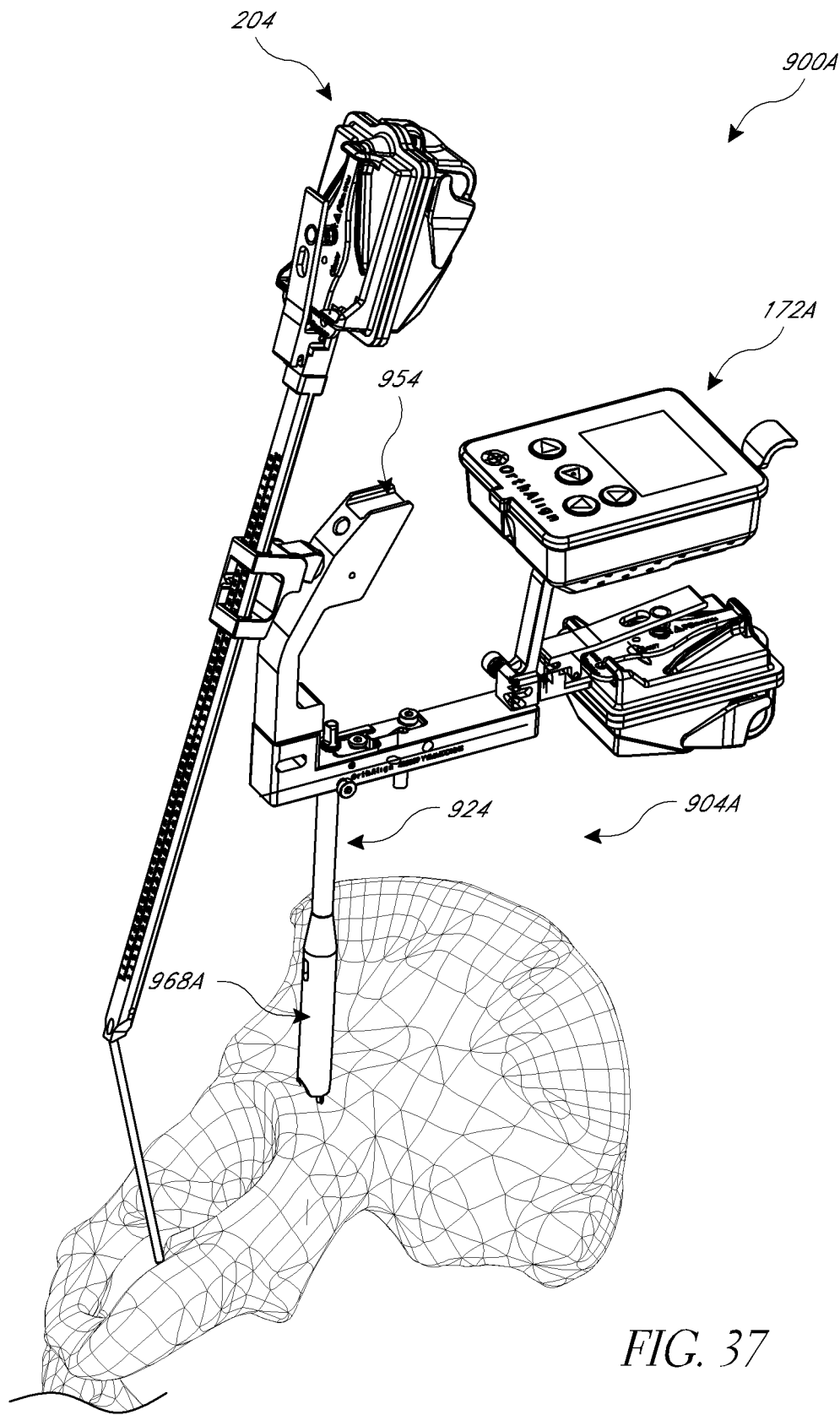
FIGS. 37 and 38 are views of a hip procedure navigation system applied to a pelvis in a posterior approach.

The placement of the acetabular cup using a device such as the impactor 300A can be an operation that benefits from inertial sensors that may include one or more drift-sensitive sensors, e.g., gyroscopes. The system 900 provides a calibration mount 998 for coupling a sensor 204 in a known, fixed position and orientation relative to the surgical orientation device 172A. The calibration mount 998 is a docking device that positions the sensor 204 just prior to a step of eliminating any potential source of accumulated error, e.g., zeroing a drift-sensitive sensor. FIG. 37-38 show that they system 900A can include two sensors 204, one mounted to the registration jig 940 and one to the calibration mount 998. These two sensors 204 can be identical or can be dedicated for their specific function. FIGS. 39 and 40 shows only one sensor 204. In this system, a single sensor 204 is used to gather landmark data and to work in combination with the impactor 300A to place an acetabular implant.

Figure 41A:
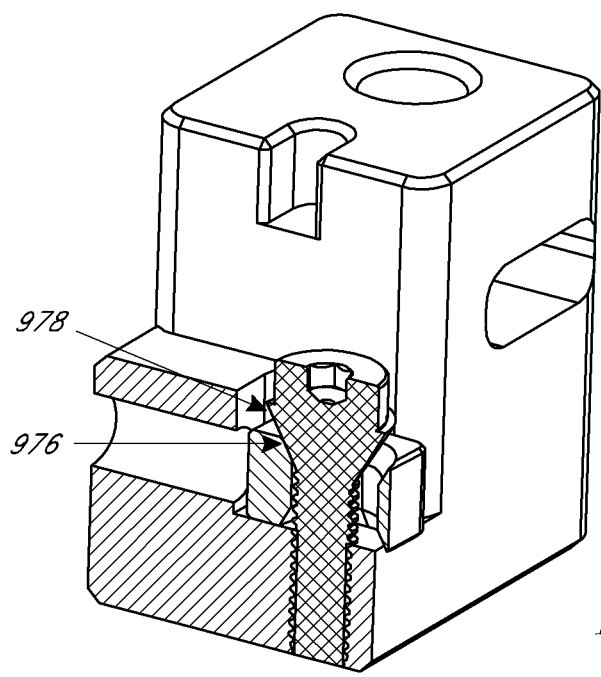

FIGS. 41-43B illustrate various features for clamping structures to the platform 908. In particular, these figures show fixation pin securement devices 970 that are incorporated into the platform 908. The fixation pin securement devices 970 can have low profile to be out of the way of other tools in the surgical field. FIG. 41-41A show one embodiment of a pin securement device 970 that includes a compression member 972. The cannula coupling device 912 can include a similar mechanism to clamp a pin disposed through the cannula 924. The platform 908 includes a slot or plurality of slots formed on a surface thereof, e.g., on the top surface. The slots 974 are larger in at least one direction than the compression member 972 such that the compression member can fit in the slot and move to some extent therein. The compression member 972 has a tapered channel 976. Movement of a tapered member 978 vertically in the tapered channel 976 shifts the compression member 972 to narrow a gap G between the compression member 972 and a rigid feature of the platform. The gap G can be between a curved lateral surface of the compression member 972 and a curved surface of the platform 908.

In one method, a pin or other fixation member is advanced through the gap G and into the bone. The platform 908 is positioned on the fixation member at an appropriate height and the pin securement device 970 is affixed to the fixation member. The fixation member can be a Steinmann pin or other similar device. In one technique, the tapered member 978 is a threaded elongate body that is advanced along internal threads formed in the platform 908 until the tapered surface thereof acts on the tapered surface 976 to shift the compression member 972 laterally to narrow the gap G. Further advancement of the tapered member 978 further shifts the compression member 972 to enhanced securement of the fixation member. The method can be repeated for a second pin, where one pin extends through the cannula 924 and one extends parallel to the cannula 924, but off-set superiorly therefrom on the patient.

FIGS. 42-42B illustrate another approach to a fixation pin securement devices 970A in which the fixation pin securement device comprises a compression member 972A pivotally mounted to the platform 908. FIG. 42A shows two compression members 972A, each of which is mounted to pivot about a pin or shaft 980. The securement device 970A on the left in FIG. 42A corresponds to a configuration in which a fixation member can freely pass through a gap G in the mechanism. The securement device 970A on the right in FIG. 42A corresponds to a configuration in which the gap G is narrowed and a fixation member disposed in the gap G will be securely clamped and unable to move relative to the platform 908. A rigid surface of the platform 908 opposite the pivoting compression member 972 along with the compression member holds the fixation member in place.

In one method, pins or other fixation members are placed in the fixation pin securement device 970A and the cannula coupling device 912. In the illustrated embodiment, these devices can employ similar clamping mechanisms. Thereafter, screws 982 are advanced to cause the compression member 972 to pivot about the pin or shaft 980 from a first position in which the gap G provided between a clamping surface of the compression member 972A and a rigid surface of the platform 908 is larger to a second position in which the gap G is smaller. The second position is a clamped position for the fixation member and will retain the platform in position until the screw 982 is withdrawn enlarging the gap G.

FIGS. 43-43B illustrate another approach to a fixation pin securement devices 970B in which the fixation pin securement device comprises a compression member 972B configured to clamp a plurality of segments of an outside surface of a fixation member. The platform 908 includes a plurality of projections 984 extending upward from an upper surface of the platform. The projections preferably are threaded. Each projection includes a collet 986 or similar device disposed therein having an inner lumen sized to receive a fixation member. A plurality of slots extends downward from an upper surface of the collet 986 and an angled surface 988 is disposed between top ends of each member defined between a pair of such slots. A corresponding angled surface 990 is provided on an inside of a cap 992. The cap 992 has internal threads that act on the threads of the projection 984 to advance the angled surfaces 990 onto the angled surfaces 988. Further advancement collapses the slots of the collet 986 causing compression about the outer surface of the fixation member. FIG. 43 shows that this approach can be used for the fixation pin securement devices 970B and/or for the cannula coupling device 912.

While the systems discussed above are well suited for specific approaches, the system 900 can be adapted for a posterior approach or for an anterior approach. This provides a great deal of flexibility to the surgeon and only adds minimal additional components to a universal kit. The orientation of the axis of rotation A (see FIGS. 38 and 40) enhances the sensitivity of a system that incorporates accelerometers and other sensor drift insensitive components. The home point features 968A, 968B enable the surgeon to obtain maximal accuracy by allowing the acquisition of position and orientation data for a number of anatomical landmarks at close range to the home point position. This allows the system to initialize the sensors near the points to be acquired to enhance accuracy.

II. Hip Navigation Using Camera Tracking

Figure 33:
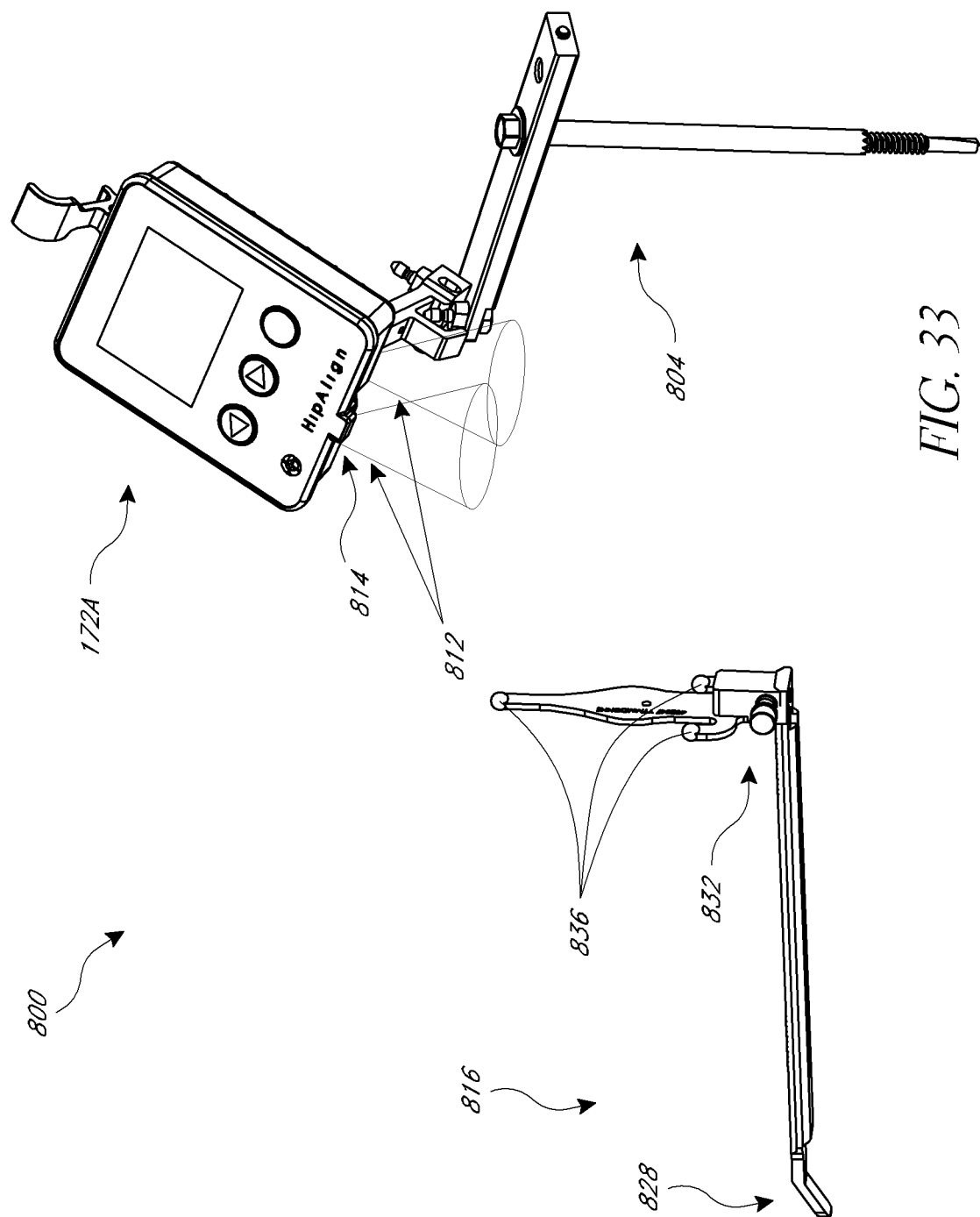
FIG. 33 is an embodiment of a system for close range optical tracking.

FIG. 33 illustrates one embodiment of a system 800 that includes close-range optical tracking capabilities. In this context "close range" is a broad term that means near the patient, such as any of in the surgical field, directly above the pelvis but below the surgeon's head, within the boundaries of the surgical table, etc. This term is intended to exclude systems where cameras are outside the surgical fields. Close range greatly reduces or eliminates "line of sight" problems that plague traditional optical navigation.

In the illustrated embodiment, a jig system 804 is provided for connecting to patient bone. The jig system 804 can include any of the features of any of the jig systems discussed herein. For simplicity, the jig system is illustrated with that of FIG. 1, e.g., including the cannula 124 and the platform 136. A surgical orientation device 172A is mounted to the platform 136. The orientation device 172A can be similar to those hereinbefore described, but also includes one or more cameras 812. Preferably the orientation device 172A includes two or more cameras 812 to enable capture of binocular data. The cameras preferably are small cameras, for example the Aptina MT9T111, which is discussed at http://www.aptina.com/products/soc/mt9t111d00stc/. The cones projecting from the lower side of the device 172A schematically represent the direction of the field of view of the cameras 812.

This data can at least be used to determine the heading of and in some cases six degrees of freedom of a stylus 816. The stylus has a distal end 828 configured to touch landmarks as part of a landmark acquisition maneuver, as discussed above. A proximal (or other) portion 832 of the stylus 816 has an array of trackers 836 that can be tracked by the cameras 812 to provide orientation, position, heading, attitude, or other combinations of spatial characteristics of portions of the stylus 816 or anatomy with which it is coupled.

The cameras 812 can operate without any additional sensor, such as inertial sensors. In some embodiments, the cameras 812 are used in concert with inertial sensors to confirm or to improve accuracy of the sensors. For example, drift in a rate sensor, e.g., accumulated errors, can be monitored by comparing the output of the rate sensor with the viewed position from the cameras. The system can intervene if the sensor output drifts too much, for example, telling the user to reset the rate sensors.

Another optical device such as a laser or an IR emitter 814 can be provided in the orientation device 172A. An IR emitter can be useful to illuminate the fiduciaries to make them more readily detectable by the cameras under the intense lighting in the surgical field.

Although these inventions have been disclosed in the context of certain preferred embodiments and examples, it will be understood by those skilled in the art that this application extends beyond the specifically disclosed embodiments to other alternative embodiments and/or uses of the invention and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within the scope of the application. For example, the application contemplates the connection hub alone or in combination with any of the other modules could comprise a separate aspect. Or, any one or a combination of the modules could be directly connected to an umbrella hub or overhead support to form another separate aspect. Accordingly, it should be understood that various features and aspects of the disclosed embodiments can be combined with or substituted for one another in order to form varying modes of the disclosed embodiments. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A system for performing a hip joint replacement, comprising:
   an orientation sensing device, wherein the orientation sensing device comprises at least one inertial sensor, wherein the at least one inertial sensor is sensitive to the direction of gravity;
   two pins configured to be driven into the pelvis in a spaced apart configuration;
   a support platform configured to receive the two pins to couple the support platform to the patient positioned relative to a surgical table, the patient having a hip joint comprising an acetabulum and a femoral head, wherein the support platform comprises a locking device for securing the platform to the pins, wherein the orientation sensing device is configured to couple to the support platform, wherein, in use, an orientation of the inertial sensor is recorded as an indication of the orientation of a reference frame comprising a first plane and a second plane when the orientation sensing device is coupled to the support platform coupled to the patient;

an impactor docking device, wherein the orientation sensing device is configured to be decoupled from the support platform coupled to the patient and then coupled to the impactor docking device, wherein the orientation sensing device provides an indication of the orientation of an impactor relative to the reference frame comprising the first plane and the second plane based upon an orientation of the inertial sensor of the orientation sensing device when the orientation sensing device is coupled to the impactor docking device, wherein the support platform is configured to remain coupled to the patient while the orientation sensing device is coupled to the impactor device and provides the indication of the orientation of the impactor.

2. The system of claim 1, wherein the at least one inertial sensor comprises at least one accelerometer.

3. The system of claim 1, wherein the at least one inertial sensor comprises at least one gyroscope.

4. The system of claim 1, wherein the orientation sensing device comprises software incorporated into a processor.

5. The system of claim 1, wherein the orientation sensing device comprises a computer.

6. The system of claim 1, wherein the orientation sensing device is configured to calculate a transformation from one reference frame to another.

7. The system of claim 1, wherein the orientation sensing device is configured to process an algorithm.

8. The system of claim 1, wherein the orientation sensing device is configured to execute software.

9. The system of claim 1, wherein the orientation sensing device is configured to provide real time navigation data.

10. The system of claim 1, wherein a placement of a cup is guided without registering landmarks.

11. The system of claim 1, wherein the first plane is parallel to the surgical table.

12. The system of claim 1, wherein the second plane is perpendicular to the surgical table.

13. The system of claim 1, wherein the first plane contains an anterior pelvic plane.

14. The system of claim 1, wherein the second plane is perpendicular to an anterior pelvic plane.

15. The system of claim 1, wherein a first hip joint of the patient is configured positioned on the surgical table and a second hip joint of the patient is positioned off of the table.

16. The system of claim 1, wherein an impactor is configured to place a cup of an artificial hip joint in the acetabulum with the orientation sensing device coupled to the impactor docking device.

17. The system of claim 1, wherein the orientation sensing device extends perpendicular to an axis of the impactor.

* * * * *